(12) United States Patent
Tsukahara et al.

(10) Patent No.: US 12,290,792 B2
(45) Date of Patent: *May 6, 2025

(54) TREATMENT APPARATUS

(71) Applicant: Microwave Chemical Co., Ltd., Osaka (JP)

(72) Inventors: Yasunori Tsukahara, Osaka (JP); Satoshi Morikawa, Osaka (JP); Yukari Deguchi, Osaka (JP); Yuka Kotake, Osaka (JP); Hideshi Kurihara, Osaka (JP); Hisao Watanabe, Osaka (JP); Fumihiro Kayamori, Osaka (JP); Kanako Kaihara, Osaka (JP)

(73) Assignee: Microwave Chemical Co., Ltd., Osaka (JP)

( * ) Notice: Subject to any disclaimer, the term of this patent is extended or adjusted under 35 U.S.C. 154(b) by 37 days.

This patent is subject to a terminal disclaimer.

(21) Appl. No.: 18/295,819

(22) Filed: Apr. 4, 2023

(65) Prior Publication Data

US 2023/0256410 A1 Aug. 17, 2023

Related U.S. Application Data

(63) Continuation of application No. 16/306,216, filed as application No. PCT/JP2018/014910 on Apr. 9, 2018, now Pat. No. 11,633,709.

(30) Foreign Application Priority Data

May 23, 2017 (JP) .................................. 2017-101859
Jun. 19, 2017 (JP) .................................. 2017-119846

(Continued)

(51) Int. Cl.
*B01J 19/12* (2006.01)
*C07H 1/00* (2006.01)
*C07K 1/04* (2006.01)

(52) U.S. Cl.
CPC .............. *B01J 19/126* (2013.01); *C07H 1/00* (2013.01); *C07K 1/045* (2013.01);
(Continued)

(58) Field of Classification Search
CPC .............. B01J 19/126; B01J 2219/1224; B01J 2219/1242; B01J 2219/1266; B01J 19/087;
(Continued)

(56) References Cited

U.S. PATENT DOCUMENTS 4,400,604 A 8/1983 Ohtsuka et al.
5,053,244 A 10/1991 Kieser et al.
(Continued)

FOREIGN PATENT DOCUMENTS

CN 101428345 A 5/2009
CN 100546712 C 10/2009
(Continued)

OTHER PUBLICATIONS

International Search Report mailed during the prosecution of International Patent Application No. PCT/JP2017/040216.
(Continued)

*Primary Examiner* — Xiuyu Tai
(74) *Attorney, Agent, or Firm* — Troutman Pepper Locke LLP

(57) ABSTRACT

In order to provide a treatment apparatus that can efficiently perform microwave irradiation, a treatment apparatus includes: a vessel made of a microwave-reflecting material, and having a first end and an irradiation opening portion, which is an emitting portion of microwaves that are emitted into the vessel; a first filter located so as to partition the vessel, and configured to separate solids that are to be separated, from the contents of the vessel; and a first reflecting member located closer to the first end than the
(Continued)

emitting portion is and so as to partition the vessel, and configured to allow at least the contents having passed through the first filter to pass through the first reflecting member, and to reflect microwaves.

21 Claims, 14 Drawing Sheets

(30) Foreign Application Priority Data

| | | |
|---|---|---|
| Feb. 27, 2018 | (JP) | 2018-033004 |
| Apr. 2, 2018 | (JP) | 2018-070798 |
| Apr. 2, 2018 | (JP) | 2018-070799 |

(52) U.S. Cl.
CPC ..... *B01J 2219/1224* (2013.01); *B01J 2219/1242* (2013.01); *B01J 2219/1266* (2013.01)

(58) Field of Classification Search
CPC ........ B01J 2219/0871; B01J 2219/1254; B01J 2219/1272; B01J 2219/1221; B01J 2219/1215; B01J 2219/1209; B01J 2219/0879; B01J 2219/1293; B01J 2219/1206; B01J 2219/126; B01J 2219/1218; B01J 20/3242; B01J 20/286; B01J 20/281; B01J 2219/1227; B01J 2220/54; C07H 1/00; C07K 1/045; C07K 7/06; C07K 5/08; C07K 1/063; B01D 15/16; B01D 15/22; B01D 15/3857; B01D 15/20; G01N 2030/3046; G01N 30/12; G01N 2030/121; G01N 30/06; H05B 6/806

See application file for complete search history.

(56) References Cited

U.S. PATENT DOCUMENTS

| | | | |
|---|---|---|---|
| 5,532,462 | A | 7/1996 | Butwell et al. |
| 7,393,920 | B2 | 7/2008 | Collins et al. |
| 2003/0205455 | A1 | 11/2003 | Jamalabadi et al. |
| 2008/0124253 | A1 | 5/2008 | Schmidt et al. |
| 2011/0266717 | A1 | 11/2011 | Nehls et al. |
| 2013/0192423 | A1 | 8/2013 | Yang et al. |
| 2015/0206778 | A1 | 7/2015 | Shimomura |

FOREIGN PATENT DOCUMENTS

| | | | |
|---|---|---|---|
| CN | 102648042 | A | 8/2012 |
| CN | 103139951 | A | 6/2013 |
| CN | 103894624 | A | 7/2014 |
| CN | 103998121 | A | 8/2014 |
| CN | 104604331 | A | 5/2015 |
| EP | 1533025 | A2 | 6/2004 |
| EP | 1491552 | A2 | 12/2004 |
| EP | 1935485 | A1 | 6/2008 |
| EP | 2323461 | A1 | 5/2011 |
| EP | 2781258 | A1 | 9/2014 |
| JP | H56-128592 | A | 10/1981 |
| JP | 59-012948 | B | 3/1984 |
| JP | H08-83681 | A | 3/1996 |
| JP | H10-54660 | A | 2/1998 |
| JP | 2000-506127 | A1 | 5/2000 |
| JP | 2002-301136 | A | 10/2002 |
| JP | 2004-147648 | A1 | 10/2003 |
| JP | 2005-15483 | A | 1/2005 |
| JP | 2005-75660 | A | 3/2005 |
| JP | 2007-54774 | A | 3/2007 |
| JP | 2008-272729 | A | 11/2008 |
| JP | 2009-243415 | A | 10/2009 |
| JP | 2010-184230 | A | 8/2010 |
| JP | 2012-40459 | | 3/2012 |
| JP | 2013-144822 | A | 7/2013 |
| JP | 2014-95050 | A | 5/2014 |
| JP | 2015-40316 | A | 3/2015 |
| JP | B5936759 | B | 6/2016 |
| TW | 201437300 | A | 10/2014 |
| WO | 9730784 | A1 | 8/1997 |
| WO | 2008/074799 | A1 | 6/2008 |

OTHER PUBLICATIONS

Eun-Jong Lee,Yong-Hoe Kim,Do Kyung Hwang,Won Kook Choib, Jin-Yeol Kim, "Synthesis and optoelectronic characteristics of 20 nm diameter silver nanowires for highly transparent electrode films," RSC Adv. vol. 6, pp. 11702-11710, (2016).
First Office Action issued on Jul. 31, 2018 during the prosecution of Taiwanese Patent Application No. 106142955.
Notification of Reasons for Refusal issued on Mar. 9, 2017 during the prosecution of Japanese Patent Application No. 2016-240080.
International Search Report mailed Jun. 5, 2018 during the prosecution of International Patent Application No. PCT/JP2018/014910.
Notification of Reasons for Refusal issued on May 29, 2018 during the prosecution of Japanese Patent Application No. 2018-070798.
Specification, DNA RNA Synthesizer Column, Nihon Techno Service Co., Lid.
AKTA Oligopilot Plus Operating Instructions, excerpt p. 52.
Data file, "Fineline Pilot 35 column," Amersham Biosciences, 18-1104-95, 2002-12, p. 1.
Notification of Reasons for Refusal issued on May 29, 2018 during the prosecution of Japanese Patent Application No. 2018-070799.
Notification of Reasons for Refusal issued on Nov. 14, 2017 during the prosecution of Japanese Patent Application No. 2017-119846.
The First Office Action and Search Report issued in corresponding Chinese Patent Application No. 201880033860.0 dated Feb. 2, 2021, with machine translation of Office Action.
Extended European Search Report issued in corresponding European Patent Application No. 18 180 5308 dated Dec. 23, 2020.
Examination report under sections 12 & 13 of the Patents Act, 1970 and the Patents Rules, 2003. issued in Indian Patent Application No. 201947050673 dated Jun. 30, 2021.
Chinese Office Action issued in CN201880033860.1 dated Sep. 15, 2021.
Final rejection dated Mar. 3, 2022 in corresponding Chinese Application No. 201880033860.1.
Substantive Examination-Adverse Report issued on Jul. 1, 2022.
Hearing Notice dated Dec. 14, 2023, from corresponding Indian Application No. 201947050673.
Office Action dated Nov. 2, 2023, from corresponding Canadian Application No. 3064356.
Office Action dated Dec. 18, 2024, from corresponding Canadian Application No. 3064356.

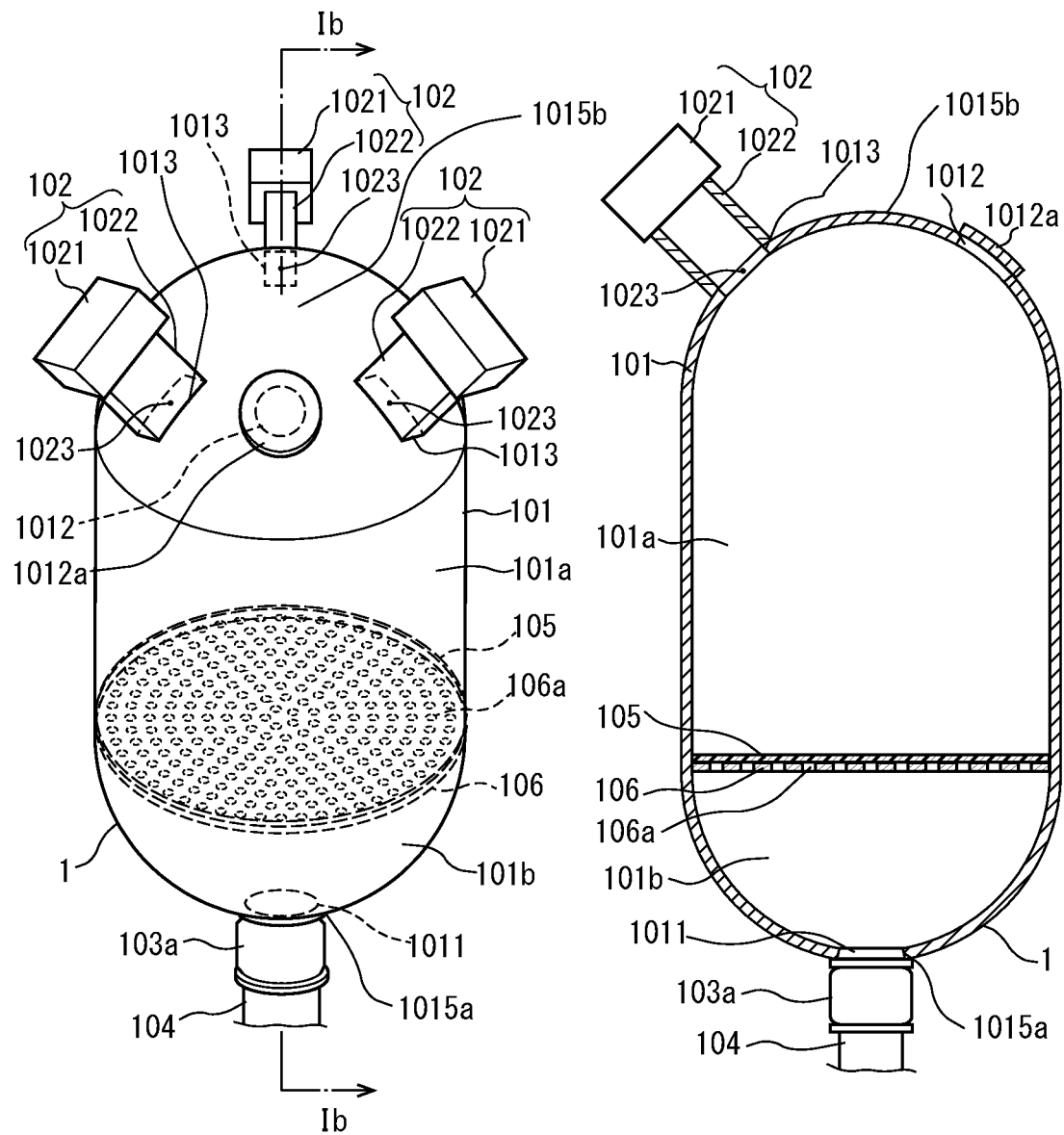
FIG.1A  FIG.1B

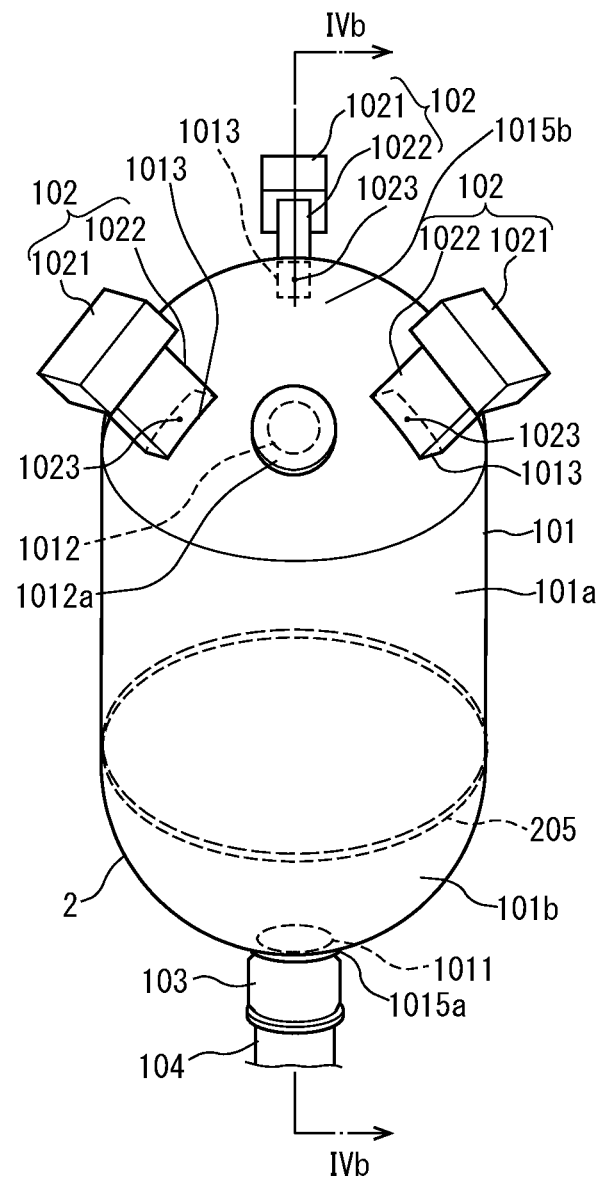
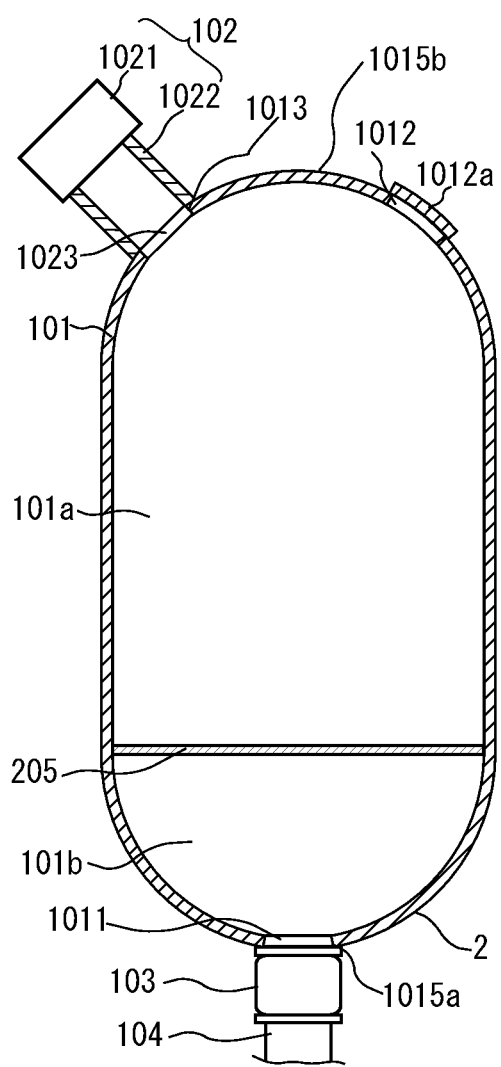
FIG.4A  FIG.4B

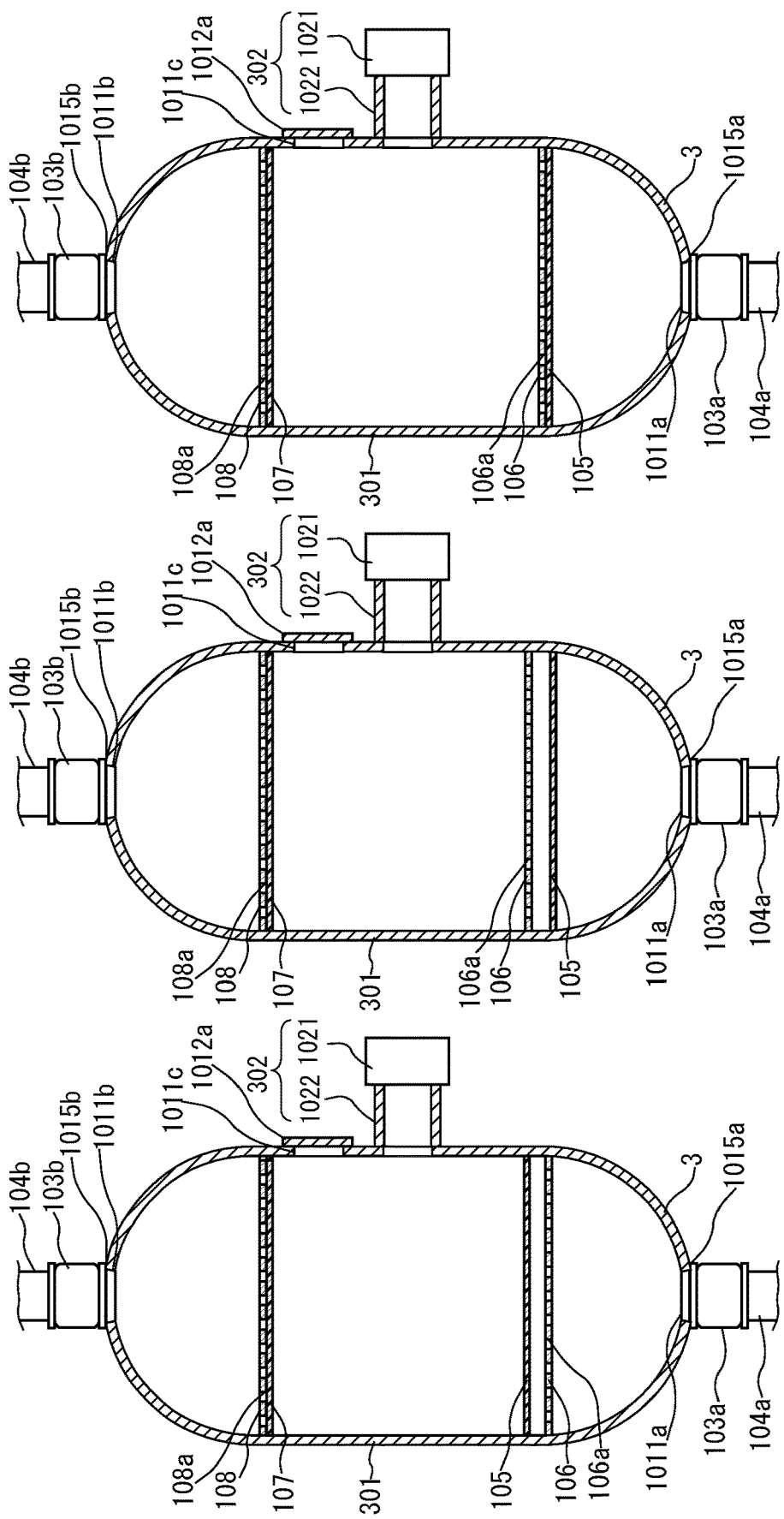

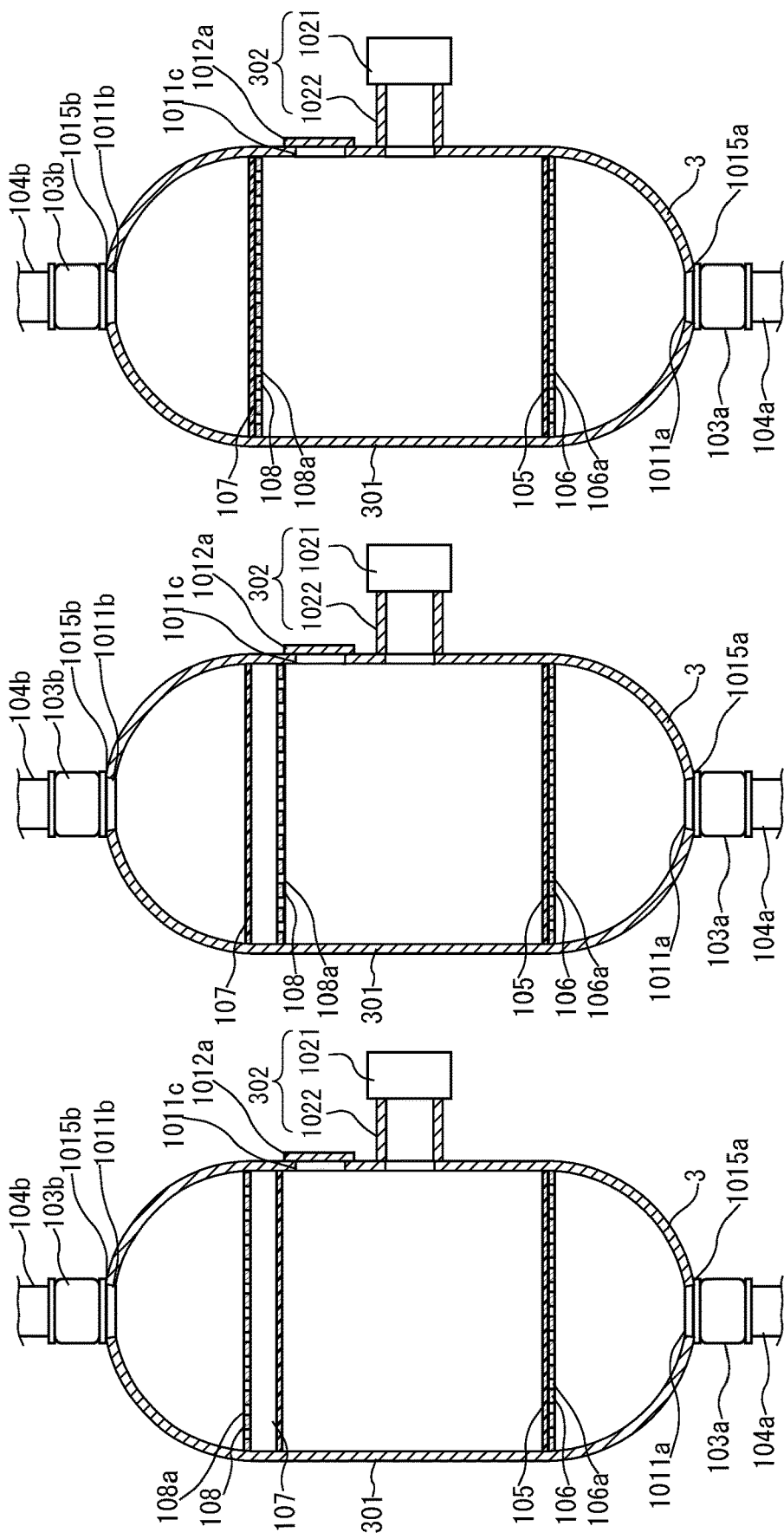

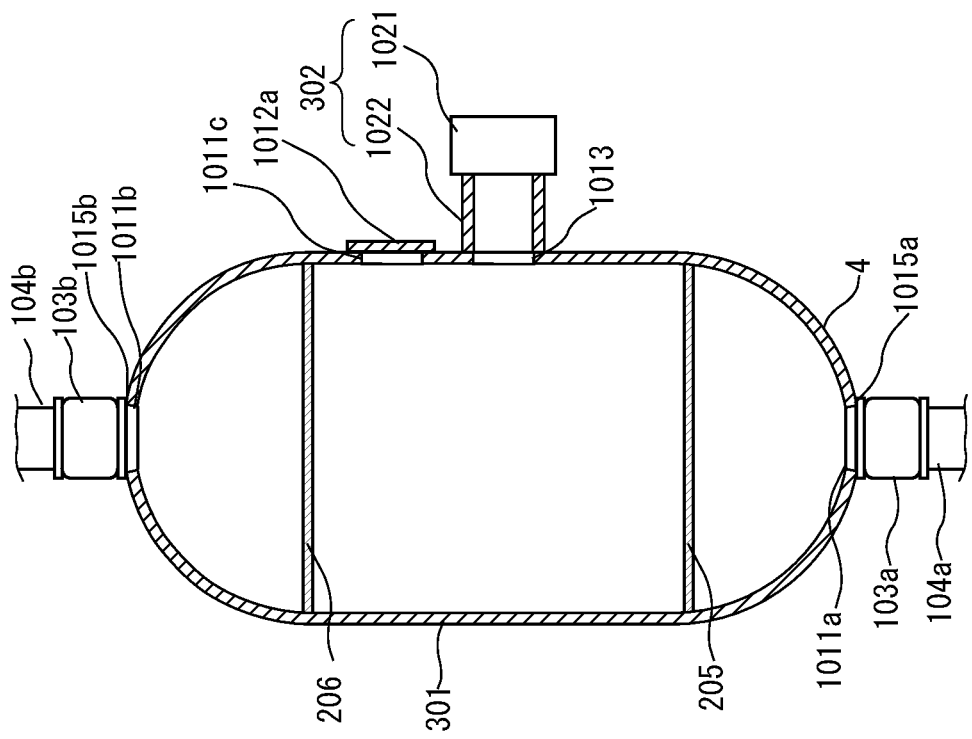
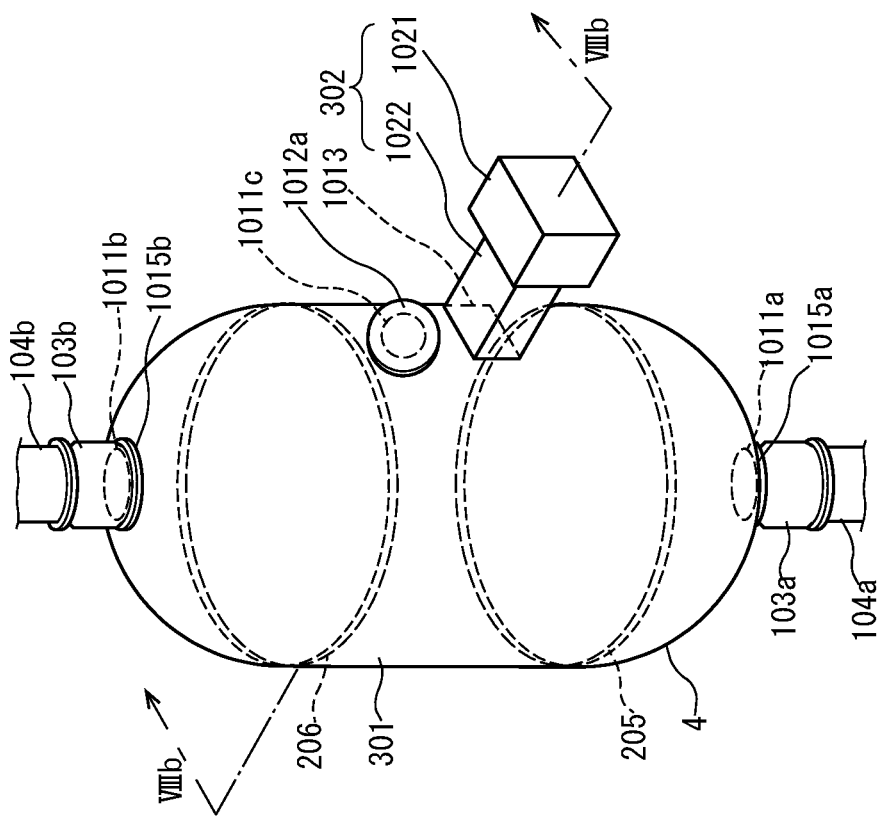
FIG.8A
FIG.8B

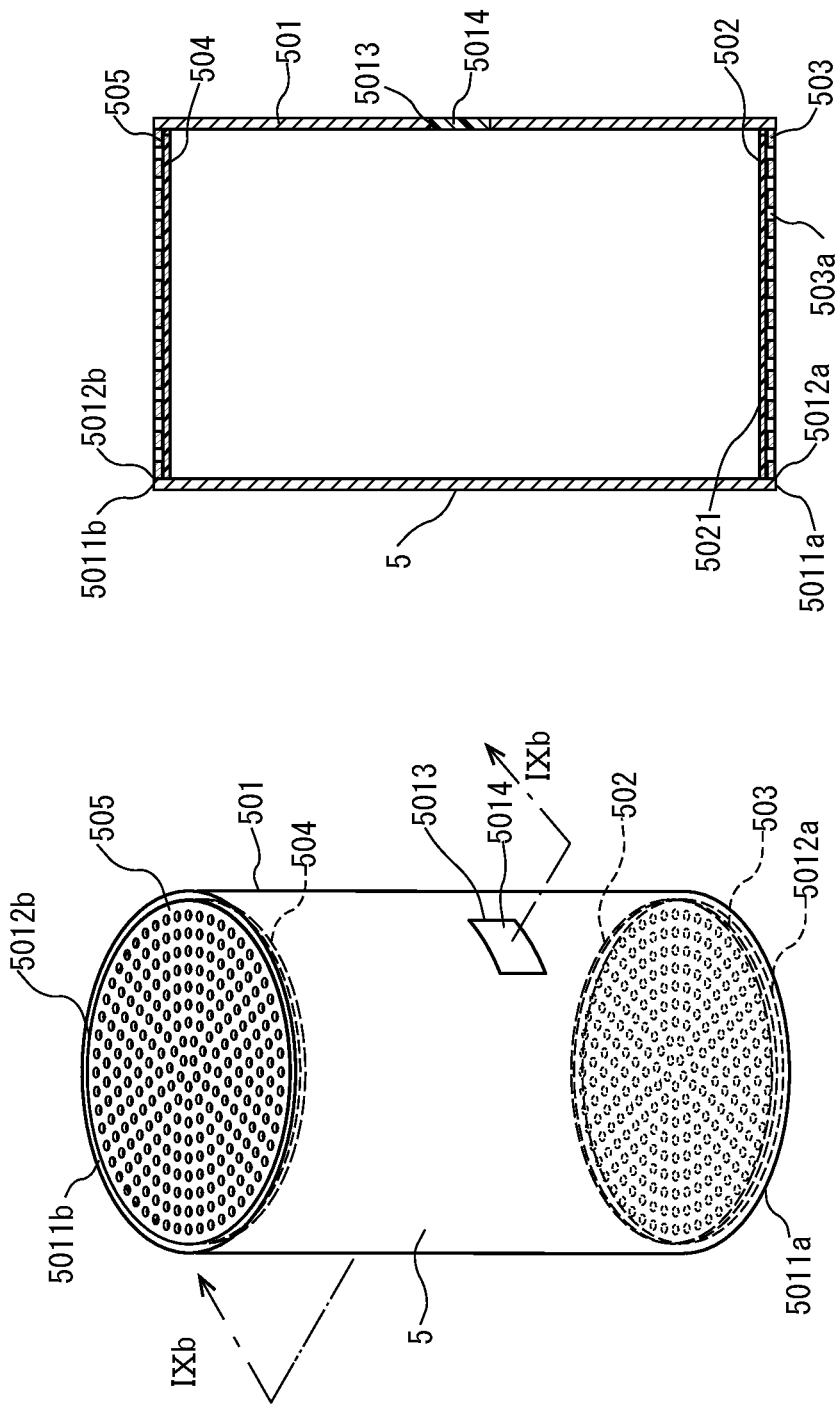

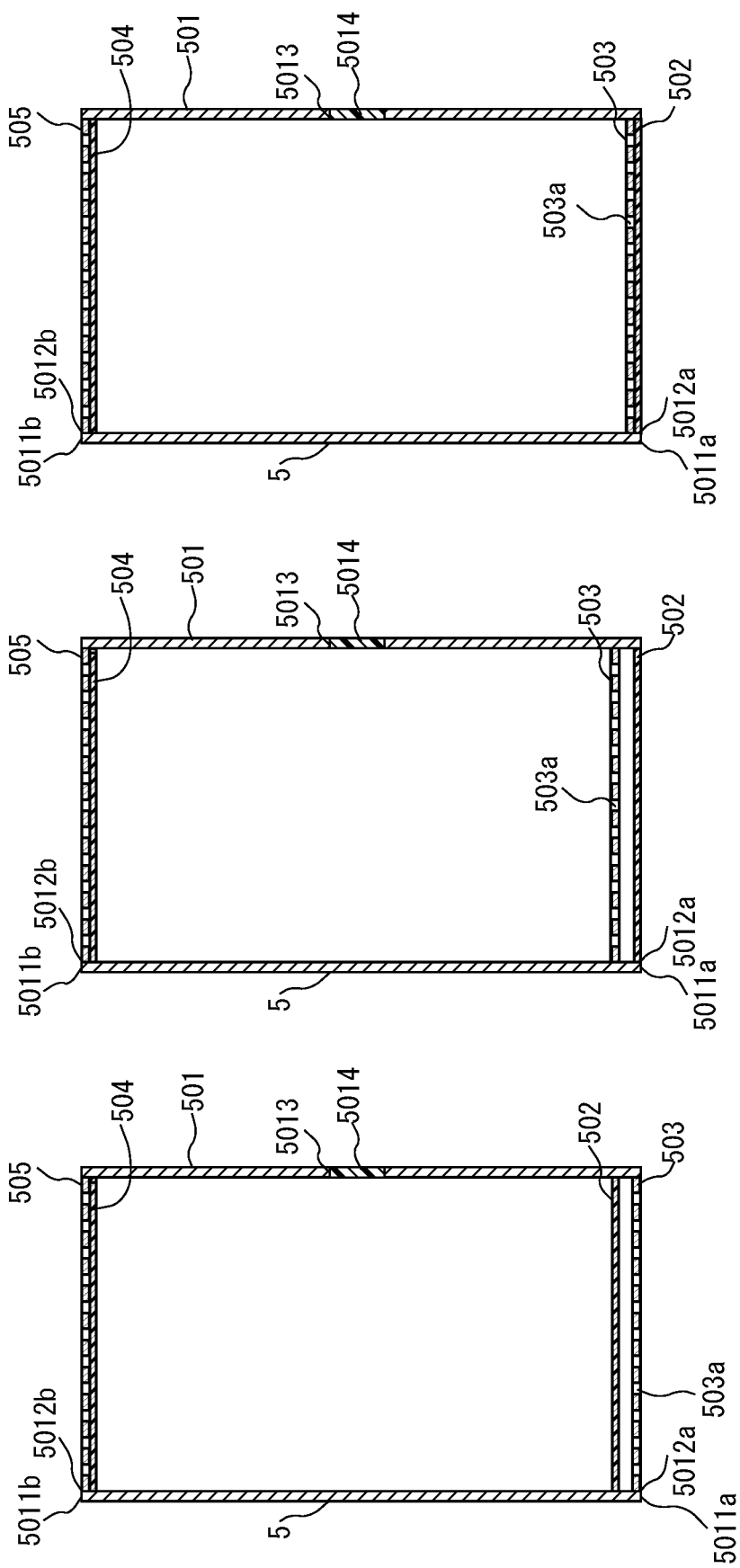

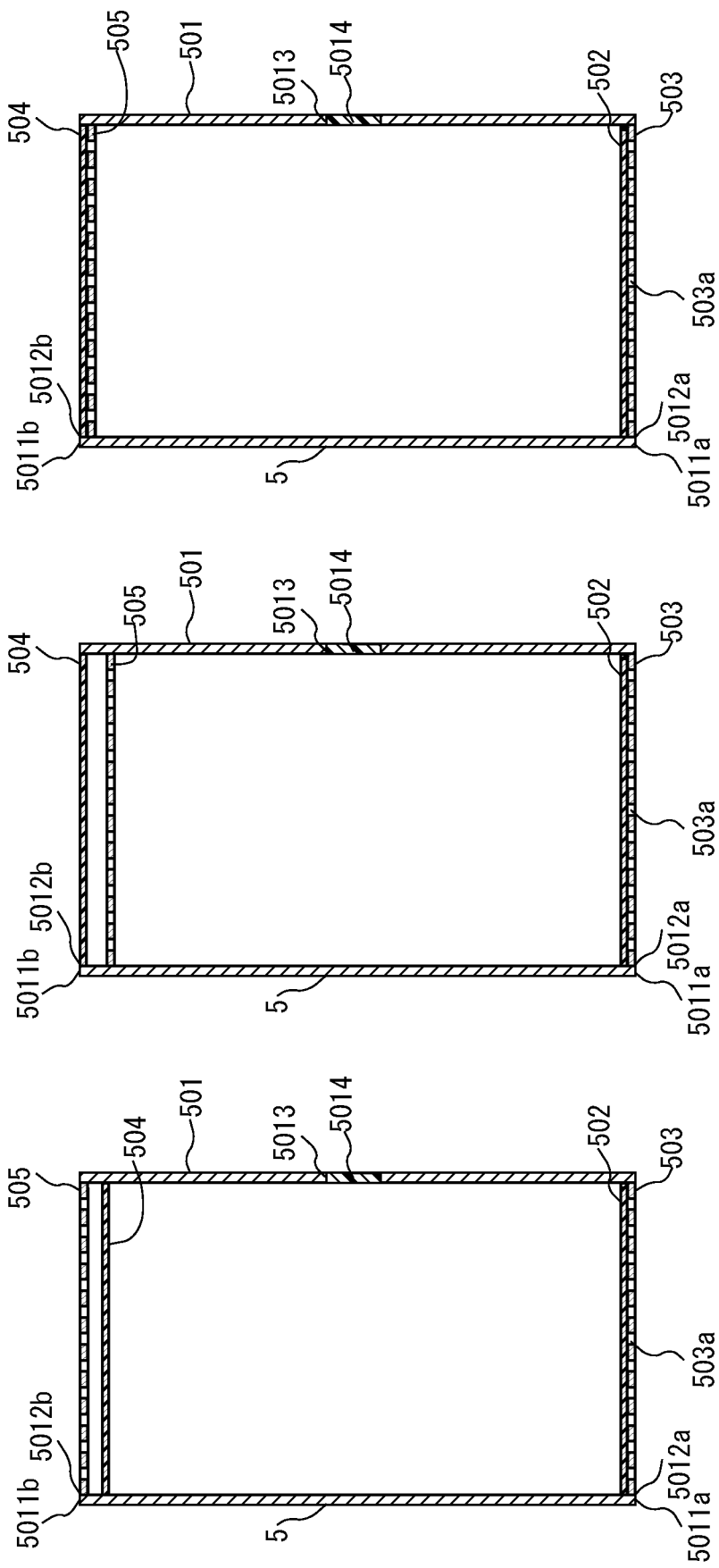

TREATMENT APPARATUS

CROSS-REFERENCE TO RELATED APPLICATIONS

This application is a continuation application of U.S. patent application Ser. No. 16/306,216 filed Nov. 30, 2018, which is a U.S. national phase application under U.S.C. § 371 of International Patent Application No. PCT/JP2018/014910, filed Apr. 9, 2018, and claims benefit of priority to Japanese Patent Application 2017-101859, filed May 23, 2017, Japanese Patent Application 2017-119846, filed Jun. 19, 2017, Japanese Patent Application 2018-033004, filed Feb. 27, 2018, Japanese Patent Application 2018-070798, filed Apr. 2, 2018 and Japanese Patent Application 2018-070799, filed Apr. 2, 2018. The entire contents of these applications are hereby incorporated by reference.

FIELD OF TECHNOLOGY

The present invention relates to a treatment apparatus used for treatment such as solid-phase synthesis.

BACKGROUND

As a conventional technique, there is a known apparatus used for solid-phase synthesis of peptides, comprising: a reaction cell that is transparent to microwave irradiation; a passageway for adding liquids to the reaction cell; a passageway for removing liquids but not solids from the reaction cell; a microwave cavity for holding the cell; and a microwave source in wave communication with the cavity (see JP 2005-15483A, p. 1, FIG. 1, etc., for example).

SUMMARY

However, in apparatuses that perform microwave irradiation so as to generate single-mode microwaves from the outside of a microwave-transmitting reaction cell as in this sort of conventional apparatuses used for solid-phase synthesis of peptides, a location on which single-mode microwaves are concentrated is very narrow, and thus it is difficult to efficiently perform microwave irradiation. For example, it is not possible to uniformly perform microwave irradiation in a vessel such as a reaction cell and perform treatment at various locations in the vessel, and thus it is difficult to efficiently perform treatment. Accordingly, for example, even if the size of a reaction cell of conventional apparatuses is merely increased, the location irradiated with microwaves is limited, and thus it is difficult to increase the throughput.

Furthermore, in this sort of conventional apparatuses, a reaction cell that is transparent to microwave irradiation is used as a vessel for solid-phase synthesis treatment, and thus microwaves in the irradiation into the reaction cell are transmitted out of the reaction cell via its side face, upper portion, bottom face, or the like. Accordingly, microwaves in the irradiation are unlikely to be confined inside the reaction cell, and thus it is not possible to efficiently perform microwave irradiation in the vessel.

Furthermore, a similar problem arises also in the case in which this sort of apparatuses are applied to treatment using microwaves other than the solid-phase synthesis of peptides.

In this manner, conventional techniques are problematic in that it is not possible to efficiently perform microwave irradiation.

The present invention was arrived at in order to solve the above-described problems, and it is an object thereof to provide a treatment apparatus that can efficiently perform microwave irradiation.

The present invention is directed to a treatment apparatus including: a vessel made of a microwave-reflecting material, and having a first end and an emitting portion of microwaves that are emitted into the vessel; a first filter located so as to partition the vessel, and configured to separate solids that are to be separated, from contents of the vessel; and a first reflecting member located closer to the first end than the emitting position is and so as to partition the vessel, and configured to allow at least contents having passed through the first filter to pass through the first reflecting member, and to reflect microwaves.

With this configuration, it is possible to efficiently perform microwave irradiation. Since the first reflecting member reflects microwaves, the region that is closer to the first end than the first filter for separating solids that are to be separated is and that is closer to the first end than the first reflecting member is can be made unlikely to be irradiated with microwaves, and the regions such as a region in which solids cannot be separated and a region in which solids do not exist can be made unlikely to be irradiated with microwaves. Accordingly, it is possible to efficiently perform microwave irradiation.

Furthermore, in the treatment apparatus of the present invention, the first reflecting member is located closer to the first end than the first filter is, or between the first filter and the emitting portion.

With this configuration, the region that is closer to the first end than the first reflecting member is, in the regions such as a region in which solid-phase resins or solids cannot be separated and a region in which solids do not exist on the first end side can be made unlikely to be irradiated with microwaves. Accordingly, it is possible to efficiently perform microwave irradiation.

Furthermore, in the treatment apparatus of the present invention, the first filter and the first reflecting member are laid over each other.

With this configuration, the first filter can be reinforced by the first reflecting member. Accordingly, for example, it is possible to widen the range of choice of the filter.

Furthermore, in the treatment apparatus of the present invention, the first reflecting member is located between the first filter and the emitting portion, and configured to allow the solids to pass through the first reflecting member.

With this configuration, the region that is closer to the first end than the first reflecting member is can be made unlikely to be irradiated with microwaves. Accordingly, it is possible to efficiently perform microwave irradiation.

Furthermore, in the treatment apparatus of the present invention, the first filter and the first reflecting member together configure a first reflecting filter that separates solids that are to be separated, from contents of the vessel, and that reflects microwaves.

With this configuration, the region that is closer to the first end than the first reflecting filter, which is a region in which solids cannot be separated and a region in which solids do not exist, is can be made unlikely to be irradiated with microwaves. Accordingly, it is possible to efficiently perform microwave irradiation. Since the first filter and the first reflecting member together configure one member, the handling is easy.

Furthermore, in the treatment apparatus of the present invention, the vessel further has a second end, the emitting portion is provided between the first end and the second end of the vessel, and the treatment apparatus further includes: a second filter located closer to the second end than the first filter and the first reflecting member are and so as to partition the vessel, and configured to separate solids that are to be separated, from contents of the vessel; and a second reflecting member located closer to the second end than the first filter and the emitting portion are and so as to partition the vessel, and configured to allow at least contents having passed through the second filter to pass through the second reflecting member, and to reflect microwaves.

With this configuration, since the first reflecting member and the second reflecting member reflect microwaves, the region that is closer to the first end than the first filter for separating solids that are to be separated is and that is closer to the first end than the first reflecting member is, and the region that is closer to the second end than the second filter for separating solids that are to be separated is and that is closer to the second end than the second reflecting member is can be made unlikely to be irradiated with microwaves, and the regions such as a region in which solids cannot be separated and a region in which solids do not exist can be made unlikely to be irradiated with microwaves. Accordingly, it is possible to efficiently perform microwave irradiation.

Furthermore, in the treatment apparatus of the present invention, the second reflecting member is located closer to the second end than the second filter is, or between the second filter and the emitting portion.

With this configuration, the region that is closer to the second end than the second reflecting member is, in the regions such as a region in which solid-phase resins or solids cannot be separated and a region in which solids do not exist on the second end side can be made unlikely to be irradiated with microwaves. Accordingly, it is possible to efficiently perform microwave irradiation.

Furthermore, in the treatment apparatus of the present invention, the second filter is laid over the second reflecting member.

With this configuration, the second filter can be reinforced by the second reflecting member. Accordingly, for example, it is possible to widen the range of choice of the second filter.

Furthermore, in the treatment apparatus of the present invention, the second reflecting member is located between the second filter and the emitting portion, and configured to allow the solids to pass through the second reflecting member.

With this configuration, the region that is closer to the second end than the second reflecting member is can be made unlikely to be irradiated with microwaves. Accordingly, it is possible to efficiently perform microwave irradiation.

Furthermore, in the treatment apparatus of the present invention, the second filter and the second reflecting member together configure a second reflecting filter that separates solids that are to be separated, from contents of the vessel, and that reflects microwaves.

With this configuration, the region that is closer to the second end than the second reflecting filter, which is a region in which solids cannot be separated and a region in which solids do not exist, is can be made unlikely to be irradiated with microwaves. Accordingly, it is possible to efficiently perform microwave irradiation. Since the second filter and the second reflecting member together configure one member, the handling is easy.

Furthermore, in the treatment apparatus of the present invention, in the vessel, a first opening portion through which at least one of supply and discharge of contents is performed is located closer to the first end than the first filter and the first reflecting member are.

With this configuration, it is possible to supply the contents into the vessel and discharge the contents from the vessel via the first opening portion.

Furthermore, in the treatment apparatus of the present invention, in the vessel, a first opening portion through which at least one of supply and discharge of contents is performed is located closer to the first end than the first filter and the first reflecting member are, and a second opening portion through which at least one of supply and discharge of contents is performed is located closer to the second end than the second filter and the second reflecting member are.

With this configuration, it is possible to supply the contents into the vessel and discharge the contents from the vessel via the first opening portion and the second opening portion.

Furthermore, in the treatment apparatus of the present invention, the first end is a lower end of the vessel, and the first opening portion is a discharge port for discharging contents.

With this configuration, it is possible to discharge the contents from the vessel via the first opening portion.

Furthermore, in the treatment apparatus of the present invention, microwave irradiation from the emitting portion is performed between the first opening portion and the second opening portion in a state in which contents flow inside the vessel.

With this configuration, it is possible to perform treatment in a state in which contents flow inside the vessel, and, for example, it is possible to perform treatment or the like in a state in which materials or the like used for a reaction continuously flow.

Furthermore, the treatment apparatus of the present invention is for performing: treatment that is performed inside the vessel while supplying contents from the first opening portion and discharging the contents from the second opening portion; and treatment that is performed inside the vessel while supplying contents from the second opening portion and discharging the contents from the first opening portion.

With this configuration, the direction in which contents are supplied into the vessel can be changed, and thus it is possible to perform proper treatment. For example, the direction in which contents are supplied can be changed according to the treatment.

Furthermore, in the treatment apparatus of the present invention, the vessel is a cylindrical member having a first end that is open and a second end that is open, the emitting portion of the vessel is provided on a side face of the cylindrical member, the first filter is located so as to obstruct a first end side of the cylindrical member, the first reflecting member is located so as to obstruct a first end side of the cylindrical member, the second filter is located so as to obstruct a second end side of the cylindrical member, and the second reflecting member is located so as to obstruct a second end side of the cylindrical member.

With this configuration, since microwaves introduced from the emitting portion can be reflected by the side face of the cylindrical member, the first reflecting member, and the second reflecting member, it is possible to efficiently perform microwave irradiation. The first filter and the second filter can prevent solids, among the contents, from being discharged to the outside. Accordingly, it is possible to supply and discharge contents properly from the first end and the second end.

Furthermore, in the treatment apparatus of the present invention, the treatment apparatus is a column.

With this configuration, it is possible to efficiently perform microwave irradiation inside the column.

Furthermore, in the treatment apparatus of the present invention, the treatment apparatus is a treatment apparatus used for solid-phase synthesis, and the solids are a solid-phase synthesis carrier used for solid-phase synthesis.

With this configuration, it is possible to efficiently perform microwave irradiation, and to efficiently perform solid-phase synthesis.

Furthermore, in the treatment apparatus of the present invention, the solid-phase synthesis is solid-phase synthesis for synthesizing a peptide or a nucleotide chain bound to a solid-phase synthesis carrier.

With this configuration, it is possible to efficiently perform microwave irradiation, and to efficiently perform solid-phase synthesis of peptides or nucleotide chains.

Furthermore, in the treatment apparatus of the present invention, the treatment apparatus is a treatment apparatus in which microwave irradiation is performed in a multi-mode.

With this configuration, it is possible to efficiently perform microwave irradiation compared with the case in which microwaves in a single-mode are used.

Furthermore, in the treatment apparatus of the present invention, the treatment apparatus further includes an irradiation unit configured to perform microwave irradiation from the emitting portion into the vessel.

With this configuration, it is possible to efficiently perform microwave irradiation.

According to the treatment apparatus of the present invention, it is possible to efficiently perform microwave irradiation.

BRIEF DESCRIPTION OF DRAWINGS

FIG. 1 shows a perspective view showing an example of a treatment apparatus according to Embodiment 1 of the present invention (FIG. 1A), and a cross-sectional view thereof taken along the line Ib-Ib (FIG. 1B).

FIG. 4 shows a perspective view showing an example of a treatment apparatus according to Embodiment 2 of the present invention (FIG. 4A), and a cross-sectional view thereof taken along the line IVb-IVb (FIG. 4B).

FIG. 6 shows cross-sectional views illustrating a first modified example of the treatment apparatus (FIGS. 6A to 6C).

FIG. 7 shows cross-sectional views illustrating a second modified example of the treatment apparatus (FIGS. 7A to 7C).

FIG. 8 shows a perspective view showing an example of a treatment apparatus according to Embodiment 4 of the present invention (FIG. 8A), and a cross-sectional view thereof taken along the line VIIIb-VIIIb (FIG. 8B).

FIG. 9 shows a perspective view showing an example of a column according to in Embodiment 5 of the present invention (FIG. 9A), and a cross-sectional view thereof taken along the line IXb-IXb (FIG. 9B).

FIG. 12 shows cross-sectional views illustrating a first modified example of the column (FIGS. 12A to 12C).

FIG. 13 shows cross-sectional views illustrating a second modified example of the column (FIGS. 13A to 13C).

DETAILED DESCRIPTION

Figure 2A:
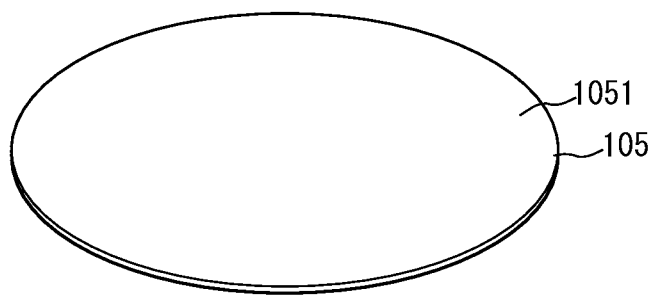
FIG. 2 shows a perspective view of a filter of the treatment apparatus viewed obliquely from above (FIG. 2A), a perspective view of a reflecting member viewed obliquely from above (FIG. 2B), a perspective view of the reflecting member and the filter that is located on the reflecting member viewed obliquely from above (FIG. 2C), and a perspective view of the reflecting member and the filter that is located on the reflecting member viewed obliquely from below (FIG. 2D).

Hereinafter, embodiments of a treatment apparatus and the like will be described with reference to the drawings. It should be noted that constituent elements denoted by the same reference numerals in the embodiments perform similar operations, and thus a description thereof may not be repeated.

Embodiment 1

FIG. 1 shows a perspective view showing an example of a treatment apparatus in this embodiment (FIG. 1A), and a cross-sectional view thereof taken along the line Ib-Ib (FIG. 1B). In FIG. 1B, a cross-section of valves and the like have been omitted.

Figure 2B:
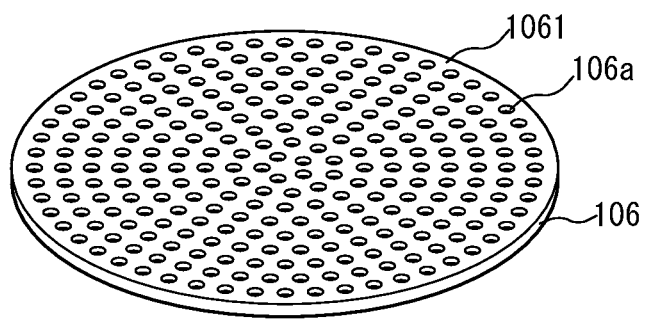
Figure 2C:
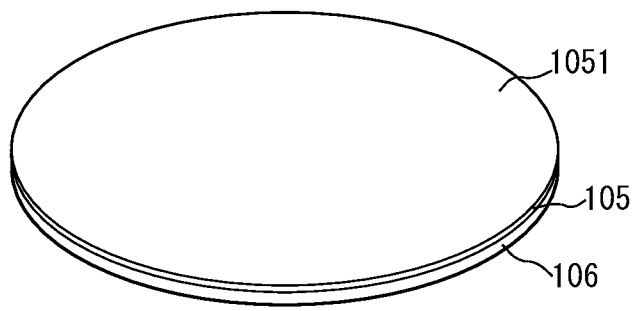
Figure 2D:
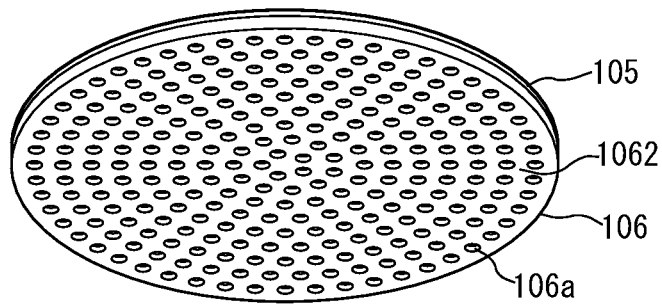

FIG. 2 shows a perspective view of a first filter of the treatment apparatus in this embodiment viewed obliquely from above (FIG. 2A), a perspective view of a first reflecting member viewed obliquely from above, (FIG. 2B), a perspective view of the first reflecting member and the first filter that is located on the first reflecting member viewed obliquely from above (FIG. 2C), and a perspective view of the reflecting member and the filter that is located on the reflecting member viewed obliquely from below (FIG. 2D).

A treatment apparatus 1 includes a vessel 101, irradiation units 102, a first valve 103a, a first filter 105, and a first reflecting member 106. The vessel 101 has a first opening portion 1011, a second opening portion 1012, and irradiation opening portions 1013.

In this embodiment, a case will be described as an example in which the treatment apparatus 1 is a treatment apparatus used for solid-phase synthesis for synthesizing peptides bound to solid-phase resins. Note that the treatment apparatus 1 may be a treatment apparatus used for treatment other than solid-phase synthesis of peptides, as described later.

Hereinafter, first, an example of solid-phase synthesis of peptides will be briefly described. Note that the solid-phase synthesis performed using the treatment apparatus 1 of this embodiment is not limited to the solid-phase synthesis described below, and also may be other solid-phase synthesis. For example, is may be solid-phase synthesis performed using a substance other than the substance described below.

The solid-phase synthesis of peptides is one of the methods for chemically synthesizing peptides, and is also referred to as a peptide solid-phase synthesis method. In the solid-phase synthesis, peptides bound to solid-phase resins are synthesized using solid-phase resins, by binding desired amino acids to the surface of the solid-phase resins suspended in proper solvent, and further binding desired amino acids sequentially to the amino acids through a condensation reaction, thereby elongating peptide chains. It is possible to obtain target peptides, for example, by separating the peptides bound to the solid-phase resins from the solid-phase resins.

In solid-phase synthesis, synthesis of peptides progresses from the C-terminus side toward the N-terminus side. Thus, synthesis is started, first, by binding a C-terminal amino acid to the surface of the solid-phase resins. After the reaction between the solid-phase surface and the amino acid is ended, the solid-phase resins are washed with solvent, and remaining amino acid and the like are removed. After removal, the protecting group of the amino acid bound to the solid-phase resins is removed (deprotection), and thus an amino group that will serve as a next reaction point again appears on the surface of the solid-phase resins. Further, an amino acid having a protected N-terminus is added, so that the C-terminus side of the amino acid having a protected N-terminus is bound to the N-terminus side of the amino acid that has appeared on the surface of the solid-phase resins, through a condensation reaction. It is possible to precisely synthesize peptides with a target sequence, by repeating this procedure while sequentially changing amino acids that are used.

Hereinafter, an example of materials and the like used for the above-described solid-phase synthesis will be described. Examples of the solid-phase resins include polymers such as polystyrene, polyamide, and the like. Note that the solid-phase resins may be resins other than these. The solid-phase resins are, for example, granular (e.g., bead-like) resins with a diameter of 10 to 1000 μm. Examples of the solvent in which the solid-phase resins are suspended include DMF (N,N-dimethylformamide). Note that other solvents also may be used. The solid-phase resins are used, for example, as a solid-phase synthesis carrier, to which peptides and the like can be bound for synthesis.

It is also possible to indirectly bind a C-terminal amino acid to solid-phase resins via a linker molecule or the like, instead of directly binding a C-terminal amino acid to solid-phase resins. Examples of the linker molecule include 4-(hydroxymethyl)phenoxyacetic acid (HMP), and benzhydrylamine derivatives.

Examples of the protecting groups of amino acids include Boc (t-butoxycarbonyl) and Fmoc (9-fluorenylmethyloxycarbonyl), and the like.

Removal of the protecting groups, that is, deprotection is performed, for example, through base treatment using piperidine or the like as a deprotecting agent.

The treatment that sequentially binds amino acids to solid-phase resins is performed in a solution containing amino acids. For example, the treatment that sequentially binds amino acids to solid-phase resins is performed in a solution containing amino acids, an activator, a racemization inhibitor, and the like. The activator is used to facilitate binding between a deprotected amino acid bound to solid-phase resins (including a terminal amino acid of a peptide bound to the solid-phase resins) and an amino acid having a protected N-terminus in the solution. The activator is also referred to as a condensing agent. The racemization inhibitor is used to, for example, prevent the reactivity from decreasing due to racemization, by inhibiting generation of racemization. Examples of the activator include DIPCI (N,N'-diisopropylcarbodiimide), HBTU (N,N,N',N'-tetramethyl-O-(benzotriazole-1-yl)uronium hexafluorophosphate), and the like. Examples of the racemization inhibitor include Oxyma (ethyl(hydroxyimino)cyanoacetate), and the like.

In various types of treatment performed in solid-phase synthesis, it is possible to facilitate the treatment or increase the treatment speed, by performing microwave irradiation. For example, it is known that, as discovered in JP 2005-15483A and the like, the treatment time can be shortened by facilitating a deprotection process by performing microwave irradiation when removing a protecting group from an N-terminus of an amino acid bound to the solid-phase resins, that is, when performing deprotection. It can be considered that an amino acid bound to the solid-phase resins includes a terminal amino acid of a peptide bound to the solid-phase resins. The same applies to the description below. It is also known that the condensation treatment time can be shortened by performing microwave irradiation when condensing a deprotected amino acid bound to the solid-phase resins and an amino acid in the solution.

The treatment apparatus 1 of this embodiment is an apparatus used to perform one or more of multiple sessions of treatment constituting such solid-phase synthesis. For example, two or more sessions of treatment performed using the treatment apparatus 1 of this embodiment may be two or more continuous sessions of treatment, or may be two or more discontinuous sessions of treatment. One or more sessions of treatment performed using the treatment apparatus 1 of this embodiment may be any treatment of the multiple sessions of treatment of the solid-phase synthesis. One or more sessions of treatment performed using the treatment apparatus 1 of this embodiment are, for example, preferably one or more sessions of treatment including treatment that performs microwave irradiation on a suspension of the solid-phase resins. For example, the one or more sessions of treatment may include treatment that deprotects an amino acid having a protected N-terminus and bound to the solid-phase resins. The one or more sessions of treatment may include treatment that condenses amino acids, by causing a condensation reaction on deprotected amino acids bound to the solid-phase resins. The one or more sessions of treatment performed using the treatment apparatus 1 of this embodiment are preferably one or more sessions of treatment including treatment that separates the solid-phase resins through filtering. The solid-phase resins in this case are, for example, solid-phase resins to which one or more amino acids are coupled. For example, the treatment may be treatment that filters the solid-phase resins from a suspension of the solid-phase resins to which amino acids have been bound, or may be treatment that, after performing deprotection on solid-phase resins to which an amino acid having a protected N-terminus is bound, separates the solid-phase resins from a suspension of the solid-phase resins through filtering. It may be treatment that, after washing the solid-phase resins with a washing liquid (e.g., solvent) or the like, filters the solid-phase resins. One or more sessions of treatment performed in the treatment apparatus 1 of this embodiment may be a combination of two or more of the above-described sessions of treatment. For example, one or more sessions of treatment performed using the treatment apparatus 1 of this embodiment may be repetition of treatment that elongates one peptide chain, constituted by treatment that performs deprotection on solid-phase resins to which an amino acid having a protected N-terminus is bound, treatment that filters and washes the solid-phase resins after deprotection, treatment that condenses an amino acid having a protected N-terminus to a deprotected amino acid in the solid-phase resins after washing, and treatment that filters and washes the solid-phase resins, or the like.

The vessel 101 is a vessel in which one or more sessions of treatment in solid-phase synthesis are performed. For example, substances, intermediate products, solvent, and the like used for solid-phase synthesis are supplied to and held in the vessel 101. Examples of the substances used for solid-phase synthesis include solid-phase resins, amino acids, a deprotecting agent, an activator, a racemization inhibitor, and the like. The solid-phase resins may be, for example, solid-phase resins to which one or more amino acids have been coupled in advance, may be solid-phase resins on which linker molecules and one or more amino acids have been coupled, or may be solid-phase resins to which amino acids are not coupled. The solid-phase resins may be solid-phase resins to which only linker molecules are bound. For example, the vessel 101 holds these substances and intermediate products together with proper solvent. Furthermore, for example, a liquid for washing, a gas for stirring, and the like used for solid-phase synthesis may be supplied from the outside into the vessel 101. It is also possible to continuously perform treatment in a state in which contents flow through the vessel 101, by continuously supplying and discharging the contents to and from the vessel 101.

The vessel 101 is made of a microwave-reflecting material. The microwave-reflecting material is, for example, a conductive substance. Examples of the microwave-reflecting conductive substance include metals such as stainless steel. The vessel 101 is preferably a material with excellent corrosion resistance. For example, the vessel 101 is preferably made of stainless steel. There is no limitation on the thickness of the outer wall and the like of the vessel 101. The inner wall of the vessel 101 may be coated with a material with high microwave transmission, excellent corrosion resistance, and the like, such as polytetrafluoroethylene (PTFE) or glass. For example, the vessel 101 may be a vessel with a double structure in which the inner wall is made of such a material with high microwave transmission, excellent corrosion resistance, and the like, and the outer wall is made of a microwave-reflecting material such as stainless steel.

The vessel 101 preferably has a structure that does not allow microwaves to leak to the outside when microwave irradiation is performed into the vessel 101. For example, the vessel 101 preferably has a structure that can seal the interior portion of the vessel 101 when microwave irradiation is performed.

The vessel 101 has a first end 1015a and a second end 1015b. An end is, for example, a portion or a region located at an end of the vessel 101. The end may be a point, may be a line, or may be a face. The first end 1015a and the second end 1015b are, for example, positioned facing each other. The first end 1015a and the second end 1015b are, for example, portions at both ends in the longitudinal direction of the vessel 101. In this example, a case will be described in which the vessel 101 is a vertical-type vessel. The vertical-type vessel is, for example, a vessel whose longitudinal direction is substantially along the vertical direction. The vessel 101 is in the shape of a capsule in which the upper and lower portions are hemispherical and the middle portion therebetween is cylindrical. Accordingly, in a cross-section obtained by cutting the vessel 101 along the vertical direction, the ends in the longitudinal direction are each in the shape of a semicircle as shown in FIG. 1B. Hereinafter, a case will be described as an example in which the first end 1015a is the lower end of the vessel 101, and the second end 1015b is the upper end. The lower end of the vessel 101 is an end on the lower side of the vessel 101. The lower end may be considered, for example, as a portion that forms the lower face or the bottom of the vessel 101. The upper end of the vessel 101 is an end on the upper side of the vessel 101. The upper end may be considered, for example, as a portion that forms the upper face of the vessel 101. In this example, a case will be described in which the portion on the first end 1015a side (e.g., the lower end) of the vessel 101 has a shape whose size continuously decreases toward the first end 1015a. Also, a case will be described in which the portion on the second end 1015b side (e.g., the upper end) of the vessel 101 has a shape whose size decreases continuously or in a stepwise manner toward the second end 1015b. The size of the portion on the first end 1015a side of the vessel 101, and the size of the portion on the second end 1015b side of the vessel 101 may be considered, for example, as the thickness of the vessel 101, may be considered as the size (e.g., the cross-sectional area, etc.) of a cross-section that is perpendicular to the longitudinal direction of the vessel 101, may be considered as the length in a direction that is perpendicular to the longitudinal direction of the vessel 101, or may be considered as the width of the vessel 101.

The vessel 101 may have any shape, and, for example, may have a shape other than the above-described shape. For example, the shape of the vessel 101 may be a shape other than a capsule shape, and may be, for example, a cylindrical shape, may be a polygonal prism shape, may be a conical shape, or may be a shape obtained by combining these shapes. The shape of the upper end side of the vessel 101 may not be a hemispherical shape, and, for example, may be a flat shape. The vessel 101 preferably has a shape, for example, obtained by rotating a desired shape (e.g., a circular shape, an oval shape, a rounded rectangular shape, etc.) about an axis extending in the vertical direction or the horizontal direction, but may not have such a shape obtained through rotation. The vessel 101 may or may not have a shape plane-symmetric about a face that is perpendicular to the longitudinal direction. The portion on the first end 1015a side (e.g., the lower end) of the vessel 101 preferably has a shape, for example, whose size decreases continuously or in a stepwise manner toward the first end 1015a. The portion on the second end 1015b side (e.g., the upper end) of the vessel 101 preferably has a shape, for example, whose size decreases continuously or in a stepwise manner toward the second end 1015b.

The vessel 101 of this embodiment has a size in which the diameter is 1 m and the height is 2 m, but this size is merely an example, and the size of the vessel 101 may be larger than or smaller than this size, that is, there is no limitation on the size of the vessel 101. There is no limitation on the proportion between the height, the width, and the depth of the vessel 101, and the like.

The shape, the size, and the like of the vessel 101 are determined, for example, according to the distribution of microwaves in the irradiation into the vessel 101. For example, the shape and the size of the vessel 101 are preferably set such that the microwave mode inside the vessel 101 is a multi-mode. The multi-mode of microwaves is, for example, a mode in which there is no stationary waves of microwaves inside the vessel 101.

Although not shown, the outer perimeter of the vessel 101 may be provided with a hot water jacket, a cold water jacket, a heater, or the like for adjusting the temperature of the vessel 101.

The lower portion of the vessel 101 has the first opening portion 1011. The lower portion of the vessel 101 in this case is, for example, the first end 1015a side, that is, the lower end side of the vessel 101. The first opening portion 1011 is located at, for example, the first end 1015a of the vessel 101. The first opening portion 1011 is an opening portion for discharging the contents of the vessel 101, and is a discharge port. The discharge of the contents may not be discharge of all contents. The contents of the vessel 101 are, for example, substances, solvent, a washing liquid (e.g., solvent), and the like used for solid-phase synthesis as described above. The liquid content is a concept that encompasses solutions, suspensions, and the like. The contents that are discharged from the first opening portion 1011, which is a discharge port, are, for example, a portion obtained by filtering through the first filter 105, which will be described later, from the contents held in the vessel 101 before discharge, and are a portion excluding the solid-phase resins that have been separated through filtering from the contents. In this case, an example is shown in which the vessel 101 has one first opening portion 1011, but it may have multiple first opening portions 1011. The first opening portion 1011 is preferably located at the lowermost portion of the vessel 101 such that the contents of the vessel 101 are naturally discharged. The lowermost portion of the vessel 101 is typically the lower end 1015a of the vessel 101. There is no limitation on the size and the shape of the first opening portion 1011.

The size of the first opening portion 1011 is preferably smaller than the size of a portion of the vessel 101 away from the first end 1015a (e.g., a portion near the center in the longitudinal direction of the vessel 101, and a portion provided with the first filter 105 or the first reflecting member 106).

The vessel 101 has the second opening portion 1012 for supplying substances, solvent, a washing liquid, gas, and the like used for solid-phase synthesis into the vessel 101. There is no limitation on the size and the like of the second opening portion 1012. In this case, an example is shown in which the second opening portion 1012 is located at the upper portion of the vessel 101, but the second opening portion 1012 may be located at a position other than the upper portion (e.g., the side portion or the lower portion of the vessel 101, etc.). The second opening portion 1012 is located, for example, closer to the upper side, that is, the second end 1015b than the first opening portion 1011 is. Note that it is preferable that the second opening portion 1012 for supplying solid-phase resins is located at least closer to the upper side than the later-described first filter 105 is such that the solid-phase resins can be supplied to a point above the later-described first filter 105. The upper portion of the vessel 101 in this case is, for example, a portion on the second end 1015b side, that is, the upper end side of the vessel 101. The second opening portion 1012 is preferably an opening portion that can be covered by an unshown cap, stopper, or the like whenever supply is not performed. Above, a case was described as an example in which one second opening portion 1012 is provided, but multiple second opening portions 1012 may be provided. A pipe (not shown) or the like through which the contents that are to be supplied into the vessel 101 are sent to the second opening portion 1012 may be connected to the second opening portion 1012. The second opening portion 1012 may be provided with one or more nozzles (not shown) or the like extending into the vessel 101, for supplying contents and the like into the vessel 101. The nozzles may be detachable. In this example, a case is shown in which the second opening portion 1012 is covered by an openable cover 1012a.

A stirring unit (not shown) for stirring the contents may be provided inside the vessel 101. The stirring unit may be constituted by, for example, a stirring impeller, a rotational shaft attached to the rotational center of the stirring impeller, and a rotating device such as a motor for rotating the rotational shaft. There is no limitation on the number, the shape, and the like of stirring impellers. The direction in which the rotational shaft extends may be the vertical direction, may be the horizontal direction, or may be other directions. The stirring unit may be a unit that stirs the contents with air bubbles (i.e., through bubbling) by blowing air bubbles into the liquid content. The stirring unit may be, for example, a combination of an opening portion or a nozzle provided on a lower portion, a side portion, or the like of the contents and configured to blow inert gas such as nitrogen, and a gas supply unit such as a gas cylinder connected to the opening portion or nozzle via a pipe or the like and configured to supply gas thereto. Instead of inert gas, gas that does not affect or is unlikely to affect the solid-phase synthesis also may be used.

A unit (not shown) such as a temperature sensor for measuring the temperature inside the vessel 101 may be provided inside or outside the vessel 101. It is also possible to perform feedback control of the temperature inside the vessel 101, using the values acquired by the unit for measuring the temperature. Sensors other than the temperature sensor, such as a pressure sensor may be provided inside the vessel 101. The vessel 101 may be provided with an observation window (not shown) for observing the interior portion of the vessel 101. The observation window can be constituted by, for example, a cylindrical member that is made of a material with high microwave reflectance, that has a size that does not allow microwaves inside the vessel 101 to leak, and that is covered by glass or the like. There is no limitation on the structure and the like of the observation window. The vessel 101 may be a vessel whose internal pressure can be changed. For example, the vessel 101 may be a vessel whose internal pressure can be reduced or increased. The vessel 101 may be connected to, for example, a unit (not shown) such as a pump for changing the pressure inside the vessel 101.

The irradiation units 102 perform microwave irradiation into the vessel 101. The irradiation units 102 are, for example, attached to the vessel 101 such that microwave irradiation can be performed into the vessel 101. The irradiation units 102 include three pairs of a microwave oscillator 1021 and a waveguide 1022, and perform microwave irradiation into the vessel 101 from three points. The three waveguides 1022 of the irradiation units 102 are attached to the vessel 101 such that the opening portions respectively at their ends are in communication with the irradiation opening portions 1013, which are opening portions located at three different points on the vessel 101. The irradiation opening portions 1013 are open such that the inside and the outside of the vessel 101 are in communication with each other. The irradiation opening portions 1013 may be considered, for example, as opening portions used to perform microwave irradiation into the vessel 101. The inside of the vessel 101 may be considered as a portion inside the vessel 101 or an interior portion of the vessel 101. The irradiation opening portions 1013 may be considered, for example, as introduction ports for introducing microwaves into the vessel 101, portions for emitting microwaves into the vessel 101, or the like. The ends of the respective waveguide 1022 that are connected to the irradiation opening portions 1013 of the vessel 101 are, for example, the ends of the waveguides 1022 on the side opposite to the ends that are connected to the microwave oscillators 1021. The ends of the respective waveguide 1022 that are connected to the irradiation opening portions 1013 of the vessel 101 are portions from which microwaves are emitted by the irradiation units 102, and the positions to which the ends are connected are, for example, positions from which microwaves are emitted by the irradiation units 102. In this case, for example, the ends of the three waveguides 1022 are connected to positions in the upper portion of the vessel 101 at the same height, and the ends of the three waveguides 1022 are located at equal intervals about the virtual central axis extending in the vertical direction of the vessel 101.

The microwave oscillators 1021 generate microwaves. The microwaves that are generated by the microwave oscillators 1021 are transmitted through the waveguides 1022 respectively connected to the microwave oscillators 1021, and are further transmitted via the irradiation opening portions 1013 and emitted into the vessel 101 from the ends of the respective waveguides 1022 that are connected to the vessel 101. Accordingly, microwaves that are generated by the microwave oscillators 1021 are microwaves that are emitted by the irradiation units 102. There is no limitation on the frequency, the intensity, and the like of microwaves that are emitted by the microwave oscillators 1021. The frequency of microwaves that are emitted by the microwave oscillators 1021 may be, for example, 915 MHz, 2.45 GHz, 5.8 GHz, or other frequencies ranging from 300 MHz to 300 GHz. The microwave oscillators 1021 may be, for example, magnetrons, klystrons, gyrotrons, semiconductor oscillators, or the like.

The waveguides 1022 are used as transmitting portions that transmit microwaves. The waveguides 1022 are typically waveguides with a shape that conforms to the frequency of microwaves that are generated by the microwave oscillators 1021. The irradiation opening portions 1013 connected to the ends of the waveguides 1022 may be covered by a material with high microwave transmission such as a fluorinated polymer (e.g., PTFE), glass, rubber, nylon, or the like. For example, the irradiation opening portions 1013 may be covered by a plate made of such a material or the like. The positions from which microwaves are emitted by the irradiation units 102 into the vessel 101 may be considered, for example, as centers 1023 of the opening portions of the ends of the waveguides 1022 that are connected to the vessel 101. The positions from which microwaves are emitted may be considered as the centers of the irradiation opening portions 1013. The waveguides 1022 may be attached to the vessel 101 such that their ends on the vessel 101 side project into the vessel 101. For example, the ends on the vessel 101 side of the waveguides 1022 may extend through the irradiation opening portions 1013 and project into the vessel 101. The waveguides 1022 may be covered by a material with high microwave transmission such as a fluorinated polymer (e.g., PTFE), glass, rubber, nylon, or the like. For example, the waveguides 1022 may be covered by a plate made of such a material or the like. The positions at which the waveguides 1022 are covered are typically portions on the vessel 101 side (e.g., the ends on the vessel 101 side), but also may be other positions such as portions on the microwave oscillators 1021 side, and there is no limitation on the positions. The irradiation opening portions 1013 also may be covered by a material with high microwave transmission, and, also in this case, the waveguides 1022 may be considered as being covered as a result.

The irradiation units 102 may be units other than those described above, as long as microwave irradiation can be performed into the vessel 101. For example, the irradiation units 102 are not limited to those in which microwave irradiation is performed into the vessel 101 from three points, and may be any units that can perform microwave irradiation into the vessel 101 from one or at least two positions. For example, the irradiation units 102 may include one or at least two pairs of a microwave oscillator 1021 and a waveguide 1022 connected to an irradiation opening portion 1013 located on the vessel 101, and cause microwaves that are generated by the microwave oscillators 1021 to be transmitted via the waveguides 1022 and emitted into the vessel 101.

Furthermore, instead of connecting one waveguide 1022 to one microwave oscillator 1021, it is also possible to connect a waveguide 1022 branching into two or more portions to one microwave oscillator 1021, and connect the ends of the branching waveguide 1022 to different irradiation opening portions 1013 located on the vessel 101 such that microwaves that are generated by the one microwave oscillator 1021 are branched by the waveguide 1022 into multiple portions and emitted into the vessel 101 from multiple positions on the vessel 101.

There is no limitation on the positions from which microwaves are emitted by the irradiation units 102. The positions at which the ends of the one or at least two waveguides 1022 are connected to the vessel 101, that is, the positions at which the irradiation units 102 are connected to the vessel 101 may or may not be an upper portion. For example, the ends of the waveguides 1022 may be connected to a side portion or the like of the vessel 101. The connecting positions are determined according to, for example, the shape of the vessel 101, the height of the contents held in the vessel 101, the wavelength of microwaves that are emitted by the irradiation units 102, or the like. The upper portion of the vessel 101 is, for example, a region having the upper end of the vessel 101. In this embodiment, a case will be described as an example in which the ends of the waveguides 1022 are connected to the upper portion of the vessel 101, and the irradiation units 102 perform microwave irradiation into the vessel 101, for example, from a point above the first opening portion 1011 of the vessel 101.

Furthermore, the irradiation units 102 may further include, for example, antennas (not shown) that are connected to the ends of the waveguides 1022 connected to the vessel 101, or that are connected to the irradiation opening portions 1013 to which the ends are connected. The antennas are for emitting microwaves into the vessel 101, and are installed inside the vessel 101. In this case, the antennas are portions from which microwaves are emitted by the irradiation units 102, and the positions from which microwaves are emitted by the irradiation units 102 may be considered, for example, as positions from which microwaves are emitted by the antennas.

Furthermore, in the irradiation units 102 described above, it is possible to use other transmitting portions such as coaxial cables instead of the waveguides 1022, as transmission lines that transmit microwaves that are generated by the microwave oscillators 1021. For example, it is possible to perform microwave irradiation into the vessel 101 via a coaxial cable, by setting a coaxial cable such that one end thereof is connected to the microwave oscillator 1021 and the other end is inserted into the irradiation opening portion 1013 located on the vessel 101. If microwaves that are generated by the microwave oscillators 1021 can be emitted into the vessel 101 without using transmitting portions such as the waveguides 1022, the transmitting portions may be omitted.

Furthermore, the irradiation units 102 may further include, for example, antennas (not shown) that are connected to the ends of transmitting portions such as coaxial cables, the end being connected to the vessel 101 (or that are connected to the irradiation opening portions 1013 to which the ends are connected). The antennas are for emitting microwaves into the vessel 101, and are installed inside the vessel 101. In this case, the antennas are portions from which microwaves are emitted by the irradiation units 102, and the positions from which microwaves are emitted by the irradiation units 102 may be considered, for example, as positions from which microwaves are emitted by the antennas.

Furthermore, the irradiation units 102 may emit microwaves at different frequencies into the vessel 101. For example, it is possible that the irradiation units 102 include multiple microwave oscillators 1021 that generate microwaves at respectively different frequencies, so that different microwaves are emitted from the microwave oscillators 1021. The irradiation units 102 may simultaneously emit microwaves at different frequencies into the vessel 101, or may emit microwaves at different frequencies at different points in time while switching the microwaves. It is also possible that the irradiation units 102 include one or more microwave oscillators 1021 that can change the frequency of microwaves that are to be emitted, so that microwaves in the irradiation into the vessel 101 can be made microwaves at different frequencies, by changing the frequency of microwaves that are emitted by the microwave oscillators 1021.

The first filter 105 separates the solid-phase resins used for solid-phase synthesis, from the contents of the vessel 101. The solid-phase resins used for solid-phase synthesis in this case may be considered, for example, as solids that are to be separated, in the contents. The first filter 105 separates, for example, substances with a size (e.g., particle size, etc.) smaller than that of the solid-phase resins (e.g., a liquid, solids with a size smaller than that of the solid-phase resins, etc.) and solids with a size equal to or larger than that of the solid-phase resins, from the contents, through filtering. The first filter 105 in this example is made of a microwave-transmitting material. The microwave-transmitting material is, for example, a material with high microwave transmission. The material with high microwave transmission is, for example, a material with a small relative dielectric loss. The microwave-transmitting material is preferably composed of, for example, a chemically inert material with excellent corrosion resistance. For example, the first filter 105 is made of a fluorinated polymer such as PTFE, polypropylene, quartz, glass, nylon, rubber, or the like.

The first filter 105 has, for example, multiple holes for separating the solid-phase resins used for solid-phase synthesis, from the contents of the vessel 101. The holes are, for example, holes formed through the first filter 105 from an upper face 1051 to a back face. The upper face 1051 of the first filter 105 in this example is the face on the second end 1015*b* side of the first filter 105. The first filter 105 is made of, for example, a porous material. The first filter 105 may be a mesh or the like. The contents of the vessel 101 are, for example, a liquid containing solid-phase resins used for performing solid-phase synthesis as described above (e.g., a suspension). This liquid is, for example, a liquid in which an activator, amino acids, and the like used for solid-phase synthesis as described above are dissolved or suspended.

The liquid containing solid-phase resins may be a suspension or the like of the solid-phase resins and a liquid such as solvent for washing the solid-phase resins. The multiple holes of the first filter 105 are, for example, holes with a size that does not allow the solid-phase resins contained in the contents to pass through the first filter 105, and are holes with a size that allows the contents other than the solid-phase resins to pass through the first filter 105. The multiple holes may be, for example, holes with a size that allows all the contents other than the solid-phase resins to pass through the first filter 105, or may be holes with a size that allows part of the contents other than the solid-phase resins to pass through the first filter 105. The contents other than the solid-phase resins are, for example, the solvent, substances such as the activator and the deprotecting agent used for solid-phase synthesis in a state of being dissolved in the solvent, amino acids in a state of being dissolved or suspended in the solvent, or the like, and are contents with a size smaller than that of the solid-phase resins. The multiple holes of the first filter 105 are, for example, holes with a size smaller than that of the solid-phase resins contained in the contents, and larger than that of the contents other than the solid-phase resins. For example, the multiple holes of the first filter 105 are holes with a size smaller than that of the particle size of the solid-phase resins contained in the contents. Accordingly, only the solid-phase resins in the contents of the vessel 101 are separated through filtering, and remain on the upper face 1051 of the first filter 105, whereas substances such as the activator and the deprotecting agent dissolved in the solvent, amino acids dissolved or suspended in the solvent, and the like pass through the holes of the first filter 105 together with the solvent. For example, if granular solid-phase resins with a diameter of 50 to 150 µm are used as the solid-phase resins, each hole of the first filter 105 preferably has a diameter that is smaller than these values, such as less than 50 µm.

The solid-phase resins separated through filtering by the first filter 105 may be only the solid-phase resins, or may be the solid-phase resins to which the linker molecules, one or more amino acids, peptides and the like are bound. For example, the first filter 105 described above may be considered as having multiple holes for separating solid-phase resins to which amino acids and peptide are bound, from the contents of the vessel 101. The solid-phase resins that are separated by the first filter 105 from the contents may be referred to as resin-containing solids, which are solids containing the solid-phase resins, regardless of whether or not the linker molecules, one or more amino acids, peptides and the like are bound thereto. For example, the first filter 105 may be considered as separating the resin-containing solids from the contents of the vessel 101. The same applies to a description of the first reflecting member 106 below. Note that the size of solid-phase resins that can be used is not limited to this.

The first filter 105 is located inside the vessel 101 between the first opening portion 1011 and the positions from which microwaves are emitted by the irradiation units 102, so as to partition the vessel 101. Hereinafter, the positions from which microwaves are emitted by the irradiation units 102 are referred to as emitting positions. The emitting positions may be considered as the centers 1023 of the opening portions of the waveguides 1022 described above. The emitting positions may be considered, for example, as the positions of the irradiation opening portions 1013. The first filter 105 is located between the first opening portion 1011 and the emitting positions so as to partition the vessel into two upper and lower regions. The state in which the first filter 105 is located between the first opening portion 1011 and the emitting positions refers to, for example, a state in which the first filter 105 is located such that the position of the first filter 105 in the longitudinal direction of the vessel 101 is a position that is between the first opening portion 1011 and the emitting positions. The state in which the first filter 105 is located so as to partition the vessel 101 refers to, for example, a state in which the first filter 105 is provided between the two regions defined by the first filter 105 such that the contents of the vessel 101 do not migrate without passing through the first filter 105. In this embodiment, an example is shown in which the first filter 105 is provided such that no gap is formed between the outer perimeter of the first filter 105 and the side face of the vessel 101. For example, if the surface of the first filter 105 is substantially flat, the surface is preferably located perpendicular to the longitudinal direction of the vessel 101. The state in which the first filter 105 is located between the first opening portion 1011 and the emitting positions of the irradiation units 102 so as to partition the vessel 101 refers to, for example, a state in which the first filter 105 is located between the first opening portion 1011 and the emitting positions of the irradiation units 102 and the first filter 105 is located such that the contents of the vessel 101 do not migrate, without passing through the first filter 105, between a region that is closer to the irradiation units 102 than the first filter 105 is and a region that is closer to the first opening portion 1011 than the first filter 105 is.

In this embodiment, a case will be described as an example using a sheet-like first filter 105 made of a PTFE porous material. The first filter 105 has the upper face 1051 that is substantially flat, and is located inside the vessel 101 such that the upper face 1051 is along the horizontal direction. In this embodiment, the first filter 105 is located in this manner, and thus the first filter 105 partitions the vessel 101 into upper and lower portions. The upper face 1051 of the first filter 105 may not be substantially flat, and may be, for example, rough. The first filter 105 may be located such that the upper face 1051 is inclined with respect to the horizontal direction.

In this example, a case is described in which the first filter 105 is in the form of a sheet, but the first filter 105 may be a first filter with a form other than a sheet, such as a flat plate. There is no limitation on the thickness, the strength, and the like of the first filter 105. The first filter 105 preferably has a substantially uniform thickness, and may have a non-uniform thickness.

The first filter 105 is preferably located at a position at a height of ¼ or less of the height of the vessel 101 in order to sufficiently secure a region for solid-phase growth treatment, but the first filter 105 may be located at a position at a height of more than ¼ of the height of the vessel 101.

The first reflecting member 106 is located inside the vessel 101 between the first filter 105 and the first opening portion 1011 so as to partition the vessel 101. The first reflecting member 106 is located away from the first opening portion 1011 in the longitudinal direction (the height direction, in this case) of the vessel 101. In this example, as shown in FIGS. 2C and 2D, the first filter 105 is laid over the first reflecting member 106, that is, the second end 1015b side of the first reflecting member 106. The state of being laid over the first reflecting member 106 refers to, for example, a state of being located on an upper face 1061 that is the face on the second end 1015b side of the first reflecting member 106. In this example, the first reflecting member 106 is a flat plate-like member whose upper face 1061 is substantially flat, and that is located inside the vessel 101 such that the upper face 1061 is along the horizontal direction, wherein the first filter 105 is laid over the upper face 1061. Note that the upper face 1061 of the first reflecting member 106 may not be substantially flat. The first reflecting member 106 may not be located such that the upper face 1061 is along the horizontal direction. The first reflecting member 106 may not be a flat plate-like member. The upper face 1061 of the first reflecting member 106 preferably has a shape that allows the sheet-like flat or plate-like first filter 105 to be stably placed thereon. The configuration in which the first filter 105 is laid over the first reflecting member 106 and the like can be applied to the cases in which other filters and the like are laid over reflecting members and the like.

The first reflecting member 106 is made of stainless steel, which is a microwave-reflecting material. The first reflecting member 106 has multiple holes 106a each in a circular planar shape with a size that allows at least the contents of the vessel 101 having passed through the first filter 105 to pass through the hole 106a. The holes 106a are, for example, holes formed through the first reflecting member 106 from the upper face 1061 to a back face 1062. The diameter of each hole 106a is set to a size that allows at least the contents of the vessel 101 having passed through the first filter 105 to pass through the hole 106a, and that allows microwaves having been emitted by the irradiation units 102 to be reflected. The size that allows at least the contents of the vessel 101 having passed through the first filter 105 to pass through the hole 106a may be, for example, any size that is equal to or larger than the size that allows the contents having passed through the first filter 105, among the contents of the vessel 101, to pass through the hole 106a, and, for example, it may be a size that allows a portion excluding the solid-phase resins separated by the first filter 105, among the contents of the vessel 101, to pass through the hole 106a, or may be a size that allows the contents also including the solid-phase resins to pass through the hole 106a. If the diameter of each hole provided through a plate made of a microwave-reflecting material or the width of the widest portion of each opening of a mesh made of a microwave-reflecting material is smaller than the half-wavelength of microwaves that are emitted by the irradiation units 102, microwaves are reflected by the plate or mesh, and thus it is sufficient that the diameter of each of the multiple holes 106a provided through the first reflecting member 106 is set to, for example, a size that is smaller than the half-wavelength of microwaves that are emitted by the irradiation units 102, and that allows the contents having passed through the first filter 105 to pass through the hole 106a. Each hole 106a of the first reflecting member 106 preferably has, for example, a size that is smaller than the half-wavelength of microwaves that are emitted by the irradiation units 102, and that does not prevent the contents having passed through the first filter 105 from passing through the hole 106a. There is no limitation on the number, location pattern, and the like of the multiple holes 106a. In this embodiment, for example, the first reflecting member 106 is composed of perforated metal made of stainless steel having the multiple holes 106a. In ordinary solid-phase synthesis, solid-phase resins have the largest size in the contents of the vessel 101, and thus, if the solid-phase resins can pass through the first reflecting member 106, the contents other than the solid-phase resins can also pass through the first reflecting member 106. FIGS. 2B and 2D and the like are drawings for illustration, that is, a relationship between the size of the multiple holes provided through the first reflecting member 106 and the size of the first reflecting member 106, the location of the holes 106a, the number of the holes 106a, and the like in these drawings are merely for illustration, and do not necessarily match those of the actual first reflecting member 106.

The reflection of microwaves by the first reflecting member 106 may or may not be reflection of all microwaves that are incident on the first reflecting member 106. For example, part of the incident microwaves may pass through the first reflecting member 106 while the remaining microwaves are reflected, or part of the incident microwaves may be absorbed by the first reflecting member 106.

The first reflecting member 106 may be made of any material and may have any shape and size, as long as microwaves having been emitted by the irradiation units 102 are reflected. For example, the first reflecting member 106 may be made of a microwave-reflecting material other than stainless steel (e.g., a metal other than stainless steel, etc.). The first reflecting member 106 is preferably made of a chemically stable material with excellent corrosion resistance. It is also possible to improve the corrosion resistance without impairing the microwave reflectance, by using a metal as a material for forming the first reflecting member 106, and coating its surface with a microwave-transmitting material with high corrosion resistance, such as PTFE. The planar shape of the multiple holes provided through the first reflecting member 106 may be a shape other than a circular shape described above (e.g., a polygonal shape), as long as the shape has a size that allows microwaves to be reflected. The first reflecting member 106 may be, for example, a member made of a microwave-reflecting material, and having a plate-like shape with multiple holes that do not allow microwaves having been emitted by the irradiation units 102 to pass through the holes.

Furthermore, the first reflecting member 106 may not be a flat plate-like member with such multiple holes, and may have any shape and size, as long as at least the contents of the vessel 101 having passed through the first filter 105 can pass through the first reflecting member 106 and microwaves can be reflected. For example, the first reflecting member 106 may be a mesh or the like made of a microwave-reflecting material having multiple opening portions that are holes with a size that does not allow microwaves to pass through the holes. The first reflecting member 106 may be a member other than those described above, as long as at least the contents having passed through the first filter 105 can pass through the first reflecting member 106 and microwaves can be reflected, and, for example, may be a filter or the like made of a porous metal having holes through which solid-phase resins can pass. If the first filter 105 is reinforced and supported from below by the first reflecting member 106, the first reflecting member 106 is preferably made of a material with high strength such as metal.

The first reflecting member 106 is located so as to partition the vessel 101 into upper and lower portions. The state in which the first reflecting member 106 is located so as to partition the vessel 101 refers to, for example, a state in which the first reflecting member 106 is located inside the vessel 101 such that microwaves having been emitted into the vessel 101 from a point above the first reflecting member 106 are not transmitted to a point below the first reflecting member 106. The state in which the vessel 101 is partitioned into upper and lower portions may be considered, for example, as a state in which the interior portion of the vessel 101 is partitioned into upper and lower regions. For example, in this embodiment, the first reflecting member 106 is located inside the vessel 101 such that the upper face 1061 of the reflecting member 106 is along the horizontal direction, so that the first reflecting member 106 partitions the vessel 101 in the upper-lower direction, and the first reflecting member 106 partitions the interior portion of the vessel 101 into an upper region 101a and a lower region 101b.

In the treatment apparatus 1 of this embodiment, the irradiation units 102 perform microwave irradiation into the vessel 101 made of a microwave-reflecting material, and thus the microwaves can be confined inside the vessel 101, and it is possible to efficiently irradiate the contents with microwaves. The microwaves inside the vessel 101 can be set to a multi-mode, and thus concentration of microwaves on one location can be made unlikely to occur compared with that in a single-mode, and it is possible to irradiate the contents with microwaves more uniformly than in the single-mode. Accordingly, it is possible to irradiate the contents with microwaves efficiently and uniformly even when the size of the vessel 101 is increased. Accordingly, in this embodiment, it is possible to increase the throughput of peptides and the like through solid-phase synthesis, by increasing the size of the vessel 101.

Furthermore, the treatment apparatus 1 of this embodiment includes the first filter 105, and thus the solid-phase resins are separated from the contents that have been supplied to a point above the first filter 105, and remain in the vessel 101. Accordingly, it is possible to wash the solid-phase resins by supplying solvent for washing into the vessel 101 in which the solid-phase resins have been separated, and to perform other treatment constituting solid-phase synthesis, without temporarily taking out the solid-phase resins, by supplying other materials, solvent, solutions, and the like into the vessel 101 in which the solid-phase resins have been separated.

In the case of a large vessel in which a large amount of contents can be treated, the size of a discharge port is often small relative to the size of the entire vessel 101. Accordingly, as in the treatment apparatus 1 of this embodiment, it is often the case that the lower portion that is the portion on the first end 1015a side of the vessel 101 has a shape whose thickness decreases from the upper side, which is the second end 1015b side, toward the first opening portion 1011 that is used as a discharge port, such that the contents are likely to be discharged during discharge. In this case, if the first filter 105 for separating the solid-phase resins is located near the first opening portion 1011 so as to partition the vessel 101 into upper and lower portions, the area of the upper face of the first filter 105 is smaller than that of the case in which the first filter 105 is located away from the first opening portion 1011. If the area of the upper face 1051 of the first filter 105 becomes small in this manner, it is conceivable that the speed of filtering the contents during discharge of the contents decreases, and the holes of the first filter 105 are likely to be obstructed by the solid-phase resins remaining on the first filter 105 after filtering, which further decreases the filtering speed or stops the filtering. Accordingly, it is preferable that, as in this embodiment, the first filter 105 is located away from the first opening portion 1011 in the height direction so as to partition the vessel 101 into upper and lower portions as described above, in order to increase the area of the upper face of the first filter 105.

In the treatment apparatus 1, when the contents containing the solid-phase resins, solvent, and the like used for solid-phase synthesis are supplied to a region above the first filter 105, since the first filter 105 is provided, the contents held in the region above the first filter 105 other than the solid-phase resins are supplied via the first filter 105 to the lower region in the vessel 101, which is a region that is closer to the first end 1015*a* than the first filter 105 is. The region in this case may be considered as a space.

However, in a treatment apparatus as in the treatment apparatus 1 of this embodiment in which the first filter 105 that does not allow the solid-phase resins to pass through the first filter 105 is a microwave-transmitting filter, if the first reflecting member 106 is not provided, microwaves in the irradiation performed from a point above the first filter 105, which is on the second end 1015*b* side, in order to facilitate the solid-phase synthesis treatment are transmitted through the microwave-transmitting first filter 105, and the contents in the region below the first filter 105 are also irradiated with the microwaves. The contents in the region below the first filter 105 do not contain the solid-phase resins, and thus, even when the contents in the region below the first filter 105 are irradiated with microwaves, solid-phase synthesis treatment is not performed, that is, the microwaves do not directly contribute to solid-phase synthesis, and the energy is consumed in vain. Especially when the size of the vessel 101 is increased in order to increase the throughput of solid-phase synthesis, the region below the first filter 105 is likely to increase as well, and thus it is conceivable that microwaves cannot be efficiently used.

On the other hand, in the treatment apparatus 1 of this embodiment, the first reflecting member 106 that reflects microwaves is provided on the lower side, that is, on the first end 1015*a* side of the first filter 105, and thus microwaves in the irradiation performed from a point above the first filter 105 are transmitted through the microwave-transmitting first filter 105, but are reflected by the first reflecting member 106 located therebelow and returned to the region above the first filter 105 holding the contents containing the solid-phase resins. Accordingly, the region below the first filter 105 in which solid-phase synthesis is not performed can be made unlikely to be irradiated with microwaves, and microwaves reflected by the first reflecting member 106 also can be used for solid-phase synthesis, and thus it is possible to efficiently use microwaves for solid-phase synthesis. Especially when the size of the vessel 101 is increased in order to increase the throughput of solid-phase synthesis, the region below the first filter 105 is likely to increase as well, and thus, in the treatment apparatus 1 of this embodiment, it is possible to efficiently perform solid-phase synthesis while suppressing unnecessary energy consumption. The first reflecting member 106 has a shape and a size that allow the contents having passed through the first filter 105 to pass through the first reflecting member 106, and thus the first reflecting member 106 does not impede discharge of the contents and the like.

Furthermore, in the treatment apparatus 1 of this embodiment, the first filter 105 is laid over the first reflecting member 106 made of a reflecting material such as a metal, and thus the first reflecting member 106 can reinforce and support the first filter 105 located on the upper face 1061, which is the face on the second end 1015*b* side, of the first reflecting member 106. Accordingly, for example, the first filter 105, the sheet-like first filter 105, or the like, for which it is difficult to be located alone so as to partition the vessel 101 due to low hardness of the material thereof, can be located so as to partition the interior portion of the vessel 101. Accordingly, it is possible to widen the range of choice of the first filter 105.

Hereinafter, an example of solid-phase synthesis treatment using the treatment apparatus 1 of this embodiment will be described. In this example, treatment that performs deprotection on solid-phase resins to which an amino acid having a protected N-terminus is bound, and further binds an amino acid thereto through a condensation reaction will be described. It will be appreciated that substances used for solid-phase synthesis, the proportions thereof, and the like are merely an example, and substances and the like other than those described herein also may be used. Also, the procedure and the like of treatment performed herein are merely an example, and the treatment may be performed following other procedures. Furthermore, it will be appreciated that, in the vessel 101, solid-phase synthesis treatment other than the treatment described herein also may be performed, and only part of the treatment described herein also may be performed.

First, in a state in which the first valve 103*a* is closed such that the contents are not discharged from the first opening portion 1011, a deprotecting agent such as a piperidine solution in which DMF or the like is used as solvent, and solid-phase resins to which an amino acid having an N-terminus protected by an Fmoc group or the like is bound are supplied into the vessel 101 via the second opening portion 1012 provided above the first filter 105, and then the cover 1012*a* is closed. Then, deprotection is performed by irradiating the contents of the vessel 101 with microwaves at 915 MHz from the irradiation units 102, while stirring the contents with air bubbles by supplying nitrogen gas via an unshown nozzle or the like. Since the vessel 101 is provided with the first filter 105, the deprotecting agent and the solid-phase resins are held in the region above the first filter 105, and only the deprotecting agent is held in the region below the first filter 105 (i.e., the region between the first filter 105 and the first end 1015*a*). Note that the deprotecting agent migrates through the first filter 105 and the first reflecting member 106. The microwaves emitted by the irradiation units 102 are reflected by the first reflecting member 106 to the upper region 101*a* above the first reflecting member 106, and thus the region 101*b* in which the solid-phase resins do not exist below the first reflecting member 106 that is positioned below the first filter 105, that is, a region in which deprotection is unnecessary can be made unlikely to be irradiated with microwaves.

After deprotection is completed, when the first valve 103*a* is opened, the deprotecting agent below the first filter 105, among the contents of the vessel 101, is discharged to the outside via the first opening portion 1011, the first valve 103*a*, and a pipe 104, and the deprotecting agent above the first filter 105 passes through the first filter 105 and the first reflecting member 106 and is then discharged to the outside via the first opening portion 1011, the first valve 103*a*, and the pipe 104. The deprotected solid-phase resins among the contents of the vessel 101 are separated from the deprotecting agent and remain on the upper face 1051 of the first filter 105.

Next, after DMF is supplied from the second opening portion 1012 and held in the vessel 101, the DMF is discharged, and thus the deprotected solid-phase resins remaining on the upper face 1051 of the first filter 105 are washed. The washing is performed multiple times.

Next, in order to bind amino acids to the deprotected solid-phase resins, HBTU, DIPEA, an amino acid for binding whose N-terminus is protected by an Fmoc group, and DMF that is used as solvent are supplied from the second opening portion 1012 into the vessel 101, and thus HBTU, DIPEA, and the amino acid for binding are dissolved in DMF, after which the irradiation units 102 perform microwave irradiation, so that the amino acid having a protected N-terminus is bound to deprotected amino acids bound to the solid-phase resins, through a condensation reaction. As described above, the vessel 101 is provided with the first filter 105, and thus the binding solution in which HBTU, DIPEA, and the amino acid for binding are dissolved in DMF, and the deprotected solid-phase resins are held in the region above the first filter 105, in the upper region 101*a* above the first reflecting member 106, and only the binding solution is held in the region below the first reflecting member 106 and below the first filter 105. Note that the binding solution migrates through the first filter 105 and the first reflecting member 106. The microwaves emitted by the irradiation units 102 are reflected by the first reflecting member 106 to the upper region 101*a* above the first reflecting member 106, and thus the region 101*b* in which the solid-phase resins do not exist below the irradiation units 102, that is, the region in which the treatment for binding amino acids is unnecessary can be made unlikely to be irradiated with microwaves.

After binding of amino acids is ended, when the first valve 103*a* is opened, the binding solution is discharged out of the vessel 101, and the solid-phase resins to which an amino acid having a protected N-terminus is newly bound remain on the upper face 1051 of the first filter 105 without being discharged.

Subsequently, washing using DMF as described above is repeated multiple times.

Accordingly, it is possible to obtain peptides bound to the solid-phase resins on the upper face 1051 of the first filter 105.

Furthermore, in order to bind new amino acids to peptides, a series of treatment composed of the deprotection and the binding of amino acids described above may be repeated.

In order to separate the solid-phase resins from the peptides bound to the solid-phase resins remaining on the upper face 1051 of the first filter 105, for example, the solid-phase resins remaining on the upper face 1051 of the first filter 105 may be treated with trifluoroacetic acid (TFA) and $H_2O$. The separated peptides are collected, for example, through sedimentation with ethyl ether or the like and drying.

As described above, according to this embodiment, microwave irradiation is performed into the microwave-reflecting vessel 101, and thus it is possible to increase the throughput of peptides and the like through solid-phase synthesis, by increasing the size of the vessel 101.

Furthermore, according to this embodiment, the first filter 105 is laid over the first reflecting member 106, and thus the first reflecting member 106 reflects microwaves having been transmitted through the first filter 105. Accordingly, the contents not containing the solid-phase resins below the first filter 105 can be made unlikely to be irradiated with microwaves, and thus it is possible to efficiently use microwaves for solid-phase synthesis treatment.

Furthermore, according to this embodiment, the first filter 105 is laid over the first reflecting member 106, and thus the first filter 105 can be reinforced by the first reflecting member 106. Accordingly, for example, it is possible to widen the range of choice of the first filter 105, by relaxing the limitations on the strength, the hardness, and the like required for the first filter 105.

Modified Examples

Figure 3C:
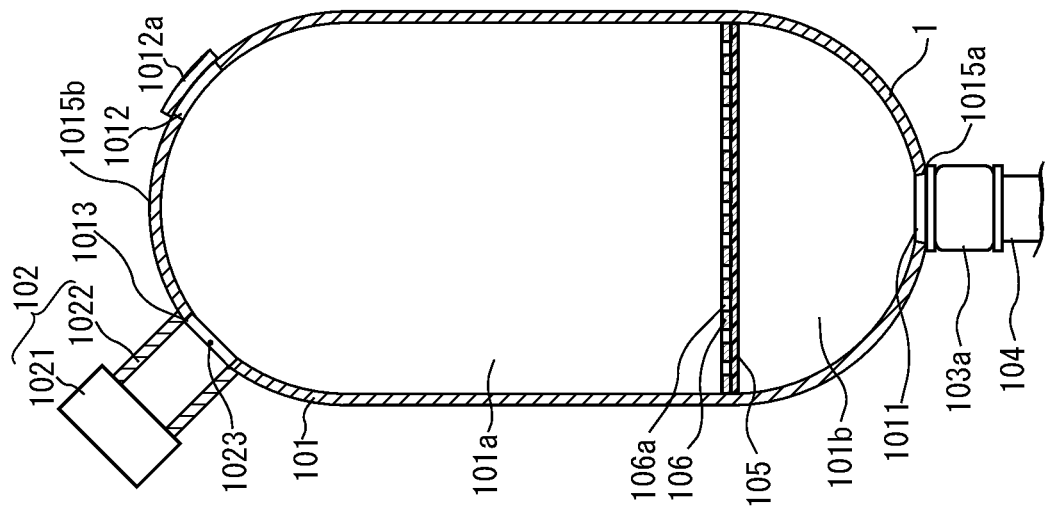
FIG. 3 shows cross-sectional views illustrating modified examples of the treatment apparatus (FIGS. 3A to 3C).
Figure 3B:
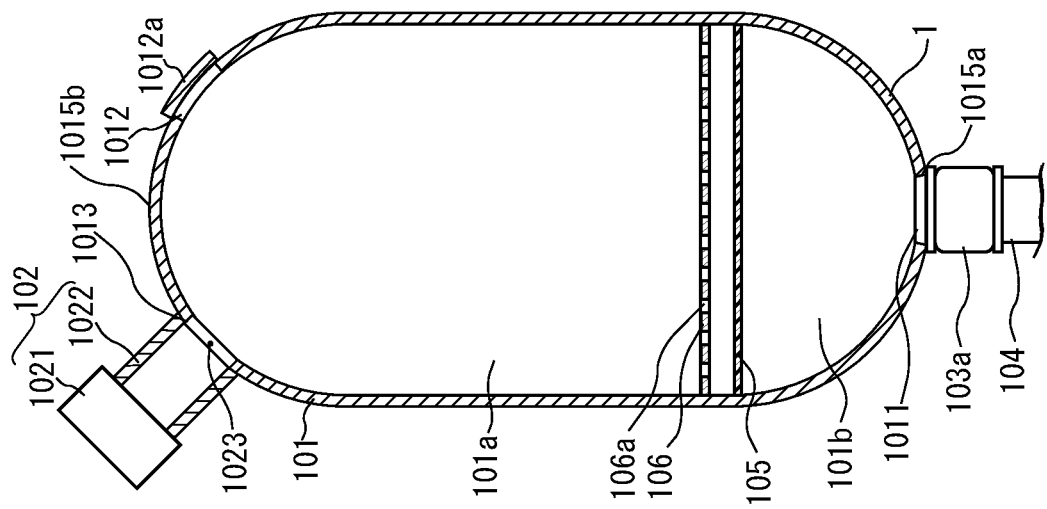
Figure 3A:
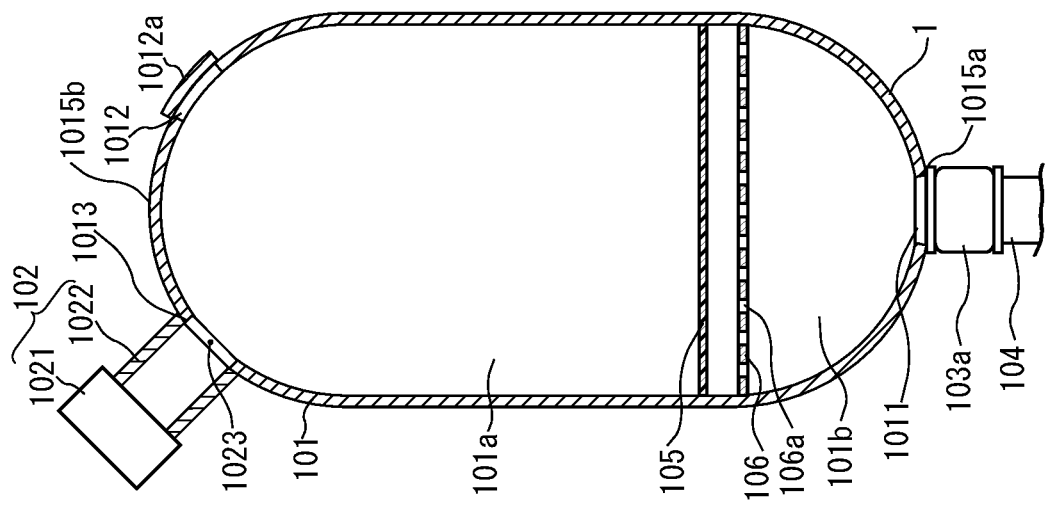

FIGS. 3A to 3C are cross-sectional views illustrating modified examples of the treatment apparatus of this embodiment, and are cross-sectional views corresponding to FIG. 1B.

In the foregoing embodiment, a case was described in which the first filter 105 is laid over the first reflecting member 106, that is, the second end 1015*b* side of the first reflecting member 106, but the first filter 105 may not be directly laid over the first reflecting member 106, as long as the first reflecting member 106 is located between the first filter 105 and the first end 1015*a*, and preferably between the first filter 105 and the first opening portion 1011.

For example, it is also possible to locate the first filter 105 and the first reflecting member 106 such that they are not directly laid over each other as shown in FIG. 3A. Also in this case, microwaves having been transmitted through the first filter 105 are reflected by the first reflecting member 106 located below the first filter 105, so that the region below the first reflecting member 106 is prevented from being irradiated with microwaves, and thus it is possible to efficiently use microwaves for solid-phase synthesis. Note that, in this case, the contents not containing the solid-phase resins between the first filter 105 and the first reflecting member 106 are irradiated with microwaves, and thus it may not be possible to efficiently use microwaves compared with the case in which the first filter 105 is laid over the first reflecting member 106. In this case, the first filter 105 cannot be reinforced by the first reflecting member 106, and thus it is necessary, for example, to use a first filter 105 with sufficient strength even without reinforcement as the first filter 105, or to additionally attach a reinforcing member (e.g., a reinforcing frame, etc.) made of a microwave-transmitting material to the first filter 105, which may lead to the limitation on the material or structure that can be used for the first filter 105, or an increase in the cost and the like because the configuration becomes complex due to the reinforcing member or the like.

Note that the treatment apparatus 1 described with reference to FIGS. 1 and 3A may be considered as an example in which the first reflecting member 106 is provided closer to the first end 1015*a* than the first filter 105 is, and, in particular, may be considered as an example in which the first filter 105 is provided between the microwave emitting positions and the first end 1015*a*, and the first reflecting member 106 is provided closer to the first end 1015*a* than the first filter 105 is.

Furthermore, instead of locating the first reflecting member 106 between the first filter 105 and the first end 1015*a*, and preferably between the first filter 105 and the first opening portion 1011, it is also possible to locate the first reflecting member 106 between the first filter 105 and the microwave emitting positions as shown in FIG. 3B. Also in this case, the first reflecting member 106 reflects microwaves, and thus the region below the first filter 105 can be made unlikely to be irradiated with microwaves, and it is possible to efficiently use microwaves. Note that, in this case, the first reflecting member 106 is a member through which the solid-phase resins can pass such that the solid-phase resins exist in the region above the first filter 105. For example, as the first reflecting member 106, a member having multiple holes with a shape and a size that allow the solid-phase resins to pass through the holes is used. In this case, the contents containing the solid-phase resins between the first reflecting member 106 and the first filter 105 are unlikely to be irradiated with microwaves, and thus, if the distance between the first reflecting member 106 and the first filter 105 increases, the efficiency of the solid-phase synthesis treatment may deteriorate. Furthermore, in this case, the first filter 105 may be made of a material other than microwave-transmitting materials.

Furthermore, as a mode in the case in which the first reflecting member 106 is located between the first filter 105 and the microwave emitting positions, it is also possible to locate the first reflecting member 106 so as to be laid over the upper face of the first filter 105 as shown in FIG. 3C. The state in which the first reflecting member 106 is laid over the upper face of the first filter 105 may be considered as a state in which the first filter 105 is laid over the lower end side of the first reflecting member 106. In this case, it is possible to prevent the efficiency of solid-phase synthesis treatment from deteriorating as described above, by eliminating the distance between the first reflecting member 106 and the first filter 105, and to reinforce the first filter 105 with the first reflecting member 106, by attaching the first filter 105 to the lower face of the first reflecting member 106 with an adhesive or the like or by fastening the first filter 105 to the lower face of the first reflecting member 106 with an unshown fastener, screw, or the like. If the first filter 105 and the first reflecting member 106 are laid over each other as in the foregoing embodiment or FIG. 3C, the first filter 105 can be reinforced by the first reflecting member 106, and thus it is possible to widen the range of choice of the first filter 105. The configuration in which the first filter 105 is fixed to the first reflecting member 106 can be applied, for example, also to the cases in which other filters and the like are fixed to other reflecting members.

The treatment apparatus 1 described with reference to FIGS. 3B and 3C may be considered as an example in which, in the case in which the first filter 105 is provided between the first end 1015a and the microwave emitting positions, the first reflecting member 106 is provided between the first filter 105 and the microwave emitting positions.

As seen from the foregoing embodiment and the modified examples thereof, it is sufficient that the treatment apparatus 1 is configured such that the first opening portion 1011 is located in the lower portion of the vessel 101, the first filter 105 is located between the first opening portion 1011 and the second end 1015b so as to partition the vessel 101 such that solids such as solid-phase resins can be separated from the contents, and the first reflecting member 106 is located between the irradiating position and the first opening portion 1011 so as to partition the vessel 101 such that a region that is closer to the first end 1015a than the first reflecting member 106 is can be made unlikely to be irradiated with microwaves.

Furthermore, as shown in FIGS. 1 and 3, and the like, in the treatment apparatus 1 according to the foregoing embodiment and the modified examples thereof, the first filter 105 is located between the first opening portion 1011 and the microwave emitting positions, and the first reflecting member 106 is located between the first opening portion 1011 and the irradiating position, and thus the first opening portion 1011 of the treatment apparatus 1 may be considered as being located in the vessel 101 at a position that is closer to the first end 1015a than the first filter 105 and the first reflecting member 106 are. The state in which the first opening portion 1011 is provided closer to the first end 1015a than the first filter 105 and the first reflecting member 106 are may be interpreted, for example, as a state in which the first opening portion 1011 is located at a position that is closer to the first end 1015a than the first filter 105 is and that is closer to the first end 1015a than the first reflecting member 106 is. The position that is closer to the first end 1015a than the first filter 105 and the first reflecting member 106 are may be considered, for example, as a position that is closer to the first end 1015a than both the first filter 105 and the first reflecting member 106 are. The same interpretation applies to, for example, the later-described states in which a first opening portion 1011a is provided closer to the first end 1015a than the first filter 105 and the first reflecting member 106 are, in which a second opening portion 1011b is provided closer to the second end 1015b than a second filter 107 and a second reflecting member 108 are, in which a second filter 107 is located closer to the second end than the first filter 105 and the first reflecting member 106 are, in which a second reflecting member 108 is located closer to the second end 1015b than the first filter 105 and the emitting positions are, in which an introduction port 5013 is provided on a side face of a cylindrical member 501 in a region that is closer to a second end 5011b than a first filter 502 and a first reflecting member 503 are, and in which, and an introduction port 5013 is provided in a region that is closer to a first end 5011a than a second filter 504 and a second reflecting member 505 are.

Furthermore, for example, since the first opening portion 1011 may be located at the first end 1015a of the vessel 101 as described above, the treatment apparatus 1 may be such that, for example, the first filter 105 is located between the first end 1015a and the emitting positions so as to partition the vessel 101, the first reflecting member 106 is located between the first end 1015a and the emitting positions so as to partition the vessel 101, and the first opening portion 1011 is provided closer to the first end 1015a than the first filter 105 and the first reflecting member 106 are.

For example, in the case in which the first reflecting member 106 is located closer to the first end 1015a than the first filter 105 is, and the first filter 105 and the first reflecting member 106 are located away from each other as in the modified example shown in FIG. 3A, the irradiation units 102 may perform microwave irradiation into the vessel 101 from a position between the first filter 105 and the first reflecting member 106 of the vessel 101. That is to say, the emitting positions may be set to a position that is between the first filter 105 and the first reflecting member 106 of the vessel 101. In this case, solids such as solid-phase resins that are to be separated are supplied, for example, to the region between the first filter 105 and the second end 1015b, which is above the first filter 105, and the contents are supplied, for example, up to a position that is higher than the first filter 105 in the vessel 101. Also in this configuration, the first filter 105 is located inside the vessel 101 between the first end 1015a and the second end 1015b, and the first reflecting member 106 is located between the first end 1015a and the emitting positions. Also in this configuration, the region below the first reflecting member 106 can be made unlikely to be irradiated with microwaves, and effects similar to those described above are achieved. In this case, if the contents are a liquid, for example, microwave irradiation is performed from the liquid. The position that is between the first filter 105 and the first reflecting member 106 of the vessel 101 is, for example, a point whose position in the height direction of the vessel 101 is between the first filter 105 and the first reflecting member 106. For example, the irradiation opening portions 1013 may be provided at a position that is between the first filter 105 and the first reflecting member 106 of the vessel 101, wherein the irradiation units 102 perform microwave irradiation into the vessel 101 from the irradiation opening portions 1013.

As seen from such a treatment apparatus in which the emitting positions are set to a position that is between the first filter 105 and the first reflecting member 106, and the treatment apparatuses of the foregoing embodiment and the modified examples thereof, it is sufficient that the treatment apparatus 1 is configured such that the first opening portion 1011 is located on the first end 1015a side of the vessel 101, the first filter 105 is located between the first opening portion 1011 and the second end 1015b so as to partition the vessel 101 such that solids such as solid-phase resins can be separated from the contents, and the first reflecting member 106 is located between the irradiating position and the first opening portion 1011 so as to partition the vessel 101 such that a region that is closer to the first end 1015a than the first reflecting member 106 is can be made unlikely to be irradiated with microwaves.

Furthermore, for example, since the first opening portion 1011 may be located at the first end 1015a of the vessel 101 as described above, the treatment apparatus 1 may be such that, for example, the first filter 105 is located so as to partition the vessel 101, and the first reflecting member 106 is located closer to the first end 1015a than the emitting positions are and so as to partition the vessel 101. Note that, in this case, both the first filter 105 and the first reflecting member 106 are located away from the first opening portion 1011. For example, it is sufficient that the treatment apparatus 1 is configured such that the first filter 105 is located between the first end 1015a and the second end 1015b so as to partition the vessel 101, the first reflecting member 106 is located inside the vessel 101 between the irradiating position and the first end 1015a so as to partition the vessel 101, and the first opening portion 1011 is provided closer to the first end 1015a than the first filter 105 and the first reflecting member 106 are. Also in this case, effects similar to those described above are achieved.

The irradiation opening portions 1013 described above may be considered, for example, as opening portions used to perform microwave irradiation into the vessel 101. The irradiation opening portions 1013 may be considered, for example, as introduction ports for introducing microwaves into the vessel 101, portions for emitting microwaves into the vessel 101, that is, emitting portions of microwaves, or the like. The same applies to other embodiments.

Furthermore, the emitting positions described above may be considered, for example, as the positions of the irradiation opening portions 1013, and may be considered as positions of the above-described emitting portions. A positional relationship of the first filter 105, the first reflecting member 106, and a second filter 107, a second reflecting member 108, and the like described later relative to the emitting positions may be read as a positional relationship relative to the irradiation opening portions 1013 or the emitting portions. The same applies to other embodiments.

Embodiment 2

The treatment apparatus of this embodiment is different from the treatment apparatus described in Embodiment 1 above in that a filter that reflects microwaves is used instead of the first filter and the first reflecting member.

FIG. 4 shows a perspective view showing an example of a treatment apparatus in this embodiment (FIG. 4A), and a cross-sectional view thereof taken along the line IVb-IVb (FIG. 4B). In FIG. 4B, a cross-section of valves and the like have been omitted.

A treatment apparatus 2 of this embodiment includes the vessel 101, the irradiation units 102, a first valve 103, and a first reflecting filter 205. The vessel 101 has the first opening portion 1011, the second opening portion 1012, and the irradiation opening portions 1013. The constituent elements other than the first reflecting filter 205 are as in Embodiment 1 above, and thus a detailed description thereof has been omitted.

The first reflecting filter 205 is a filter configured from the first filter 105 and the first reflecting member 106 together, and is a filter that separates solid-phase resins from the contents of the vessel 101, and that reflects microwaves in the irradiation performed by the irradiation units 102 into the vessel 101. The first reflecting filter 205 is a filter made of stainless steel, which is a microwave-reflecting material, and has multiple holes for separating solid-phase resins from the contents of the vessel 101. There is no limitation on the material, the shape, and the like of the first reflecting filter 205, as long as microwaves can be reflected, and solid-phase resins can be separated from the contents of the vessel 101. The first reflecting filter 205 may be made of, for example, a microwave-reflecting material such as a metal other than stainless steel. The first reflecting filter 205 is preferably made of a chemically stable material with excellent corrosion resistance. For example, the first reflecting filter 205 may be a filter made of a metal or the like whose surface is coated with a material with high corrosion resistance and high microwave transmission such as PTFE. The size and the like of the multiple holes of the first reflecting filter 205 for separating solid-phase resins from the contents of the vessel 101 are similar to those of the holes of the first filter 105 in the foregoing embodiment, and thus a detailed description thereof has been omitted. Known examples of the filter made of a metal include a mesh made of a metal such as stainless steel, a metal filter obtained by integrating multiple metal meshes and the like by sintering them in an overlaid state, and the like.

The first reflecting filter 205 is configured from the first filter 105 and the first reflecting member 106 together, and thus it is sufficient that the first reflecting filter 205 is located at a position at which the first filter 105 can be located and at which the first reflecting member 106 can be located. Accordingly, as in the case of the first reflecting member 106 in the foregoing embodiment, the first reflecting filter 205 is located between the first end 1015a and emitting positions from which microwaves are emitted by the irradiation units 102, so as to partition the vessel 101. It is sufficient that the first opening portion 1011 is provided closer to the lower end, that is, closer to the first end 1015a than the first reflecting filter 205 is.

In the case in which the first reflecting filter 205 is a filter made of a metal such as stainless steel, the filter can be located alone inside the vessel 101 depending on the thickness, but, if it is difficult to locate the first reflecting filter 205 alone inside the vessel 101 due to its insufficient hardness or strength, a frame or the like for reinforcement may be attached to the first reflecting filter 205. The same applies to the second reflecting filter 206, which will be described later.

Also in this embodiment, as in the foregoing embodiment, it is possible to increase the throughput of peptides and the like through solid-phase synthesis, by increasing the size of the vessel 101. Since the first reflecting filter 205 is provided, it is possible to separate solid-phase resins from the contents. The solid-phase resins are prevented from migrating inside the vessel 101 from the region above the first reflecting filter 205 to the region below the first reflecting filter 205, and thus the solid-phase resins are prevented from being contained in this region. Furthermore, microwaves in the irradiation from the irradiation units 102 are reflected by the first reflecting filter 205 to the region above the first reflecting filter 205, and the contents not containing the solid-phase resins below the first reflecting filter 205 can be made unlikely to be irradiated with microwaves. Accordingly, it is possible to efficiently use microwaves for solid-phase synthesis treatment.

Embodiment 3

The treatment apparatus of this embodiment is different from the treatment apparatus described in Embodiment 1 above in that a second filter similar to the first filter and a second reflecting member similar to the first reflecting member are further provided on the second end side in the vessel.

Figure 5B:
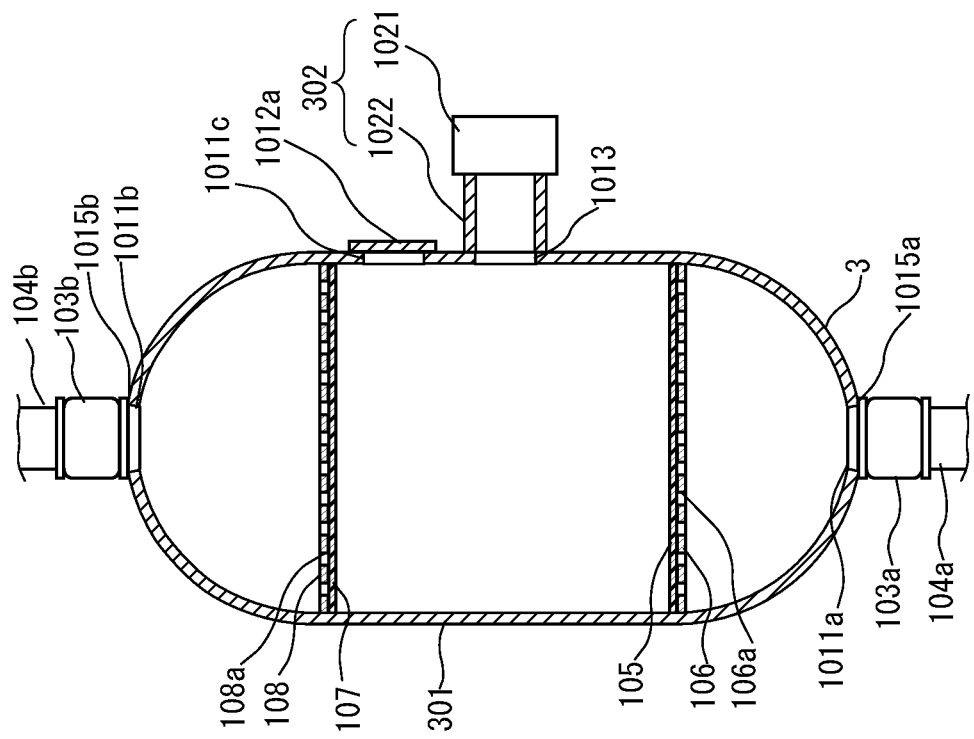
FIG. 5 shows a perspective view showing an example of a treatment apparatus according to Embodiment 3 of the present invention (FIG. 5A), and a cross-sectional view thereof taken along the line Vb-Vb (FIG. 5B).
Figure 5A:
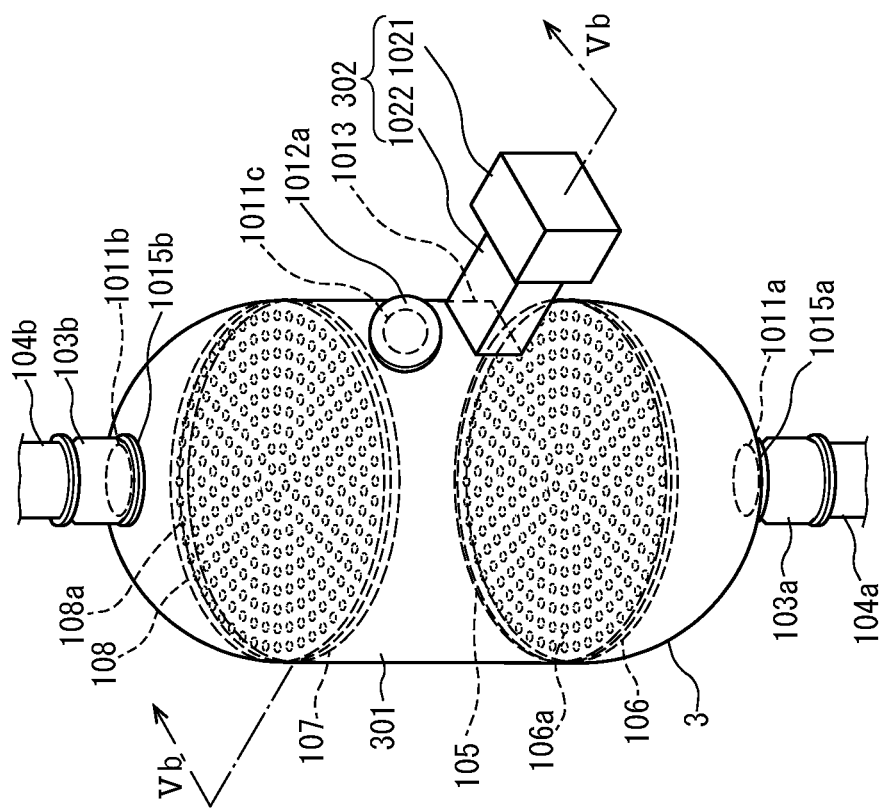

FIG. 5 shows a perspective view showing an example of a treatment apparatus in this embodiment (FIG. 5A), and a cross-sectional view thereof taken along the line Vb-Vb (FIG. 5B). In FIG. 5B, a cross-section of valves and the like have been omitted.

A treatment apparatus 3 includes a vessel 301, an irradiation unit 302, the first valve 103a, a second valve 103b, the first filter 105, the first reflecting member 106, a second filter 107, and a second reflecting member 108. The vessel 301 has a first opening portion 1011a, a second opening portion 1011b, a third opening portion 1011c, and the irradiation opening portion 1013. In the drawing, the same reference numerals as those in FIG. 1 denote the same or corresponding constituent elements, and a detailed description thereof has been omitted.

In this embodiment, a case will be described as an example in which the treatment apparatus 3 is a treatment apparatus used for solid-phase synthesis for synthesizing peptides bound to solid-phase resins, as in the treatment apparatus 1 in Embodiment 1 above. The treatment performed in the treatment apparatus 3 is similar to that in the treatment apparatus 1, and thus a detailed description thereof has been omitted. Note that the treatment apparatus 3 may be a treatment apparatus used for treatment other than solid-phase synthesis of peptides, as described later.

The vessel 301 is a vessel in which one or more sessions of treatment in solid-phase synthesis are performed. The vessel 301 has the first end 1015a and the second end 1015b. In this example, a case will be described as an example in which, as in the case of the vessel 101, the vessel 301 is a vertical-type vessel, the first end 1015a of the vessel 301 is the lower end of the vessel 301, and the second end 1015b is the upper end.

The vessel 301 is the same as the vessel 101 in Embodiment 1 above, for example, except that the first opening portion 1011a, the second opening portion 1011b, and the third opening portion 1011c are provided instead of the first opening portion 1011 and the second opening portion 1012, and the position from which microwaves are emitted by the irradiation unit 302 into the vessel 301, that is, the emitting position is between the first end 1015a and the second end 1015b, and thus a detailed description thereof has been omitted.

As in the vessel 101 in Embodiment 1 above, a stirring unit (not shown) for stirring the contents may be provided inside the vessel 301. As in the vessel 101, a unit (not shown) such as a temperature sensor for measuring the temperature inside the vessel 301, or a unit other than the temperature sensor, such as a pressure sensor for acquiring information indicating the status inside the vessel 301, may be provided inside or outside the vessel 301. It is also possible to perform feedback control of the temperature inside the vessel 301 and the power or frequency of microwaves in the irradiation into the vessel 301, using the values acquired by units such as the sensors. As in the vessel 101, the vessel 301 may be provided with an observation window (not shown) for observing the interior portion of the vessel 301. The vessel 301 may be a vessel whose internal pressure can be changed. For example, as in the vessel 101, the vessel 301 may be a vessel whose internal pressure can be reduced or increased.

The irradiation unit 302 performs microwave irradiation into the vessel 301 from a position that is between the first end 1015a and the second end 1015b of the vessel 301. In this example, the irradiation unit 302 performs microwave irradiation into the vessel 301 from a position that is between the lower end and the upper end of the vessel 301. Specifically, the irradiation unit 302 performs microwave irradiation into the vessel 301 from a point whose position in the longitudinal direction of the vessel 301 is between the first end 1015a and the second end 1015b of the vessel 301. In this example, a case will be described in which the irradiation unit 302 includes one pair of a microwave oscillator 1021 and a waveguide 1022 whose one end is connected to the microwave oscillator 1021, and performs microwave irradiation into the vessel 301 from one point. Specifically, the waveguide 1022 of the irradiation unit 302 is attached to the vessel 301 so as to be in communication with the irradiation opening portion 1013 of the vessel 301, and the irradiation unit 302 performs microwave irradiation into the vessel 301 via the irradiation opening portion 1013. The irradiation opening portion 1013 is located at a point whose position in the longitudinal direction of the vessel 301 is between the first end 1015a and the second end 1015b of the vessel 301. The position in the longitudinal direction of the vessel 301 may be considered as the position in the height direction of the vessel 301. In this example, a case will be described as an example in which the irradiation opening portion 1013 is located on the side face near the center in the height direction of the vessel 301. There is no limitation on the position of the irradiation opening portion 1013, as long as the irradiation unit attached to the irradiation opening portion 1013 can perform microwave irradiation into vessel 301 from a position between the first end 1015a and the second end 1015b of the vessel 301. In this example, a case will be described in which the waveguide 1022 is attached to the side face of the vessel 301 such that the axial direction of the waveguide 1022 is perpendicular to the longitudinal direction of the vessel 301, but there is no limitation on the angle and the like at which the waveguide 1022 is attached to the side face of the vessel 301. For example, the waveguide 1022 may be attached such that the axial direction is inclined relative to the longitudinal direction of the vessel 301. The irradiation unit 302, the microwave oscillator 1021 and the waveguide 1022 of the irradiation unit 302, and the like are the same as those in the irradiation units 102 in Embodiment 1 above, except for the position from which microwaves are emitted into the vessel 301, and thus a detailed description thereof has been omitted.

As in the irradiation units 102 in Embodiment 1 above, the irradiation unit 302 may be a unit other than that described above, as long as microwave irradiation can be performed into the vessel 301. For example, the irradiation unit 302 is not limited to that in which microwave irradiation is performed into the vessel 301 from one point, and may be any unit that can perform microwave irradiation into the vessel 301 from one or at least two positions between the lower end, which is the first end 1015a, and the upper end, which is the second end 1015b, of the vessel 301. The configuration in which microwave irradiation is performed from multiple points may be similar to that of the irradiation units 102 described in Embodiment 1 above, and thus a description thereof has been omitted.

Furthermore, the irradiation unit 302 may emit microwaves at different frequencies into the vessel 301, as in the case of the irradiation units 102 in Embodiment 1 above.

The first filter 105 is located inside the vessel 301 between the first end 1015a and an emitting position from which microwaves are emitted by the irradiation unit 302, so as to partition the vessel 301. The first filter 105 is located away from the first end 1015a in the longitudinal direction (the height direction, in this example) of the vessel 301. The state in which the first filter 105 is located between the first end 1015a and the emitting position refers to, for example, a state in which the first filter 105 is located such that the position of the first filter 105 in the longitudinal direction of the vessel 301 is between the first end 1015a and the emitting position. The first filter 105 is the same as the first filter 105 in Embodiment 1 above, except for the above-described aspect, and thus a detailed description thereof has been omitted.

As in Embodiment 1 above, the first filter 105 is preferably located at a position at a height of ¼ or less of the height of the vessel 301 in order to sufficiently secure a region for solid-phase growth treatment, but the first filter 105 may be located at a position at a height of more than ¼ of the height of the vessel 301.

The first reflecting member 106 is located inside the vessel 301 between the first end 1015a and the emitting position so as to partition the vessel 301. The first reflecting member 106 is located away from the first end 1015a in the longitudinal direction (the height direction, in this example) of the vessel 301. The state in which first reflecting member 106 is located between the first end 1015a and the emitting position refers to, for example, a state in which the first reflecting member 106 is located such that the position of the first reflecting member 106 in the longitudinal direction of the vessel 301 is between the first end 1015a and the emitting position. In this case, an example is shown in which the first reflecting member 106 is located inside the vessel 301 between the first filter 105 and the first end 1015a so as to partition the vessel 301. In this example, in particular, an example is shown in which the first filter 105 is laid over the first reflecting member 106, that is, the second end 1015b side of the first reflecting member 106. The first reflecting member 106 is the same as the first reflecting member 106 in Embodiment 1 above except for the above-described aspect, and thus a detailed description thereof has been omitted.

The second filter 107 is located inside the vessel 301 between the second end 1015b and the emitting position so as to partition the vessel 301. The second filter 107 is located away from the second end 1015b in the longitudinal direction (the height direction, in this example) of the vessel 301. The state in which the second filter 107 is located between the second end 1015b and the emitting position refers to, for example, a state in which the second filter 107 is located such that the position of the second filter 107 in the longitudinal direction of the vessel 301 is between the second end 1015b and the emitting position. The state in which the second filter 107 is located so as to partition the vessel 301 may be considered, for example, as a state in which the second filter 107 is located as in the case in which the first filter 105 is located so as to partition the vessel 101 or the vessel 301.

The second filter 107 separates solid-phase resins used for solid-phase synthesis from the contents of the vessel 301. The second filter 107 may be, for example, similar to the first filter 105 described above, and thus a detailed description thereof has been omitted. The second filter 107 may be the same as or different from the first filter 105. For example, the material of the second filter 107 may be the same as or different from the material of the first filter 105, as long as it is a microwave-transmitting material. For example, the multiple holes of the second filter 107 may be holes with the size, the shape, and the like that are the same as or different from those of the first filter 105, as long as their size, shape, and the like allow solid-phase resins used for solid-phase synthesis to be separated from the contents of the vessel 301.

The second filter 107 is preferably located at a position at a height of ¾ or more of the height of the vessel 301 in order to sufficiently secure a region for solid-phase growth treatment, but the second filter 107 may be located at a position at a height of less than ¾.

The second reflecting member 108 is located inside the vessel 301 between the second end 1015b and the emitting position so as to partition the vessel 301. The second reflecting member 108 is located away from the second end 1015b in the longitudinal direction (the height direction, in this example) of the vessel 301. In this case, an example is shown in which the second reflecting member 108 is located inside the vessel 301 between the second filter 107 and the second end 1015b so as to partition the vessel 301. In this example, in particular, an example is shown in which the second reflecting member 108 is laid over the second filter 107, that is, the second end 1015b side of the second filter 107.

The second reflecting member 108 is located so as to partition the vessel 301 as in the case of the first reflecting member 106, for example, except that it is located such that microwaves emitted from the emitting position into the vessel 301 are not transmitted to the region above the second reflecting member 108, that is, the region that is closer to the second end 1015b than the second reflecting member 108 is.

The second reflecting member 108 is laid over the second filter 107, that is, the second end 1015b side of the second filter 107 as in the case in which the first filter 105 is laid over the first reflecting member 106. Since the second filter 107 is laid over the lower side, that is, the first end 1015a side of the second reflecting member 108, the second filter 107 is preferably fixed to the first end 1015a side of the second reflecting member 108. The fixing may be performed in any manner, and, for example, if the hardness of the second filter 107 is insufficient as in the case in which the second filter 107 is a sheet-like filter, the second filter 107 may be attached to the lower side of the second reflecting member 108 with an adhesive or the like, or may be fastened to the lower side of the second reflecting member 108 with a fastener (not shown) or the like so as not to be detached therefrom.

The second reflecting member 108 allows at least the contents of the vessel 301 having passed through the second filter 107 (e.g., the contents after separating solid-phase resins used for synthesis, with the second filter 107) to pass through the second reflecting member 108, and reflects microwaves having been emitted by the irradiation unit 302. The second reflecting member 108 is made of, for example, stainless steel, which is a microwave-reflecting material. The second reflecting member 108 has, for example, multiple holes 108a each in a circular planar shape with a size that allows at least the contents of the vessel 301 having passed through the second filter 107 to pass through the hole 108a. The second reflecting member 108 may be, for example, similar to the first reflecting member 106 described above, and thus a detailed description thereof has been omitted.

The second reflecting member 108 may be the same as or different from the first reflecting member 106. For example, the material of the second reflecting member 108 may be the same as or different from the material of the first reflecting member 106, as long as it is a microwave-reflecting material. For example, the multiple holes of the second reflecting member 108 may be holes with the size, the shape, and the like that are the same as or different from those of the first reflecting member 106, as long as their size, shape, and the like allow the contents after removing solid-phase resins used for solid-phase synthesis to pass through the holes.

The first opening portion 1011a is located in the vessel 301 at a position thereof that is closer to the first end 1015a than the first filter 105 and the first reflecting member 106 are. That is to say, the first opening portion 1011a is located at a position that is closer to the first end 1015a than the first filter 105 is and that is closer to the first end 1015a than the first reflecting member 106 is. The first opening portion 1011a is an opening portion for discharging the contents of the vessel 301. The discharge of the contents may not be discharge of all contents. The contents of the vessel 301 are, for example, substances, solvent, a washing liquid (e.g., solvent), and the like used for solid-phase synthesis as described above. The liquid content is a concept that encompasses solutions, suspensions, and the like. The contents that are discharged from the first opening portion 1011a are, for example, a portion obtained by filtering through the first filter 105, which will be described later, from the contents held in the vessel 301 before discharge, and are a portion excluding the solid-phase resins that have been separated through filtering from the contents. In this case, an example is shown in which one first opening portion 1011a is provided, but multiple first opening portions 1011a may be provided. The first opening portion 1011a is preferably located at the lowermost portion of the vessel 301 such that the contents of the vessel 301 are naturally discharged. There is no limitation on the size and the shape of the first opening portion 1011a. The first opening portion 1011a may be, for example, similar to the first opening portion 1011.

The size of the first opening portion 1011a is preferably smaller than the size of a portion of the vessel 301 away from the first end 1015a (e.g., a portion near the center in the longitudinal direction, and a portion provided with the first filter 105 or the first reflecting member 106). The portion away from the first end 1015a is, for example, a portion away from the first end 1015a in the longitudinal direction of the vessel 301. The portion away from the first end 1015a may be considered as a portion away from the first opening portion 1011a.

The second opening portion 1011b is located in the vessel 301 at a position thereof that is closer to the second end 1015b, that is, closer to the upper end than the second filter 107 and the second reflecting member 108 are. That is to say, the second opening portion 1011b is located at a position that is closer to the second end 1015b than the second filter 107 is and that is closer to the second end 1015b than the second reflecting member 108 is. The second opening portion 1011b is an opening portion for supplying the contents into the vessel 301. The contents that are supplied from the second opening portion 1011b are, for example, substances, solvent, a washing liquid, gas, and the like used for solid-phase synthesis. The contents that are supplied from the second opening portion 1011b may be all or part of the contents that are supplied into the vessel 301. The contents that are supplied from the second opening portion 1011b are, for example, the contents that can pass through the second filter 107. The contents that are supplied from the second opening portion 1011b are, for example, substances, solvent, a washing liquid, gas, and the like used for solid-phase synthesis, other than the solid-phase resins. In this example, an example is shown in which one second opening portion 1011b is provided, but multiple second opening portions 1011b may be provided. There is no limitation on the size and the shape of the second opening portion 1011b. If there is no second valve 103b or the like, which will be described later, the second opening portion 1011b may be covered by an unshown cap, cover, stopper, or the like whenever supply of the contents is not performed. The structure, location, and the like of the second opening portion 1011b may be, for example, similar to those of the second opening portion 1012. Note that, contrary to the second opening portion 1012, the second opening portion 1011b is not typically used to supply solid-phase resins that are separated at the first filter 105 and the second filter 107.

The size of the second opening portion 1011b is preferably smaller than the size of a portion of the vessel 301 away from the second end 1015b (e.g., a portion near the center in the longitudinal direction, and a portion provided with the second filter 107 or the second reflecting member 108). The portion away from the second end 1015b is, for example, a portion away from the second end 1015b in the longitudinal direction of the vessel 301. The portion away from the second end 1015b may be considered as a portion away from the second opening portion 1011b.

The third opening portion 1011c is located in the vessel 301, in a region thereof that is located between the first filter 105 and the first reflecting member 106, and the second filter 107 and the second reflecting member 108. The region that is located between the first filter 105 and the first reflecting member 106, and the second filter 107 and the second reflecting member 108 is, for example, a region that is located between an area including both the first filter 105 and the first reflecting member 106, and an area including both the second filter 107 and the second reflecting member 108. For example, the region that is located between the first filter 105 and the first reflecting member 106, and the second filter 107 and the second reflecting member 108 is a region that is located between the one that is closer to the second end 1015b, of the first filter 105 and the first reflecting member 106, and the one that is closer to the first end 1015a, of the second filter 107 and the second reflecting member 108. The third opening portion 1011c is an opening portion for supplying substances, solvent, a washing liquid, gas, and the like used for solid-phase synthesis into the vessel 301. The contents that are supplied from the third opening portion 1011c are, for example, substances, solvent, a washing liquid, gas, and the like used for solid-phase synthesis. The contents that are supplied from the third opening portion 1011c may be all or part of the contents that are supplied into the vessel 301. The contents that are supplied from the third opening portion 1011c are, for example, the contents that cannot pass through the first filter 105 and the second filter 107. The contents that are supplied from the third opening portion 1011c are, for example, solid-phase resins, substances and solvent used for solid-phase synthesis containing solid-phase resins, and the like. For example, solid-phase resins cannot be supplied from the second opening portion 1011b to the region defined by the first filter 105 and the second filter 107 inside the vessel 301, and thus solid-phase resins are suppled from the third opening portion 1011c to this region. In this case, an example is shown in which one third opening portion 1011c is provided, but multiple third opening portions 1011c may be provided. There is no limitation on the size and the shape of the third opening portion 1011c.

The third opening portion 1011c is preferably an opening portion that can be covered by an unshown cap, stopper, or the like whenever supply is not performed. A pipe (not shown) or the like through which the contents that are to be supplied into the vessel 301 are sent to the third opening portion 1011c may be connected to the third opening portion 1011c via a valve (not shown) or the like. The third opening portion 1011*c* may be provided with one or more nozzles (not shown) or the like extending into the vessel 301, for supplying contents and the like into the vessel 301. The nozzles may be detachable. In this example, a case is shown in which the third opening portion 1011*c* is covered by an openable cover 1012*a*.

The first valve 103*a* is attached to the first opening portion 1011*a* of the vessel 301 as in the case of the first opening portion 1011 described above. The first valve 103*a* is further connected to a pipe 104*a*. The first valve 103*a* is used as a discharging unit for controlling discharge of the contents of the vessel 301 from the first opening portion 1011*a*. The first valve 103*a* is similar to the first valve 103*a* described in Embodiment 1 above, and thus a detailed description thereof has been omitted. If the contents of the vessel 301 are directly discharged from the first valve 103*a*, the pipe 104*a* may be omitted. The first valve 103*a* may be directly attached to the first opening portion 1011*a* as described above, or may be indirectly attached thereto via an unshown pipe or the like.

Furthermore, as in Embodiment 1 above, a discharging unit other than the first valve 103*a* may be provided instead of the first valve 103*a*. The discharging unit such as the first valve 103*a* may be considered as part of the treatment apparatus 3, or may be considered not as part of the treatment apparatus 3 but as being attached to the outside of the treatment apparatus 3, for example.

The second valve 103*b* is attached to the second opening portion 1011*b* of the vessel 301. The second valve 103*b* is further connected to a pipe 104*b*. The second valve 103*b* is used as a supply unit for controlling supply of the contents from the second opening portion 1011*b* into the vessel 301. When the second valve 103*b* is opened, the contents are supplied into the vessel 301 via the pipe 104*b* connected to the second valve 103*b*. When the second valve 103*b* is closed, the supply of the contents into the vessel 301 is stopped. The second valve 103*b* may be similar to the first valve 103*a*. If the contents are directly supplied from the second valve 103*b* into the vessel 301, the pipe 104*b* may be omitted. The second valve 103*b* may be directly attached to the second opening portion 1011*b* as described above, or may be indirectly attached thereto via an unshown pipe or the like.

Furthermore, in this embodiment, a case was described in which the second valve 103*b* is provided, but a supply unit other than the second valve 103*b* may be provided, as long as it is a supply unit that can be attached to the second opening portion 1011*b* of the vessel 301 and can control supply of the contents into the vessel 301. If the contents are directly supplied from the second opening portion 1011*b* into the vessel 301, the second valve 103*b* and the like may be omitted. In this case, a stopper, a cover, and the like that can open and close the second opening portion 1011*b* may be provided. For example, the pipe 104*b* may be directly connected to the second opening portion 1011*b* so that the contents are supplied via the pipe 104*b* into the vessel 301. In this embodiment, a case was described as an example in which the second valve 103*b* is part of the treatment apparatus 3, but the supply unit such as the second valve 103*b* may be considered as part of the treatment apparatus 3, or may be considered not as part of the treatment apparatus 3 but as being attached to the outside of the treatment apparatus 3, for example.

In the treatment apparatus 3 of this embodiment, the irradiation unit 302 performs microwave irradiation into the vessel 301 made of a microwave-reflecting material, and thus the microwaves can be confined inside the vessel 301, and it is possible to efficiently irradiate the contents with microwaves. The microwaves inside the vessel 301 can be set to a multi-mode, and thus concentration of microwaves on one location can be made unlikely to occur compared with that in a single-mode, and it is possible to irradiate the contents with microwaves more uniformly than in the single-mode. Accordingly, it is possible to irradiate the contents with microwaves efficiently and uniformly even when the size of the vessel 301 is increased. Accordingly, in this embodiment, it is possible to increase the throughput of peptides and the like through solid-phase synthesis, by increasing the size of the vessel 301. Furthermore, the treatment apparatus 3 of this embodiment includes the first filter 105, and thus the solid-phase resins are separated from the contents that have been supplied to the region between the first filter 105 and the second filter 107, and remain in the vessel 301. Accordingly, it is possible to wash the solid-phase resins by supplying solvent for washing into the vessel 301 in which the solid-phase resins have been separated, and to perform other treatment constituting solid-phase synthesis, without temporarily taking out the solid-phase resins, by supplying other materials, solvent, solutions, and the like into the vessel 301 in which the solid-phase resins have been separated.

Furthermore, in the treatment apparatus 3 of this embodiment, the first reflecting member 106 that reflects microwaves is provided on the lower side, that is, on the first end 1015*a* side of the first filter 105, and thus microwaves in the irradiation performed from a point above the first filter 105 are transmitted through the microwave-transmitting first filter 105, but are reflected by the first reflecting member 106 located therebelow and returned to the region above the first filter 105 holding the contents containing the solid-phase resins. Accordingly, the region below the first filter 105 in which solid-phase synthesis is not performed can be made unlikely to be irradiated with microwaves, and microwaves reflected by the first reflecting member 106 also can be used for solid-phase synthesis, and thus it is possible to efficiently use microwaves for solid-phase synthesis. Accordingly, in the treatment apparatus 3 of this embodiment, it is possible to efficiently perform solid-phase synthesis while suppressing unnecessary energy consumption. The first reflecting member 106 has a shape and a size that allow the contents having passed through the first filter 105 to pass through the first reflecting member 106, and thus the first reflecting member 106 does not impede discharge of the contents and the like.

Furthermore, for example, if the contents such as materials used for solid-phase synthesis are supplied into the vessel so as not to reach the upper end of the vessel, and solid-phase synthesis treatment is performed through microwave irradiation into the vessel in a state in which there is a space on the upper end side, the space on the upper end side in which there are no contents are irradiated with microwaves as well. Since the space on the upper end side does not contain the contents used for synthesis of solid-phase resins, and thus the microwaves in the irradiation performed in this portion do not directly contribute to solid-phase synthesis, and the energy is consumed in vain. Especially when the size of the vessel 301 is increased in order to increase the throughput of solid-phase synthesis, the region on the upper end side in which there are no contents is likely to increase as well, and thus it is conceivable that microwaves cannot be efficiently used.

On the other hand, in the treatment apparatus 3 of this embodiment, the second filter 107 and the second reflecting member 108 are provided, and thus microwaves that are emitted by the microwave irradiation unit are reflected by the second reflecting member 108. Thus, the region that is closer to the second end 1015b than the second reflecting member 108 is, that is, the region on the upper end side can be made unlikely to be irradiated with microwaves, and the region on the upper end side in the vessel 301 in which there are no contents and solid-phase synthesis is not performed can be prevented from being irradiated with microwaves, and thus it is possible to efficiently use microwaves. Since the second filter 107 is located between the microwave irradiating position and the second reflecting member 108, even when the contents have been filled into the vessel 301 up to a position that is higher than the second reflecting member 108, the solid-phase resins supplied to the region between the first filter 105 and the second filter 107 do not migrate to the region above the second filter 107, that is, the region on the second end 1015b side, and thus the solid-phase resins do not exist in the region inside the vessel 301 between the second reflecting member 108 and the second end 1015b, which is unlikely to be irradiated with microwaves. Accordingly, the solid-phase resins exist in the region inside the vessel 301 located between the first reflecting member 106 and the second reflecting member 108, which is irradiated with microwaves. Thus, it is possible to efficiently perform solid-phase synthesis by reducing the solid-phase resins not contributing to solid-phase synthesis.

Furthermore, since the solid-phase resins are supplied to the region between the first filter 105 and the second filter 107 and exists in this region, and, furthermore, since microwaves can be reflected between the first reflecting member 106 and the second reflecting member 108 that are laid over these filters, it is possible to set the region in which the solid-phase resins exist, by adjusting the positions where the first filter 105 and the second filter 107 are attached inside the vessel 301, and to perform solid-phase synthesis while setting this region to a region that is irradiated with microwaves. Accordingly, it is possible to set the size of the region inside the vessel 301 in which the solid-phase resins exist to a desired size, without changing the size and the like of the vessel 301, and to perform solid-phase synthesis in this region, and thus it is possible to eliminate unnecessary energy consumption. For example, it is possible to set the size of the region in which the solid-phase resins exist, in accordance with the amount and the like of solid-phase resins used for solid-phase synthesis, so that substantially only this region can be irradiated with microwaves. Accordingly, it is possible to set the size of the region in which solid-phase synthesis is performed to a size suitable for the amount and the like of solid-phase resins, and thus it is possible to eliminate unnecessary energy consumption.

Furthermore, in the treatment apparatus 3 of this embodiment, as in Embodiment 1 above, the first filter 105 is laid over the first reflecting member 106 made of a reflecting material such as a metal, and thus the first reflecting member 106 can reinforce and support the first filter 105 located on the upper face 1061, which is the face on the second end 1015b side, of the first reflecting member 106. Accordingly, it is possible to widen the range of choice of the first filter 105.

Furthermore, in the treatment apparatus 3 of this embodiment, the second reflecting member 108 made of a reflecting material such as a metal is laid over the second filter 107, and thus the second reflecting member 108 can reinforce and support the second filter 107 located on the lower face, which is the face on the first end 1015a side, of the second reflecting member 108. Accordingly, for example, the second filter 107, the sheet-like second filter 107, or the like, for which it is difficult to be located alone so as to partition the vessel 301 due to low hardness of the material thereof, can be located so as to partition the interior portion of the vessel 301. Accordingly, it is possible to widen the range of choice of the second filter 107.

Hereinafter, an example of solid-phase synthesis treatment using the treatment apparatus 3 of this embodiment will be described. In this example, a case will be described in which treatment similar to the solid-phase synthesis described in Embodiment 1 above is performed. It will be appreciated that substances used for solid-phase synthesis, the proportions thereof, and the like are merely an example, and substances and the like other than those described herein also may be used. Also, the procedure and the like of treatment performed herein are merely an example, and the treatment may be performed following other procedures. Furthermore, it will be appreciated that, in the vessel 301, solid-phase synthesis treatment other than the treatment described herein also may be performed, and only part of the treatment described herein also may be performed.

First, in a state in which the first valve 103a is closed, solid-phase resins to which an amino acid having an N-terminus protected by an Fmoc group or the like is bound are supplied via the third opening portion 1011c into the vessel 301 to the region between the first filter 105 and the second filter 107, and then the cover 1012a is closed. A deprotecting agent such as a piperidine solution in which DMF or the like is used as solvent is suppled from the second opening portion 1011b of the vessel 301. The deprotecting agent is supplied into the vessel 301 up to a position that is higher than the second reflecting member 108. Then, deprotection is performed by irradiating the contents of the vessel 301 with microwaves at 915 MHz from the irradiation unit 302, while stirring the contents with air bubbles by supplying nitrogen gas via an unshown nozzle or the like. The deprotecting agent and the solid-phase resins are held in the vessel 301 between the first filter 105 and the second filter 107, and only the deprotecting agent is held in the region below the first filter 105 and the region above the second filter 107. Note that the deprotecting agent migrates through the first filter 105, the first reflecting member 106, the second filter 107, and the second reflecting member 108. The microwaves emitted by the irradiation unit 302 are reflected by the first reflecting member 106 and the second reflecting member 108 to the region that is located between the first reflecting member 106 and the second reflecting member 108, and the region below the first filter 105 in which the solid-phase resins do not exist and the region above the second filter 107 in which the solid-phase resins do not exist, that is, the regions in which deprotection is unnecessary can be made unlikely to be irradiated with microwaves.

After deprotection is completed, when the first valve 103a is opened, the deprotecting agent above the second reflecting member 108, among the contents of the vessel 301, is discharged to the outside via the second reflecting member 108, the second filter 107, the first filter 105, the first reflecting member 106, the first opening portion 1011a, the first valve 103a, and the pipe 104a, the deprotecting agent between the first filter 105 and the second filter 107 is discharged to the outside via the first filter 105, the first reflecting member 106, the first opening portion 1011a, the first valve 103a, and the pipe 104a, and the deprotecting agent below the first reflecting member 106 is discharged to the outside via the first opening portion 1011a, the first valve 103a, and the pipe 104a. The deprotected solid-phase resins among the contents of the vessel 301 are separated from the deprotecting agent and remain on the upper face 1051 of the first filter 105.

Next, DMF that is supplied via the pipe 104b is supplied from the second opening portion 1011b into the vessel 301 by opening the second valve 103b and held in the vessel 301, after which DMF is discharged, and thus the deprotected solid-phase resins remaining on the upper face 1051 of the first filter 105 are washed. The washing is performed multiple times.

Next, HBTU, DIPEA, an amino acid for binding whose N-terminus is protected by an Fmoc group, and DMF that is used as solvent are supplied from the second opening portion 1011b into the vessel 301 by opening the second valve 103b, and thus HBTU, DIPEA, and the amino acid for binding are dissolved in DMF, after which the irradiation unit 302 performs microwave irradiation, so that the amino acid having a protected N-terminus is bound to deprotected amino acids bound to the solid-phase resins, through a condensation reaction. As described above, the vessel 301 is provided with the first filter 105 and the second filter 107, and thus the binding solution in which HBTU, DIPEA, and the amino acid for binding are dissolved in DMF, and the deprotected solid-phase resins are held in the region that is located between the first filter 105 and the second filter 107, and only the binding solution is held in the region below the first filter 105 and the region above the second filter 107. Note that the binding solution migrates through the first filter 105, the first reflecting member 106, the second filter 107, and the second reflecting member 108. As described above, the region below the first filter 105 in which the solid-phase resins do not exist and the region above the second filter 107 in which the solid-phase resins do not exist, that is, the regions in which the treatment for binding amino acids is unnecessary can be made unlikely to be irradiated with the microwaves emitted by the irradiation unit 302.

After binding of amino acids is ended, when the first valve 103a is opened, the binding solution is discharged out of the vessel 301, and the solid-phase resins to which an amino acid having a protected N-terminus is newly bound remain on the upper face 1051 of the first filter 105 without being discharged.

Subsequently, washing using DMF as described above is repeated multiple times.

Accordingly, it is possible to obtain peptides bound to the solid-phase resins on the upper face 1051 of the first filter 105. The following treatment is as in Embodiment 1 above, and thus a description thereof has been omitted.

As described above, according to this embodiment, microwave irradiation is performed into the microwave-reflecting vessel 301, and thus it is possible to increase the throughput of peptides and the like through solid-phase synthesis, by increasing the size of the vessel 301.

Furthermore, according to this embodiment, the first filter 105 is laid over the first reflecting member 106, and the second reflecting member 108 is laid over the second filter 107, and thus the first reflecting member 106 reflects microwaves having been transmitted through the first filter 105, and the second reflecting member 108 reflects microwaves having been transmitted through the second filter 107. Accordingly, the contents not containing the solid-phase resins below the first filter 105 and above the second filter 107 can be made unlikely to be irradiated with microwaves, and thus it is possible to efficiently use microwaves for solid-phase synthesis treatment.

Furthermore, according to this embodiment, the first filter 105 is laid over the first reflecting member 106, and thus the first filter 105 can be reinforced by the first reflecting member 106. Accordingly, for example, it is possible to widen the range of choice of the first filter 105, by relaxing the limitations on the strength, the hardness, and the like required for the first filter 105.

Furthermore, according to this embodiment, the second reflecting member 108 is laid over the second filter 107, and thus the second filter 107 can be reinforced by the second reflecting member 108. Accordingly, for example, it is possible to widen the range of choice of the second filter 107, by relaxing the limitations on the strength, the hardness, and the like required for the second filter 107.

First Modified Example

FIGS. 6A to 6C are cross-sectional views illustrating a first modified example of the treatment apparatus of this embodiment, and are cross-sectional views corresponding to FIG. 5B.

In the foregoing embodiment, a case was described in which the first filter 105 is laid over the first reflecting member 106, that is, the second end 1015b side of the first reflecting member 106, but the first filter 105 may not be directly laid over the first reflecting member 106, as long as the first reflecting member 106 is located between the first filter 105 and the first end 1015a, and preferably between the first filter 105 and the first opening portion 1011a.

For example, it is also possible to locate the first filter 105 and the first reflecting member 106 such that they are not directly laid over each other as shown in FIG. 6A. The location of the first filter 105 and the first reflecting member 106 corresponds to the modified example described with reference to FIG. 3A, among those in Embodiment 1 above, and thus a detailed description of this modified example has been omitted.

Furthermore, instead of locating the first reflecting member 106 between the first filter 105 and the first end 1015a, and preferably between the first filter 105 and the first opening portion 1011a, it is also possible to locate the first reflecting member 106 between the first filter 105 and the microwave emitting position as shown in FIG. 6B. The location of the first filter 105 and the first reflecting member 106 corresponds to the modified example described with reference to FIG. 3B, among those in Embodiment 1 above, and thus a detailed description of this modified example has been omitted. In this case, the first filter 105 may be made of a material other than microwave-transmitting materials.

Furthermore, as a mode in the case in which the first reflecting member 106 is located between the first filter 105 and the microwave emitting position, it is also possible to locate the first reflecting member 106 so as to be laid over the upper face of the first filter 105 as shown in FIG. 6C. The location of the first filter 105 and the first reflecting member 106 corresponds to the modified example described with reference to FIG. 3C, among those in Embodiment 1 above, and thus a detailed description of this modified example has been omitted.

Second Modified Example

FIGS. 7A to 7C are cross-sectional views illustrating a second modified example of the treatment apparatus of this embodiment, and are cross-sectional views corresponding to FIG. 5B.

Above, a modified example related to the first filter 105 and the first reflecting member 106 was described, but the second filter 107 and the second reflecting member 108 may be modified as in the foregoing first modified example, as described below.

For example, in the foregoing embodiment, a case was described in which the second reflecting member 108 is laid over the second filter 107, but the second reflecting member 108 may not be directly laid over the second filter 107, as long as the second reflecting member 108 is located between the second filter 107 and the second end 1015*b*, and preferably between the second filter 107 and the second opening portion 1011*b*.

For example, it is also possible to locate the second filter 107 and the second reflecting member 108 such that they are not directly laid over each other as shown in FIG. 7A. Also in this case, microwaves having been transmitted through the second filter 107 are reflected by the second reflecting member 108 located above the second filter 107, so that the region above the second reflecting member 108 is prevented from being irradiated with microwaves, and thus it is possible to efficiently use microwaves for solid-phase synthesis. Note that, in this case, the contents not containing the solid-phase resins between the second filter 107 and the second reflecting member 108 are irradiated with microwaves, and thus it may not be possible to efficiently use microwaves compared with the case in which the second filter 107 is laid over the second reflecting member 108. In this case, the second filter 107 cannot be reinforced by the second reflecting member 108, and thus it is necessary, for example, to use a second filter 107 with sufficient strength even without reinforcement as the second filter 107, or to additionally attach a reinforcing member (e.g., a reinforcing frame, etc.) made of a microwave-transmitting material to the second filter 107, which may lead to the limitation on the material or structure that can be used for the second filter 107, or an increase in the cost and the like because the configuration becomes complex due to the reinforcing member or the like.

Note that the treatment apparatus 3 described with reference to FIGS. 5 and 7A may be considered as an example in which the second reflecting member 108 is provided closer to the second end 1015*b* than the second filter 107 is, and, in particular, may be considered as an example in which the second filter 107 is provided between the microwave emitting position and the second end 1015*b*, and the second reflecting member 108 is provided closer to the second end 1015*b* than the second filter 107 is.

Furthermore, instead of locating the second reflecting member 108 between the second filter 107 and the second end 1015*b*, and preferably between the second filter 107 and the second opening portion 1011*b*, it is also possible to locate the second reflecting member 108 between the second filter 107 and the emitting position from which microwaves are emitted as shown in FIG. 7B. Also in this case, the second reflecting member 108 reflects microwaves, and thus the region above the second filter 107, that is, the region between the second filter 107 and the second end 1015*b* can be made unlikely to be irradiated with microwaves, and thus it is possible to efficiently use microwaves. In this case, the second filter 107 can prevent the solid-phase resins from migrating to the region that is closer to the second end 1015*b* than the second filter 107 is, and thus the second reflecting member 108 may be a filter through which the solid-phase resins can pass. For example, as the second reflecting member 108, a member having multiple holes with a shape and a size that allow the solid-phase resins to pass through the holes may be used. In this case, the contents containing the solid-phase resins between the second reflecting member 108 and the second filter 107 are unlikely to be irradiated with microwaves, and thus, if the distance between the second reflecting member 108 and the second filter 107 increases, the efficiency of the solid-phase synthesis treatment may deteriorate. Furthermore, in this case, the second filter 107 may be made of a material other than microwave-transmitting materials.

Furthermore, as a mode in the case in which the second reflecting member 108 is located between the second filter 107 and the microwave emitting position, it is also possible to locate the second reflecting member 108 so as to be laid over the first end 1015*a* side of the second filter 107 as shown in FIG. 7C. That is to say, the second filter 107 may be laid over the second reflecting member 108. In this case, it is possible to prevent the efficiency of solid-phase synthesis treatment from deteriorating as described above, by eliminating the distance between the second reflecting member 108 and the second filter 107, and to reinforce the second filter 107 with the second reflecting member 108, by locating the second reflecting member 108 on the second filter 107. If the second filter 107 and the second reflecting member 108 are laid over each other as in the foregoing embodiment or FIG. 7C, the second filter 107 can be reinforced by the second reflecting member 108, and thus it is possible to widen the range of choice of the second filter 107.

The treatment apparatus 3 described with reference to FIGS. 7B and 7C may be considered as an example in which, in the case in which the second filter 107 is provided between the second end 1015*b* and the microwave emitting position, the second reflecting member 108 is provided between the second filter 107 and the microwave emitting position.

In Embodiment 3 above, a case was described in which the first filter 105 is located inside the vessel 301 between the first end 1015*a* and an emitting position from which microwaves are emitted by the irradiation unit 302, the first reflecting member 106 is located inside the vessel 301 between the first end 1015*a* and the emitting position, the second filter 107 is located inside the vessel 301 between the second end 1015*b* and the emitting position, and the second reflecting member 108 is located inside the vessel 301 between the second end 1015*b* and the emitting position. However, it is sufficient that the treatment apparatus 3 is configured such that the first filter 105 is located so as to partition the vessel 301, the first reflecting member 106 is located closer to the first end 1015*a* than the emitting position is and so as to partition the vessel 301, the emitting position is located between the first end 1015*a* and the second end 1015*b*, the second filter 107 is located closer to the second end than the first filter 105 and the first reflecting member 106 are and so as to partition the vessel 301, and the second reflecting member 108 is located closer to the second end 1015*b* than the first filter 105 and the emitting position are and so as to partition the vessel 301. It is preferable that the first filter 105 and the first reflecting member 106 are located away from the first opening portion 1011*a*, and the second filter 107 and the second reflecting member 108 are located away from the second opening portion 1011*b*.

For example, the treatment apparatus 3 may be such that the first filter 105 is located inside the vessel 301 between the first end 1015*a* and the second end 1015*b* so as to partition the vessel 301, the first reflecting member 106 is located between the first end 1015*a* and the emitting position, the second filter 107 is located between the first filter 105 and the first reflecting member 106, and the second end 1015*b* so as to partition the vessel 301, and the second reflecting member 108 is located between the first filter 105 and the emitting position, and the second end 1015b so as to partition the vessel 301. Also in this case, the region between the first reflecting member 106 and the first end 1015a and the region between the second reflecting member 108 and the second end 1015b can be made unlikely to be irradiated with microwaves in the irradiation performed into the vessel 301, and effects similar to those in the foregoing embodiments are achieved. Also in this case, solids such as solid-phase resins that are to be separated may be supplied, for example, to the region between the first filter 105 and the second filter 107.

The state in which the second filter 107 is located between the first filter 105 and the first reflecting member 106, and the second end 1015b may be interpreted, for example, as a state in which the second filter 107 is located at a position that is between the first filter 105 and the second end 1015b and that is between the first reflecting member 106 and the second end 1015b. The position that is between the first filter 105 and the first reflecting member 106, and the second end 1015b may be considered, for example, as a position that is between an area including both the first filter 105 and the first reflecting member 106, and an area including the second end 1015b. The same interpretation applies to, for example, the above-described state in which the second reflecting member 108 is located between the first filter 105 and the emitting position, and the second end 1015b, and the later-described states in which the second filter 107 is located between the first filter 105 and the first reflecting member 106, and the second end 1015b, in which the second reflecting member 108 is located between the first filter 105 and the emitting position, and the second end 1015b, in which the second filter 107 is located between the first filter 105 and the first reflecting member 106, and the second end 1015b, and in which the second reflecting member 108 is located between the first filter 105 and the emitting position, and the second end 1015b.

For example, in the case in which the first reflecting member 106 is located closer to the first end 1015a than the first filter 105 is, and the first filter 105 and the first reflecting member 106 are located away from each other as in FIG. 6A, the irradiation unit 302 may perform microwave irradiation into the vessel 301 from a position between the first filter 105 and the first reflecting member 106 of the vessel 301. That is to say, the microwave emitting position may be set to a position that is between the first filter 105 and the first reflecting member 106 of the vessel 301. Solids such as solid-phase resins that are to be separated are supplied, for example, to the region between the first filter 105 and the second filter 107. In this configuration, as described above, the first filter 105 is located inside the vessel 301 between the first end 1015a and the second end 1015b, the second filter 107 is located between the first filter 105 and the first reflecting member 106, and the second end 1015b, and the second reflecting member 108 is located between the first filter 105 and the emitting position, and the second end 1015b. The position that is between the first filter 105 and the first reflecting member 106 of the vessel 301 is, for example, a point whose position in the height direction of the vessel 301 is between the first filter 105 and the first reflecting member 106. For example, the irradiation opening portion 1013 may be provided at a position that is between the first filter 105 and the first reflecting member 106 of the vessel 301, wherein the irradiation unit 302 performs microwave irradiation into the vessel 301 from the irradiation opening portion 1013.

Furthermore, for example, in the case in which the second reflecting member 108 is located closer to the second end 1015b than the second filter 107 is, and the second filter 107 and the second reflecting member 108 are located away from each other as in FIG. 7A, the irradiation unit 302 may perform microwave irradiation into the vessel 301 from a position between the second filter 107 and the second reflecting member 108 of the vessel 301. That is to say, the microwave emitting position may be set to a position that is between the second filter 107 and the second reflecting member 108 of the vessel 301. Solids such as solid-phase resins that are to be separated are supplied, for example, to the region between the first filter 105 and the second filter 107. In this configuration, as described above, the first filter 105 is located inside the vessel 301 between the first end 1015a and the second end 1015b, the second filter 107 is located between the first filter 105 and the first reflecting member 106, and the second end 1015b, and the second reflecting member 108 is located between the first filter 105 and the emitting position, and the second end 1015b. The position that is between the second filter 107 and the second reflecting member 108 of the vessel 301 is, for example, a point whose position in the height direction of the vessel 301 is between the second filter 107 and the second reflecting member 108. For example, the irradiation opening portion 1013 may be located at a position that is between the second filter 107 and the second reflecting member 108 of the vessel 301, wherein the irradiation unit 302 performs microwave irradiation into the vessel 301 from the irradiation opening portion 1013.

As the second filter 107 and the second reflecting member 108 of the treatment apparatus 3 in Embodiment 3 above and the first modified example thereof, it is possible to use any one combination of the second filter 107 and the second reflecting member 108 described with reference to FIGS. 7A to 7C in the second modified example of Embodiment 3 above. As the first filter 105 and the first reflecting member 106 in Embodiment 3 above and the second modified example thereof, it is possible to use any one combination of the first filter 105 and the first reflecting member 106 described with reference to FIGS. 6A to 6C in the first modified example of Embodiment 3 above. For example, it is sufficient that the treatment apparatus 3 includes any one combination of the first filter 105 and the first reflecting member 106 described in Embodiment 3 above and the first modified example thereof and any one combination of the second filter 107 and the second reflecting member 108 described in Embodiment 3 above and the second modified example thereof.

Embodiment 4

The treatment apparatus of this embodiment is different from the treatment apparatus described in Embodiment 3 above in that a filter that reflects microwaves is used instead of each of the first filter and the first reflecting member, and the second filter and the second reflecting member.

FIG. 8 shows a perspective view showing an example of a treatment apparatus in this embodiment (FIG. 8A), and a cross-sectional view thereof taken along the line VIIIb-VIIIb (FIG. 8B). In FIG. 8B, a cross-section of valves and the like have been omitted.

A treatment apparatus 4 of this embodiment includes the vessel 301, the irradiation unit 302, the first valve 103a, the second valve 103b, the first reflecting filter 205, and a second reflecting filter 206. The vessel 301 has the first opening portion 1011a, the second opening portion 1011b, the third opening portion 1011c, and the irradiation opening portion 1013. The constituent elements other than the first reflecting filter 205 and the second reflecting filter 206 are as in Embodiment 3 above, and thus a detailed description thereof has been omitted.

The first reflecting filter 205 is a filter configured from the first filter 105 and the first reflecting member 106 together, and is a filter that separates solid-phase resins from the contents of the vessel 301, and that reflects microwaves in the irradiation performed by the irradiation unit 302 into the vessel. The first reflecting filter 205 is described in Embodiment 2 above, and thus a detailed description thereof has been omitted.

The location of the first reflecting filter 205 is as in Embodiment 2 above, except that the emitting position is the emitting position of the irradiation unit 302, and thus a detailed description thereof has been omitted.

The second reflecting filter 206 is a filter configured from the second filter 107 and the second reflecting member 108 together, and is a filter that separates solid-phase resins from the contents of the vessel 301, and that reflects microwaves in the irradiation performed by the irradiation unit 302 into the vessel. The second reflecting filter 206 may be similar to the first reflecting filter 205, and thus a detailed description thereof has been omitted. The first reflecting filter 205 and the second reflecting filter 206 may be the same or different from each other.

The second reflecting filter 206 is configured from the second filter 107 and the second reflecting member 108 together, and thus it is sufficient that the second reflecting filter 206 is located at a position at which the second filter 107 can be located and at which the second reflecting member 108 can be located. Accordingly, as in the case of the second reflecting member 108 in the foregoing embodiment, the second reflecting filter 206 is located between the second end 1015b and an emitting position from which microwaves are emitted by the irradiation unit 302. It is sufficient that the second opening portion 1011b is provided closer to the upper end, that is, closer to the second end 1015b than the second reflecting filter 206 is. A frame or the like for reinforcement may be attached to the first reflecting filter 205 and the second reflecting filter 206.

Also in this embodiment, as in the foregoing embodiments, it is possible to increase the throughput of peptides and the like through solid-phase synthesis, by increasing the size of the vessel 301. Since the first reflecting filter 205 is provided, it is possible to separate solid-phase resins from the contents. The solid-phase resins are prevented from migrating inside the vessel 301 from the region between the first reflecting filter 205 and the second reflecting filter 206 to the region below the first reflecting filter 205 and the region above the second reflecting filter 206, and thus the solid-phase resins are prevented from being contained in these regions. Furthermore, microwaves in the irradiation from the irradiation unit 302 are reflected by the first reflecting filter 205 and the second reflecting filter 206 to the region located between the first reflecting filter 205 and the second reflecting filter 206, and the contents not containing the solid-phase resins below the first reflecting filter 205 and above the second reflecting filter 206 can be made unlikely to be irradiated with microwaves. Accordingly, it is possible to efficiently use microwaves for solid-phase synthesis treatment.

The first reflecting filter 205 in Embodiment 4 above may be used instead of the first filter 105 and the first reflecting member 106 of the treatment apparatus 3 described in Embodiment 3 and the second modified example thereof as shown in FIGS. 5 and 7A to 7C, and the second reflecting filter 206 in Embodiment 4 above may be used instead of the second filter 107 and the second reflecting member 108 of the treatment apparatus 3 described in Embodiment 3 and the first modified example thereof as shown in FIGS. 5 and 6A to 6C. For example, it is sufficient that the treatment apparatus includes either the combination of the first filter 105 and the first reflecting member 106 described in Embodiment 3 above and the first modified example thereof or the first reflecting filter 205, and either the combination of the second filter 107 and the second reflecting member 108 described in Embodiment 3 above and the second modified example thereof or the second reflecting filter 206.

In Embodiments 1 to 4 above, a case was described in which the treatment apparatus includes the irradiation units 102 or the irradiation unit 302, but the treatment apparatus may or may not include the irradiation units 102 or the irradiation unit 302. For example, the portion excluding the irradiation units 102 or the irradiation unit 302 from the treatment apparatus 1 may be considered as a treatment apparatus, and the irradiation units 102 or the irradiation unit 302 may be considered as an apparatus separate from the treatment apparatus. In this case, when performing microwave irradiation using the treatment apparatus, for example, the irradiation units 102 or the irradiation unit 302 that is separate from the treatment apparatus may be additionally prepared and attached to the treatment apparatus.

Furthermore, in Embodiments 1 to 4 above, an examples was described in which the vessel 101 has the irradiation opening portion 1013, and microwave irradiation is performed from the irradiation opening portion 1013, but it is sufficient that the vessel 101 includes an emitting portion (not shown) of microwaves in the irradiation that is performed into the vessel 101 so that microwave irradiation is performed from this emitting portion into the vessel 101. The emitting portion of microwaves is a portion that emits microwaves in the irradiation performed into the vessel 101. The emitting portion may have, for example, any structure and any shape, as long as microwaves in the irradiation performed by the irradiation units 102 can be emitted (i.e., introduced) into the vessel 101. For example, the irradiation opening portion 1013 in the foregoing embodiment may be considered as the emitting portion. The position of the emitting portion may be considered as the microwave emitting positions described above. A positional relationship of the first filter 105, the first reflecting member 106, the second filter 107, the second reflecting member 108, and the like relative to the emitting position may be read as a positional relationship relative to the irradiation opening portion 1013 or the emitting portion.

Embodiment 5

FIG. 9 shows a perspective view showing an example of a column in this embodiment (FIG. 9A), and a cross-sectional view thereof taken along the line IXb-IXb (FIG. 9B).

Figure 10A:
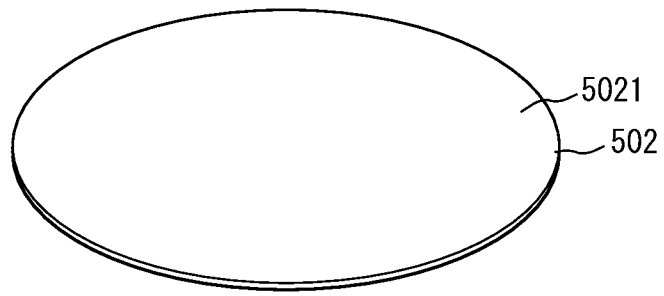
FIG. 10 shows a perspective view of a filter of the column viewed obliquely from above (FIG. 10A), a perspective view of a reflecting member viewed obliquely from above (FIG. 10B), a perspective view of the reflecting member and the filter that is located on the reflecting member viewed obliquely from above (FIG. 10C), and a perspective view of the reflecting member and the filter that is located on the reflecting member viewed obliquely from below (FIG. 10D).
Figure 10B:
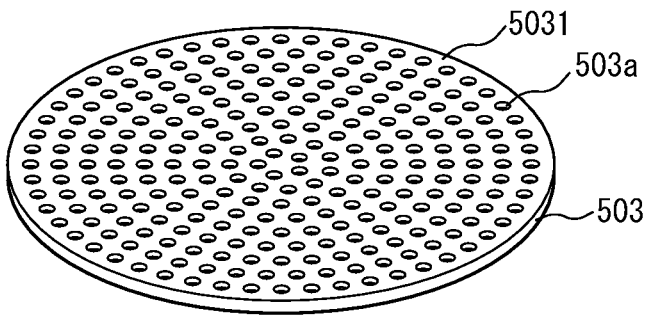
Figure 10C:
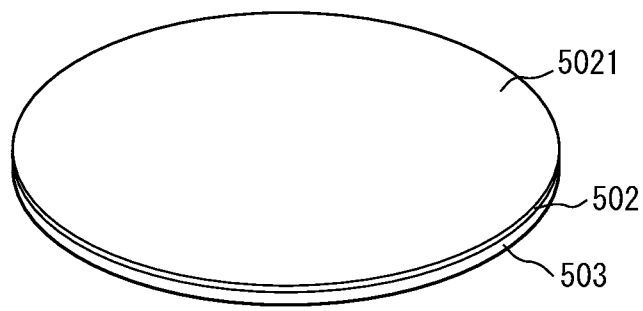
Figure 10D:
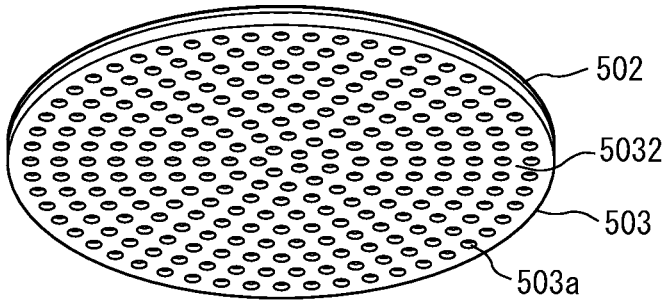

FIG. 10 shows a perspective view of a first filter of the column in this embodiment viewed obliquely from above (FIG. 10A), a perspective view of a first reflecting member viewed obliquely from above (FIG. 10B), a perspective view of the first reflecting member and the first filter that is located on the first reflecting member viewed obliquely from above (FIG. 10C), and a perspective view of the reflecting member and the filter that is located on the reflecting member viewed obliquely from below (FIG. 10D).

A column 5 includes a cylindrical member 501, a first filter 502, a first reflecting member 503, a second filter 504, and a second reflecting member 505. The cylindrical member 501 has a first end 5011a, a second end 5011b, an introduction port 5013, and a microwave-transmitting member 5014.

In this embodiment, a case will be described as an example in which the column 5 is a column used for solid-phase synthesis for synthesizing peptides bound to solid-phase resins. Note that the column 5 may be a column used for treatment other than solid-phase synthesis of peptides, as described later.

The column 5 of this embodiment is used to perform one or more of multiple sessions of treatment constituting the solid-phase synthesis described in Embodiment 1 above and the like. The column 5 is used, for example, in a state of being attached to a treatment apparatus (not shown) for performing solid-phase synthesis. The column of this embodiment can be used, for example, in one or at least two sessions of treatment as described in Embodiment 1 above and the like.

The cylindrical member 501 is a member with a cylindrical shape. The cylindrical member 501 is a hollow member. The cylindrical member 501 has a cylindrical shape whose cross-section that is perpendicular to the axial direction is in the shape of a perfect circle. There is no limitation on the length in the axial direction of the cylindrical member 501. There is no limitation on the diameter and the like of the cross-section that is perpendicular to the axial direction of the cylindrical member 501. In this example, the cross-sectional shape of the cylindrical member 501 may be a shape other than a perfect circle, and examples thereof include a polygonal shape, an oval shape, and the like. The cross-sectional shape of the inner face of the cylindrical member 501 preferably has the same shape and size throughout the axial direction. Note that the cross-sectional shape of the inner face of the cylindrical member 501 may have different shapes or sizes at different positions along the axial direction, may have different shapes or sizes partially in the axial direction. The cylindrical member 501 may be considered as a cylindrical vessel.

The cylindrical member 501 has the first end 5011a and the second end 5011b. The first end 5011a and the second end 5011b are portions at both ends in the axial direction of the cylindrical member 501. Both the first end 5011a and the second end 5011b are open. The inner diameter of the portions that are open in this example is the same as the inner diameter of other portions in the cylindrical member 501. Note that the inner diameter of the portions that are open may be slightly larger or smaller than the other portions. In this example, a case will be described in which the cylindrical member 501 is used in a state where its axial direction is along the vertical direction. In this example, a case will be described in which it is used in a state where the first end 5011a of the cylindrical member 501 is the lower end, and the second end 5011b is the upper end. Hereinafter, the portion of the first end 5011a that is open is referred to as a first opening portion 5012a, the portion of the second end 5011b that is open is referred to as a second opening portion 5012b.

The cylindrical member 501 is made of a microwave-reflecting material. The microwave-reflecting material is, for example, a conductive substance. Examples of the microwave-reflecting material include metals such as stainless steel. The cylindrical member 501 is preferably a material with excellent corrosion resistance. For example, the cylindrical member 501 is preferably made of stainless steel. There is no limitation on the thickness of the outer wall and the like of the cylindrical member 501. The inner wall of the cylindrical member 501 may be coated with a material with high microwave transmission, excellent corrosion resistance, and the like, such as polytetrafluoroethylene (PTFE) or glass. For example, the cylindrical member 501 may be a vessel with a double structure in which the inner wall is made of such a material with high microwave transmission, excellent corrosion resistance, and the like, and the outer wall is made of a microwave-reflecting material such as stainless steel.

The side face of the cylindrical member 501 is provided with the introduction port 5013 for introducing microwaves to the inside from the outside of the cylindrical member 501. The side face of the cylindrical member 501 may be considered as the outer circumferential portion or the side wall of the cylindrical member 501. The inside of the cylindrical member 501 may be considered as a portion inside the cylindrical member 501 or an interior portion of the cylindrical member 501. Introducing microwaves may be considered as irradiating the interior portion of the cylindrical member 501 with microwaves. The introduction port 5013 may be considered, for example, as a portion that emits microwaves in the irradiation performed into the cylindrical member 501, that is, an emitting portion of microwaves. The introduction port 5013 is an opening portion covered by the plate-like microwave-transmitting member 5014. The shape of the introduction port 5013 may be, for example, a rectangular shape, a circular shape, or a slit-like shape, and there is no limitation on the shape, the size, and the like thereof. In this example, a case is shown in which only one introduction port 5013 is provided, but the number of introduction ports 5013 may be multiple. The introduction port 5013 is provided at a portion near the center in the axial direction of the cylindrical member 501. There is no limitation on the position and the like at which the introduction port 5013 is provided on the side face of the cylindrical member 501.

The microwave-transmitting member 5014 is a member made of a microwave-transmitting material. The microwave-transmitting member 5014 is preferably a material with excellent corrosion resistance. In this example, a case will be described in which the microwave-transmitting member 5014 is a plate-like member made of PTFE. The microwave-transmitting member 5014 may not be a plate-like member. The introduction port 5013 is covered by a microwave-transmitting material, and thus it is possible to introduce microwaves from the outside into the cylindrical member 501 via the introduction port 5013, and to prevent the contents of the cylindrical member 501 from being discharged to the outside via the introduction port 5013.

Joints (not shown) or the like for attaching a waveguide, an antenna, or the like for introducing microwaves into the cylindrical member 501 via the introduction port 5013 may be provided around the introduction port 5013. Instead of the microwave-transmitting member 5014, an antenna or the like for introducing microwaves into the cylindrical member 501 may be used to cover the introduction port 5013.

For example, if an opening portion (not shown) on the cylindrical member 501 side of a waveguide (not shown) attached so as to cover the introduction port 5013 is covered by a member made of a microwave-transmitting material, the introduction port 5013 may not be covered by a member made of a microwave-transmitting material. If the opening portion of the introduction port 5013 can be covered by an antenna attached to the introduction port 5013 and used for performing microwave irradiation, the introduction port 5013 may be an opening portion not covered by a member made of a microwave-transmitting material.

There is no limitation on the manner in which microwaves are introduced into the cylindrical member 501 via the introduction port 5013. For example, microwave irradiation may be performed via a waveguide passage, such as a waveguide (not shown) for propagating microwaves in the irradiation performed by a microwave irradiation apparatus (not shown) or the like or a coaxial cable (not shown) or the like having an antenna, the waveguide passage being connected to the introduction port 5013. Furthermore, microwaves may be introduced into the cylindrical member 501 via the introduction port 5013, by locating the entire column 5 or at least a side face portion of the cylindrical member 501 on the waveguide or the like for propagating microwaves.

The introduction port 5013 is preferably provided on the side face of the cylindrical member 501, in a region that is closer to the second end 5011b than the first filter 502 and the first reflecting member 503 are and that is closer to the first end 5011a than the second filter 504 and the second reflecting member 505 are.

The cylindrical member 501 is, for example, a vessel in which one or more sessions of treatment constituting solid-phase synthesis are performed. As in the foregoing embodiments, for example, substances, intermediate products, solvent, and the like used for solid-phase synthesis are supplied to and held in the cylindrical member 501. For example, the cylindrical member 501 holds these substances and intermediate products together with proper solvent. It is also possible to continuously perform treatment in a state in which contents flow through the cylindrical member 501, by continuously supplying and discharging the contents to and from the cylindrical member 501.

As in the foregoing embodiments, a stirring unit (not shown) for stirring the contents may be provided inside the cylindrical member 501.

Although not shown, the outer perimeter of the cylindrical member 501 may be provided with a hot water jacket, a cold water jacket, a heater, or the like for adjusting the temperature of the cylindrical member 501.

The shape and the size of the cylindrical member 501 are preferably set such that, for example, the microwave mode inside the cylindrical member 501 is a multi-mode. For example, the cylindrical member 501 preferably has the shape, the size, and the like that allow microwave irradiation to be performed in a multi-mode inside the cylindrical member 501 with microwaves introduced from the introduction port 5013. For example, the multi-mode of microwaves is, for example, a mode in which there is no stationary waves of microwaves inside the cylindrical member 501.

The first filter 502 separates, for example, solid-phase resins used for solid-phase synthesis from the contents of the cylindrical member 501. The first filter 502 has, for example, has multiple holes for separating solid-phase resins used for solid-phase synthesis from the contents of the cylindrical member 501. The holes are, for example, holes formed through the first filter 502 from a front face 5021 to a back face. The front face 5021 of the first filter 502 in this example is the face on the second end 5011b side of the first filter 502. For example, the multiple holes of the first filter 502 are holes with a size smaller than that of the particle size of the solid-phase resins contained in the contents. Accordingly, only the solid-phase resins in the contents of the cylindrical member 501 are separated through filtering, and remain on the front face 5021 of the first filter 502, whereas substances such as the activator and the deprotecting agent dissolved in the solvent, amino acids dissolved or suspended in the solvent, and the like pass through the holes of the first filter 502 together with the solvent. The first filter 502 may be, for example, similar to the first filter 105 described in the foregoing embodiment, and thus a detailed description thereof has been omitted. In this embodiment, a case will be described as an example using a sheet-like first filter 502 made of a PTFE porous material, as in the foregoing embodiments.

The first filter 502 is located so as to obstruct the first end 5011a side of the cylindrical member 501. The state in which the first filter 502 is located so as to obstruct the first end 5011a side refers to a state in which the first filter 502 is located so as to obstruct the first opening portion 5012a or its vicinity at the first end 5011a of the cylindrical member 501. The first end 5011a side may be, for example, the first end 5011a, or may be the vicinity of the first end 5011a. The state in which the first filter 502 obstructs the cylindrical member 501 refers to, for example, a state in which the first filter 502 is provided such that the contents of the cylindrical member 501 do not migrate from the first end 5011a to the outside without passing through the first filter 502. Since the cylindrical member 501 is obstructed by the first filter 502, for example, the contents of the cylindrical member 501 that can pass through the first filter 502 can migrate between the inside and the outside of the cylindrical member 501 via the first opening portion 5012a on the first end 5011a side through the first filter 502. The contents are a concept that encompasses those that will be the contents of the cylindrical member 501, such as those that are supplied as the contents of the cylindrical member 501, and those that are about to be placed into the cylindrical member 501. The same applies to the description below.

The first filter 502 may be located at a point whose position in the axial direction is closer to the second end 5011b than the first end 5011a is, and may be located closer to the second end 5011b than the first end 5011a is, for example, within the range where the distance from the first end 5011a is 3 cm or less, and preferably 1 cm or less. In this example, the first filter 502 is laid over the second end 5011b side of the first reflecting member 503, which will be described later. Accordingly, the first filter 502 is located closer to the second end 5011b than the first end 5011a is by the thickness of the first reflecting member 503.

The first filter 502 may be located so as to obstruct the first end 5011a of the cylindrical member 501. The state of being located so as to obstruct the first end 5011a refers to, for example, a state in which the first filter 502 is located at the first opening portion 5012a at the first end 5011a such that the first opening portion 5012a at the first end 5011a is obstructed by the first filter 502.

The first reflecting member 503 is a flat plate-like member made of a microwave-reflecting material, and having the multiple holes 503a that can reflect microwaves having been introduced into the cylindrical member 501, and through which at least the contents of the cylindrical member 501 having passed through the first filter 502 can pass. The holes 503a are, for example, formed through the first reflecting member 503 from a front face 5031 on the second end 5011b side of the first reflecting member 503, to a back face 5032. The diameter of each hole 503a is set to a size that allows at least the contents having passed through the first filter 502 to pass through the hole 503a, and that allows microwaves having been introduced into the introduction port 5013 to be reflected. The size of each hole 503a may be, for example, any size that is that is equal to or larger than the size that allows at least the contents having passed through the first filter 502, among the contents of the cylindrical member 501, to pass through the hole 503a, and, for example, it may be a size that allows a portion excluding the solid-phase resins separated by the first filter 502, among the contents of the cylindrical member 501, to pass through the hole 503*a*, or may be a size that allows the contents also including the solid-phase resins to pass through the hole 503*a*. For example, the first reflecting member 503 may be a mesh or the like made of a microwave-reflecting material such as stainless steel having multiple opening portions with a size that allows at least the contents of the cylindrical member 501 having passed through the first filter 502 to pass through the multiple opening portions. The opening portions may be considered as corresponding to the holes of the first reflecting member 503. The first reflecting member 503 may be, for example, similar to the first reflecting member 106 described in the foregoing embodiment, and thus a detailed description thereof has been omitted.

In this embodiment, for example, the first reflecting member 503 is composed of perforated metal made of stainless steel having the multiple holes 503*a* each in a circular shape with a diameter that is larger than that of the solid-phase resins and that allows microwaves having been introduced into the introduction port 5013 to be reflected. Accordingly, the first reflecting member 503 allows the contents having passed through the first filter 502 to pass through the first reflecting member 503, and reflects microwaves having been introduced into the introduction port 5013.

FIGS. 9, 10B, 10D, and the like are drawings for illustration, that is, a relationship between the size of the multiple holes 503*a* provided through the first reflecting member 503 and the size of the first reflecting member 503, the number of the multiple holes 503*a*, and the like in these drawings are merely for illustration, and do not necessarily match those of the actual first reflecting member 503. The first reflecting member 503 may not be a flat plate-like member.

The first reflecting member 503 may be made of any material and may have any shape and structure other than those described above, as long as at least the contents of the cylindrical member 501 having passed through the first filter 502 can pass through the first reflecting member 503, and microwaves having been introduced into the introduction port 5013 are reflected. Accordingly, the first reflecting member 503 reflects microwaves having been introduced into the cylindrical member 501 from the introduction port 5013, and allows at least the contents of the cylindrical member 501 having passed through the first filter 502 to pass through the first reflecting member 503. For example, it is sufficient that the length of the widest portion of each of the multiple opening portions is set to be smaller than the half-wavelength of microwaves that are introduced into the introduction port 5013, and the length of the narrowest portion of each of the opening portions is set to be larger than that of the contents having passed through the first filter 502. There is no limitation on the planar shape and the like of the multiple opening portions of the mesh.

If the later-described first filter 502 that is laid over the first reflecting member 503 is reinforced and supported, the first reflecting member 503 is preferably made of a material with high strength such as metal.

The first reflecting member 503 is located so as to obstruct the first end 5011*a* of the cylindrical member 501. The state of being located so as to obstruct the first end 5011*a* refers to, for example, a state in which the first reflecting member 503 is located at the first opening portion 5012*a* at the first end 5011*a* of the cylindrical member 501 such that the first opening portion 5012*a* at the first end 5011*a* is obstructed by the first reflecting member 503. The state in which the first reflecting member 503 is located so as to obstruct the first end 5011*a* of the cylindrical member 501 may be considered, for example, as a state in which the first reflecting member 503 is located at the cylindrical member 501 such that microwaves having been introduced into the cylindrical member 501 do not pass through the first opening portion 5012*a* at the first end 5011*a* to the outside. The state in which the first reflecting member 503 obstructs the cylindrical member 501 may refer to, for example, a state in which the first reflecting member 503 is provided such that the contents of the cylindrical member 501 do not migrate from the first end 5011*a* to the outside without passing through the first reflecting member 503. If the cylindrical member 501 is obstructed by the first reflecting member 503, for example, the contents of the cylindrical member 501 that can pass through the first reflecting member 503 can migrate between the inside and the outside of the cylindrical member 501 via the first opening portion 5012*a* on the first end 5011*a* side through the first reflecting member 503.

The first filter 502 is laid over the second end 5011*b* side of the first reflecting member 503. The first filter 502 is located on the front face 5031 on the second end 5011*b* side of the first reflecting member 503.

If the first filter 502 is laid over the lower side of the first reflecting member 503, the first filter 502 is preferably fixed to the first end 5011*a* side of the first reflecting member 503.

The first reflecting member 503 may be located at a point whose position in the axial direction is closer to the second end 5011*b* than the first end 5011*a* is. For example, the first reflecting member 503 may be located closer to the second end 5011*b* than the first end 5011*a* is, within the range where the distance from the first end 5011*a* is 3 cm or less, and preferably 1 cm or less. That is to say, it is sufficient that the first reflecting member 503 is located so as to obstruct the first end 5011*a* side of the cylindrical member 501. The state in which the first reflecting member 503 is located so as to obstruct the first end 5011*a* side refers to a state in which the first reflecting member 503 is located so as to obstruct the first opening portion 5012*a* or its vicinity at the first end 5011*a*. The first end 5011*a* side may be, for example, the first opening portion 5012*a* at the first end 5011*a*, or may be the vicinity thereof.

Furthermore, the planar shape of the first reflecting member 503 may have, for example, any shape and any size that allow the first opening portion 5012*a* at the first end 5011*a* to be obstructed.

The second filter 504 separates, for example, solid-phase resins used for solid-phase synthesis from the contents of the cylindrical member 501. The second filter 504 may be, for example, similar to the first filter 502 described above, and thus a detailed description thereof has been omitted. The second filter 504 may be the same as or different from the first filter 502. For example, the material of the second filter 504 may be the same as or different from the material of the first filter 502, as long as it is a microwave-transmitting material. For example, the multiple holes of the second filter 504 may be holes with the size, the shape, and the like that are the same as or different from those of the first filter 502, as long as their size, shape, and the like allow solid-phase resins used for solid-phase synthesis to be separated from the contents of the cylindrical member 501.

The second filter 504 is located so as to obstruct the second end 5011*b* side of the cylindrical member 501. The state in which the second filter 504 is located so as to obstruct the second end 5011*b* side refers to a state in which the second filter 504 is located so as to obstruct the second opening portion 5012*b* or its vicinity at the second end 5011*b* of the cylindrical member 501. The second end 5011*b* side may be, for example, the second end 5011*b*, or may be the vicinity of the second end 5011*b*. The state in which the second filter 504 obstructs the cylindrical member 501 refers to, for example, a state in which the second filter 504 is provided such that the contents of the cylindrical member 501 do not migrate from the second end 5011*b* to the outside without passing through the second filter 504. If the cylindrical member 501 is obstructed by the second filter 504, for example, the contents of the cylindrical member 501 that can pass through the second filter 504 can migrate between the inside and the outside of the cylindrical member 501 via the second opening portion 5012*b* on the second end 5011*b* side through the second filter 504. The contents are a concept that encompasses those that are supplied as the contents of the cylindrical member 501.

The second filter 504 may be located at a point whose position in the axial direction is closer to the first end 5011*a* than the second end 5011*b* is, and may be located closer to the first end 5011*a* than the second end 5011*b* is, for example, within the range where the distance from the second end 5011*b* is 3 cm or less, and preferably 1 cm or less. In this example, the second filter 504 is laid over the first end 5011*a* side of the second reflecting member 505, which will be described later. Accordingly, the second filter 504 is located closer to the first end 5011*a* than the second end 5011*b* is by the thickness of the second reflecting member 505.

The second filter 504 may be located so as to obstruct the second end 5011*b* of the cylindrical member 501. The state of being located so as to obstruct the second end 5011*b* refers to, for example, a state in which the second filter 504 is located at the second opening portion 5012*b* at the second end 5011*b* such that the second opening portion 5012*b* at the second end 5011*b* is obstructed by the second filter 504.

The second reflecting member 505 is a member through which at least the contents having passed through the second filter 504 (e.g., the contents after removing solid-phase resins with the second filter 504) can pass, and that reflects microwaves. The second reflecting member 505 may be, for example, similar to the first reflecting member 503 described above, and thus a detailed description thereof has been omitted. In this example, a case will be described as an example in which the second reflecting member 505 is a flat plate-like member made of a microwave-reflecting material, and having multiple holes that can reflect microwaves having been introduced into the cylindrical member 501, and through which at least the contents of the cylindrical member 501 having passed through the second filter 504 (e.g., the contents after removing solid-phase resins) can pass.

The second reflecting member 505 may be the same as or different from the first reflecting member 503. For example, the material of the second reflecting member 505 may be the same as or different from the material of the first reflecting member 503, as long as it is a microwave-reflecting material. For example, the multiple holes of the second reflecting member 505 may be holes with the size, the shape, and the like that are the same as or different from those of the holes 503*a* of the first reflecting member 503, as long as their size, shape, and the like allow the contents after removing solid-phase resins used for solid-phase synthesis to pass through the holes.

The second reflecting member 505 is located so as to obstruct the second end 5011*b* of the cylindrical member 501. The state of being located so as to obstruct the second end 5011*b* refers to, for example, a state in which the second reflecting member 505 is located at the second opening portion 5012*b* at the second end 5011*b* of the cylindrical member 501 such that the second opening portion 5012*b* at the second end 5011*b* is obstructed by the second reflecting member 505. The state in which the second reflecting member 505 is located so as to obstruct the second end 5011*b* of the cylindrical member 501 may be considered, for example, as a state in which the second reflecting member 505 is located at the cylindrical member 501 such that microwaves having been introduced into the cylindrical member 501 do not pass through the second opening portion 5012*b* at the second end 5011*b* to the outside. The state in which the second reflecting member 505 obstructs the cylindrical member 501 may refer to, for example, a state in which the second reflecting member 505 is provided such that the contents of the cylindrical member 501 do not migrate from the second end 5011*b* to the outside without passing through the second reflecting member 505. If the cylindrical member 501 is obstructed by the second reflecting member 505, for example, the contents of the cylindrical member 501 that can pass through the second reflecting member 505 can migrate between the inside and the outside of the cylindrical member 501 via the second opening portion 5012*b* on the second end 5011*b* side through the second reflecting member 505. The contents are a concept that encompasses those that are supplied as the contents of the cylindrical member 501.

The second filter 504 is laid over the first end 5011*a* side of the second reflecting member 505. The second filter 504 is located on the surface on the first end 5011*a* side of the second reflecting member 505.

The second reflecting member 505 may be located at a point whose position in the axial direction is closer to the first end 5011*a* than the second end 5011*b* is. For example, the second reflecting member 505 may be located closer to the first end 5011*a* than the second end 5011*b* is, within the range where the distance from the second end 5011*b* is 3 cm or less, and preferably 1 cm or less. That is to say, it is sufficient that the second reflecting member 505 is located so as to obstruct the second end 5011*b* side of the cylindrical member 501. The state in which the second reflecting member 505 is located so as to obstruct the second end 5011*b* side refers to a state in which the second reflecting member 505 is located so as to obstruct the second opening portion 5012*b* or its vicinity at the second end 5011*b*. The second end 5011*b* side may be, for example, the second opening portion 5012*b* at the second end 5011*b*, or may be the vicinity thereof.

Furthermore, the planar shape of the second reflecting member 505 may have, for example, any shape and any size that allow the second opening portion 5012*b* at the second end 5011*b* to be obstructed.

The first reflecting member 503 and the second reflecting member 505 are preferably attached to the cylindrical member 501 such that microwaves having been introduced into the cylindrical member 501 are confined inside the cylindrical member 501 without leaking to the outside.

The state in which the first filter 502 is located so as to obstruct the first end 5011*a* side of the cylindrical member 501 may be considered as a mode in which the first filter 502 and the first reflecting member 503 are located so as to partition the cylindrical member 501, and may be considered, for example, as a state in which the first filter 502 is located so as to define the inside of the cylindrical member 501 and the outside of the cylindrical member 501. The state in which the first filter 502 is located so as to define the regions refers to, for example, a state in which the first filter 502 is provided between the two regions defined by the first filter 502 such that the contents of the cylindrical member 501 do not migrate without passing through the first filter 502. The same applies to the states in which the first reflecting member 503 is located so as to obstruct the first end 5011a side of the cylindrical member 501, in which the second filter 504 is located so as to obstruct the second end 5011b side of the cylindrical member 501, and in which the second reflecting member 505 is located so as to obstruct the second end 5011b side of the cylindrical member 501.

The column 5 may be a column that can be disassembled and assembled. For example, the cylindrical member 501 may be composed of two or at least three detachable cylindrical members, wherein the first filter 502 and the first reflecting member 503 may be attached to the member (not shown) having the first end 5011a among these members, and the second filter 504 and the second reflecting member 505 may be attached to the member (not shown) having the second end 5011b among the disassembled members. The structure for making the cylindrical members detachable is a known technique, and thus a detailed description thereof has been omitted. For example, portions for linking the cylindrical members may be provided with joints or the like. At least one of the pair of the first filter 502 and the first reflecting member 503 and the pair of the second filter 504 and the second reflecting member 505 may be detachable from the column 5. The structure for making the filters and the like detachable is a known technique, and thus a detailed description thereof has been omitted. If the column 5 has a detachable structure in this manner, solids such as solid-phase resins that cannot pass through the first filter 502 and the second filter 504 can be placed into the region in the cylindrical member 501 between the first filter 502 and the second filter 504.

Furthermore, the side face of the cylindrical member 501 or the like may be provided with an openable cover, stopper (not shown) or the like used to place solid-phase resins or the like.

Figure 11A:
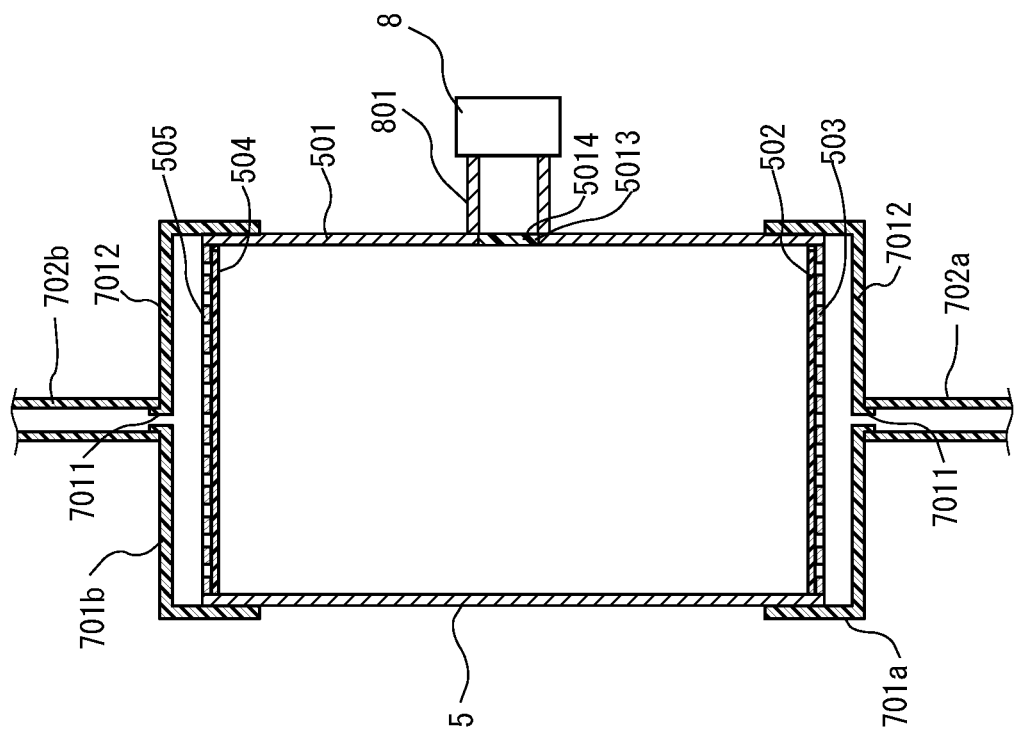
FIG. 11 shows a perspective view of a main portion in a state in which the column according to in Embodiment 5 of the present invention has been attached to an apparatus used for treatment (FIG. 11A), and a cross-sectional view thereof taken along the line XIb-XIb (FIG. 11B).
Figure 11B:
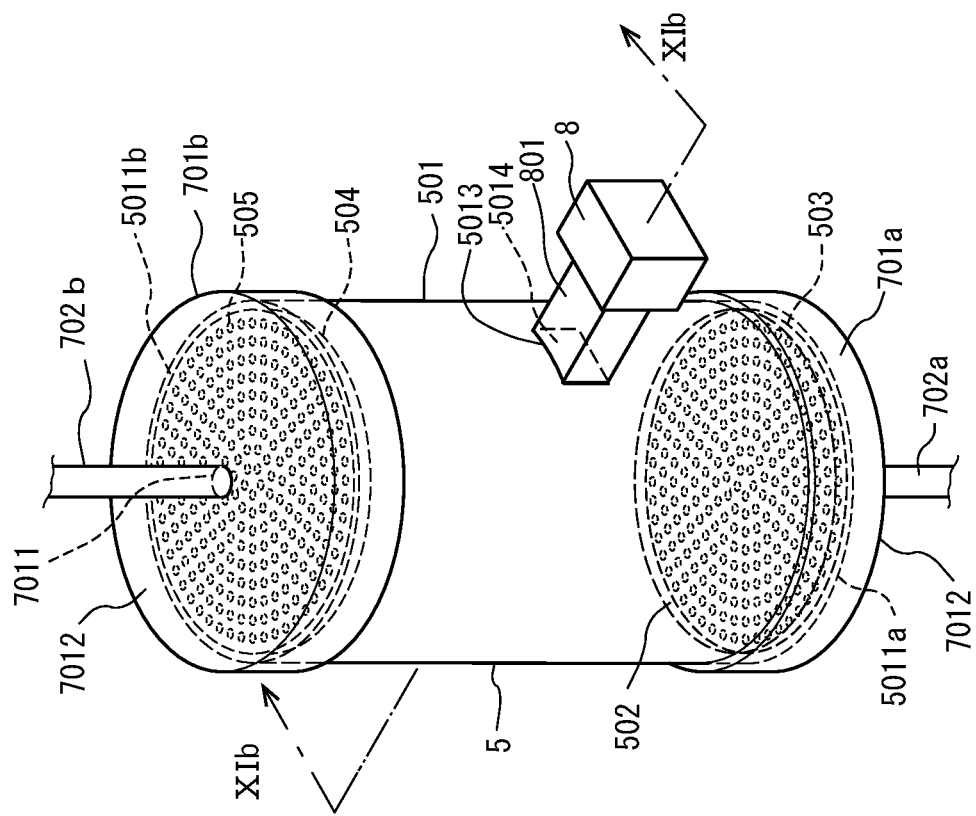

FIG. 11 shows a perspective view showing a state in which the column 5 of this embodiment has been attached to the main portion of an apparatus used for solid-phase synthesis (FIG. 11A), and a cross-sectional view thereof taken along the line XIb-XIb (FIG. 11B).

Next, an example of the method for attaching the column 5 of this embodiment to an apparatus used for solid-phase synthesis will be described with reference to FIG. 11. A first cap 701a whose bottom face 7012 has an opening portion 7011 is attached so as to obstruct the first end 5011a side of the cylindrical member 501. The opening portion 7011 is located in order to supply and discharge liquids (e.g., a solution used for reactions, a washing liquid used for washing or the like, etc.) and gases used for treatment. The first cap 701a is attached such that no gap is formed between the first cap 701a and the side face of the cylindrical member 501. The first cap 701a and the cylindrical member 501 may be provided with joints (not shown). A second cap 701b similar to the first cap 701a is attached so as to obstruct the second end 5011b side of the cylindrical member 501 of the column 5. A tube 702a for supplying and discharging liquids, gases, and the like used for treatment is attached to the opening portion 7011 of the first cap 701a. A tube 702b for supplying and discharging liquids, gases, and the like used for treatment is attached to the opening portion 7011 of the second cap 701b. Then, for example, a pump (not shown), a valve (not shown), or a vessel (not shown) in which liquids, gases, and the like have been placed is connected to at least one of the tube 702a and the tube 702b.

For example, liquids and gases can be supplied into the column 5 by supplying liquids, gases, and the like using a pump or the like from the tube 702a to the first cap 701a. The liquids and gases that are the contents inside the column 5 can be discharged from the opening portion 7011 of the second cap 701b via the tube 702b. It is possible to cause the contents of the column 5 to continuously flow through the column 5, by supplying liquids and gases from the tube 702a and discharging the contents of the column 5 from the tube 702b.

In a similar manner, for example, liquids and gases can be supplied into the column 5 by supplying liquids, gases, and the like from the tube 702b to the second cap 701b. The liquids and gases that are the contents inside the column 5 can be discharged from the opening portion 7011 of the first cap 701a via the tube 702a.

It is possible to cause the contents of the column 5 to continuously flow through the column 5, by supplying liquids and gases from the tube 702b and discharging the contents of the column 5 from the tube 702a. The inside of the column 5 is, for example, a portion inside the cylindrical member 501, or a region that is located between the pair of the first filter 502 and the first reflecting member 503 and the pair of the second filter 504 and the second reflecting member 505 inside the cylindrical member 501. The region in this case may be considered as a space.

The first cap 701a and the second cap 701b may be made of any material. Examples thereof include microwave-transmitting materials such as synthetic resins, and microwave-reflecting materials such as metals such as stainless steel.

Furthermore, instead of attaching the first cap 701a connected to the tube 702a and the second cap 701b connected to the tube 702b to the cylindrical member 501, a pipe (not shown) through which the contents can be supplied and discharged may be directly connected to each of the first end 5011a and the second end 5011b of the cylindrical member 501.

A waveguide 801 connected to a microwave oscillator 8 is connected to the introduction port 5013 of the cylindrical member 501. There is no limitation on the manner in which the introduction port 5013 and the end of the waveguide 801 are connected to each other. For example, it is possible to provide a portion on the outside of the cylindrical member 501 and on the outer perimeter of the introduction port 5013 with a joint or the like, and to connect the waveguide 801 and the introduction port 5013 through the joint. It is also possible to fasten a flange provided at the end of the waveguide 801 to a portion around the introduction port 5013 on the side face of the cylindrical member 501 using a screw. If the connection is performed in this manner, the microwaves emitted by the microwave oscillator 8 can be supplied via the waveguide 801 and the introduction port 5013 into the column 5. A sealing member (not shown) or the like for preventing leakage of microwaves is preferably provided between the waveguide 801 and the cylindrical member 501. As long as the opening portion of the waveguide 801 is located so as to cover the introduction port 5013, the waveguide 801 does not absolutely have to be attached to the cylindrical member 501, and the column 5, the waveguide 801, and the like may be located such that the end on the cylindrical member 501 side of the waveguide 801 is in contact with the portion around the introduction port 5013 of the cylindrical member 501.

Furthermore, in this example, the introduction port 5013 is connected to the microwave oscillator 8 via the waveguide 801, but a coaxial cable and an antenna or the like may be used instead of the waveguide 801 to connect the introduction port 5013 to the microwave oscillator 8. A portion of the column 5 provided with the introduction port 5013 may be located inside a waveguide (not shown) connected to the microwave oscillator 8.

There is no limitation on the microwave oscillator 8 connected to the column 5, and, furthermore, there is no limitation on the frequency, the intensity, and the like of microwaves that are emitted by the microwave oscillator 8. The microwave oscillator 8 is, for example, a microwave oscillators 8 having magnetrons, klystrons, gyrotrons, semiconductor oscillators, or the like. The frequency of microwaves that are emitted by the microwave oscillator 8 may be, for example, 915 MHz, 2.45 GHz, 5.8 GHz, or other frequencies ranging from 300 MHz to 300 GHz. As the waveguide 801, for example, a waveguide according to the frequency of microwaves that are emitted by the microwave oscillator 8 and the like is used.

The above-described connection with an apparatus is merely an example, and the column 5 may be connected in any manner according to the apparatus to which the connection is to be established.

Hereinafter, solid-phase synthesis treatment of peptides using the column 5 in Embodiment 5 will be briefly described. It is possible to perform solid-phase synthesis similar to the solid-phase synthesis of peptides performed using the treatment apparatus 3 in Embodiment 3 above, by attaching the column 5 in Embodiment 5 to an apparatus as shown in FIG. 11 for performing solid-phase synthesis. In this case, solid-phase synthesis as in the specific examples of Embodiment 3 above and the like can be performed in the cylindrical member 501, for example, by changing the specific examples of Embodiment 3 above and the like such that the solid-phase resins and the like are placed into the region between the first filter 502 and the second filter 504 of the column 5 instead of into the region between the first filter 105 and the second filter 107 of the treatment apparatus 3, the contents such as liquids are supplied from the tube 702*b* shown in FIG. 11 instead of from the second opening portion 1011*b* of the treatment apparatus 3, and the contents are discharged from the tube 702*a* shown in FIG. 11 instead of from the first opening portion 1011*a* of the treatment apparatus 3. The supply of the contents from the tube 702*b*, the discharge of the contents from the tube 702*a*, and the like may be controlled, for example, by pumps, valves, and the like (not shown) attached to the tube 702*b* and the tube 702*a*. The contents used for treatment, the order of steps in the treatment, the number of repetitions of the treatment, and the like are as in the specific examples of Embodiment 3 above and the like, and thus a detailed description thereof has been omitted.

One or more sessions of the treatment performed in the above-described solid-phase synthesis may be performed while causing the contents such as liquids to flow inside the column or while not causing the contents to flow.

One or more sessions of the above-described solid-phase synthesis treatment may be performed while stirring liquids inside the column 5 with air bubbles generated by gas supplied via a nozzle (not shown) or the like, the nozzle being provided for supplying gas such as nitrogen gas to the column 5.

Furthermore, the solid-phase synthesis treatment of peptides using the column in Embodiment 5 above is merely an example, and solid-phase synthesis of peptides other than those described above also may be performed.

As described above, in this embodiment, since the first reflecting member 503 and the second reflecting member 505 are provided inside the cylindrical member 501 made of a microwave-reflecting material, so as to obstruct the first end 5011*a* side and the second end 5011*b* side that are open, and, furthermore, since microwaves can be introduced from the introduction port 5013 of the cylindrical member 501 into the cylindrical member 501, microwaves having been introduced into the cylindrical member 501 can be made unlikely to be transmitted to the outside of the cylindrical member 501, and thus it is possible to efficiently perform microwave irradiation. Accordingly, for example, it is possible to increase the throughput through microwave irradiation.

Furthermore, since the first end 5011*a* and the second end 5011*b* are obstructed by the first filter 502, the first reflecting member 503, the second filter 504, and the second reflecting member 505 through which at least part of the contents can pass, it is possible to perform treatment through microwave irradiation while causing the contents to flow inside the cylindrical member 501 from the first end 5011*a* toward the second end 5011*b*, and to perform treatment while causing the contents to flow inside the cylindrical member 501 from the second end 5011*b* toward the first end 5011*a*, and thus it is possible to flexibly perform various types of treatment. Since the first end 5011*a* and the second end 5011*b* are respectively obstructed by the first filter 502 and the second filter 504 in whichever direction the contents flow, the solid-phase resins that are to be separated, among the contents of the cylindrical member 501, can be prevented from flowing out of the cylindrical member 501.

Furthermore, in the column 5 of this embodiment, the first filter 502 is laid over the first reflecting member 503 made of a reflecting material such as a metal, and thus the first reflecting member 503 can reinforce and support the first filter 502. Accordingly, for example, the first filter 502, the sheet-like first filter 502, or the like, for which it is difficult to be located alone so as to partition the cylindrical member 501 due to low hardness of the material thereof, can be located so as to partition the interior portion of the cylindrical member 501. Accordingly, it is possible to widen the range of choice of the first filter 502.

Furthermore, in a similar manner, the second filter 504 is laid over the second reflecting member 505 made of a reflecting material such as a metal, and thus the second reflecting member 505 can reinforce and support the second filter 504. Accordingly, for example, the second filter 504, the sheet-like second filter 504, or the like, for which it is difficult to be located alone so as to partition the cylindrical member 501 due to low hardness of the material thereof, can be located so as to partition the interior portion of the cylindrical member 501. Accordingly, it is possible to widen the range of choice of the second filter 504.

First Modified Example

FIGS. 12A to 12C show cross-sectional views illustrating a first modified example of the column of this embodiment, and are cross-sectional views corresponding to FIG. 9B.

In the foregoing embodiment, a case was described in which the first filter 502 is laid over the second end 5011*b* side of the first reflecting member 503, but the first filter 502 may not be directly laid over the first reflecting member 503, as long as the first filter 502 is located closer to the second end 5011*b* than the first reflecting member 503 is.

For example, it is also possible to locate the first filter 502 and the first reflecting member 503 such that they are not directly laid over each other as shown in FIG. 12A. Also in this case, microwaves having been transmitted through the first filter 502 are reflected by the first reflecting member 503, so that the microwaves are prevented from being transmitted to the outside from the first opening portion 5012a at the first end 5011a. Accordingly, it is possible to efficiently use microwaves for solid-phase synthesis.

Furthermore, instead of locating the first filter 502 closer to the second end 5011b than the first reflecting member 503 is, it is also possible to locate the first filter 502 closer to the first end 5011a than the first reflecting member 503 is as shown in FIG. 12B. Also in this case, the first reflecting member 503 reflects microwaves, and microwaves can be made unlikely to be transmitted from the first opening portion 5012a at the first end 5011a of the cylindrical member 501, and thus it is possible to efficiently use microwaves. FIG. 12B shows an example in which the first filter 502 is located at the first opening portion 5012a at the first end 5011a. In this case, the first filter 502 can prevent the solid-phase resins inside the cylindrical member 501 from migrating to the outside from the first opening portion 5012a at the first end 5011a of the cylindrical member 501, and thus the first reflecting member 503 may be a member through which the solid-phase resins can pass. For example, as the first reflecting member 503, a member having multiple holes with a shape and a size that allow the solid-phase resins to pass through the holes is used. Note that, in this case, the contents containing the solid-phase resins between the first reflecting member 503 and the first filter 502 are unlikely to be irradiated with microwaves, and thus, if the distance between the first reflecting member 503 and the first filter 502 increases, the efficiency of the solid-phase synthesis treatment may deteriorate. Furthermore, in this case, the first filter 502 may be made of a material other than microwave-transmitting materials.

Furthermore, as a mode in the case in which the first filter 502 is located closer to the first end 5011a than the first reflecting member 503 is, it is also possible to locate the first reflecting member 503 so as to be laid over the face on the second end 5011b side of the first filter 502 as shown in FIG. 12C. FIG. 12C shows an example in which the first filter 502 is located at the first opening portion 5012a at the first end 5011a. In this case, it is possible to prevent the efficiency of solid-phase synthesis treatment from deteriorating as described above, by eliminating the distance between the first reflecting member 503 and the first filter 502, and the first filter 502 laid over the first reflecting member 503, and thus the first reflecting member 503 can reinforce and support the first filter 502. If the first filter 502 and the first reflecting member 503 are laid over each other as in the foregoing embodiment or FIG. 12C, the first filter 502 can be reinforced by the first reflecting member 503, and thus it is possible to widen the range of choice of the first filter 502.

Second Modified Example

FIGS. 13A to 13C show cross-sectional views illustrating a second modified example of the column of this embodiment, and are cross-sectional views corresponding to FIG. 9B.

For example, in the foregoing embodiment, a case was described in which the second filter 504 is laid over the second reflecting member 505, but the second filter 504 may not be directly laid over the second reflecting member 505, as long as the second filter 504 is located closer to the first end 5011a than the second reflecting member 505 is.

For example, it is also possible to locate the second filter 504 and the second reflecting member 505 such that they are not directly laid over each other as shown in FIG. 13A. Also in this case, microwaves having been transmitted through the second filter 504 are reflected by the second reflecting member 505, so that the microwaves are prevented from being transmitted to the outside from the second opening portion 5012b at the second end 5011b. Accordingly, it is possible to efficiently use microwaves for solid-phase synthesis. Note that, in this case, the contents not containing the solid-phase resins between the second filter 504 and the second reflecting member 505 are irradiated with microwaves, and thus it may not be possible to efficiently use microwaves compared with the case in which the second filter 504 is laid over the second reflecting member 505. In this case, the second filter 504 cannot be reinforced by the second reflecting member 505.

Furthermore, instead of locating the second filter 504 closer to the first end 5011a than the second reflecting member 505 is, it is also possible to locate the second filter 504 closer to the second end 5011b than the second reflecting member 505 is as shown in FIG. 13B. Also in this case, the second reflecting member 505 reflects microwaves, and microwaves can be made unlikely to be transmitted from the second opening portion 5012b at the second end 5011b of the cylindrical member 501, and thus it is possible to efficiently use microwaves. FIG. 13B shows an example is shown in which the second filter 504 is located at the second opening portion 5012b at the second end 5011b. In this case, the second filter 504 can prevent the solid-phase resins inside the cylindrical member 501 from migrating to the outside from the second opening portion 5012b on the second end 5011b side of the cylindrical member 501, and thus the second reflecting member 505 may be a member through which the solid-phase resins can pass. For example, as the second reflecting member 505, a member having multiple holes with a shape and a size that allow the solid-phase resins to pass through the holes may be used. Note that, in this case, the contents containing the solid-phase resins between the second reflecting member 505 and the second filter 504 are unlikely to be irradiated with microwaves. In this case, the second filter 504 may be made of a material other than microwave-transmitting materials.

Furthermore, as a mode in the case in which the second filter 504 is located closer to the second end 5011b than the second reflecting member 505 is, it is also possible to locate the second reflecting member 505 so as to be laid over the face on the first end 5011a side of the second filter 504 as shown in FIG. 13C. FIG. 13C shows an example in which the second filter 504 is located at the second opening portion 5012b at the second end 5011b. In this case, it is possible to prevent the efficiency of solid-phase synthesis treatment from deteriorating as described above, by eliminating the distance between the second reflecting member 505 and the second filter 504, and the second filter 504 is laid over the second reflecting member 505, and thus the second reflecting member 505 can reinforce and support the second filter 504. If the second filter 504 and the second reflecting member 505 are laid over each other as in the foregoing embodiment or FIG. 13C, the second filter 504 can be reinforced by the second reflecting member 505, and thus it is possible to widen the range of choice of the second filter 504.

As the second filter 504 and the second reflecting member 505 of the column in Embodiment 5 above and the first modified example thereof, it is possible to use any one combination of the second filter 504 and the second reflecting member 505 described with reference to FIGS. 13A to 13C in the second modified example. As the first filter 502 and the first reflecting member 503 in Embodiment 5 above and the second modified example thereof, it is possible to use any one combination of the first filter 502 and the first reflecting member 503 described with reference to FIGS. 12A to 12C in the first modified example. For example, it is sufficient that the column 5 includes any one combination of the first filter 502 and the first reflecting member 503 described in Embodiment 5 above and the first modified example thereof and any one combination of the second filter 504 and the second reflecting member 505 described in Embodiment 5 above and the second modified example thereof.

Embodiment 6

A column of this embodiment is different from the column 5 described in Embodiment 5 above in that a filter that reflects microwaves is used instead of each of the first filter 502 and the first reflecting member 503, and the second filter 504 and the second reflecting member 505.

Figure 14B:
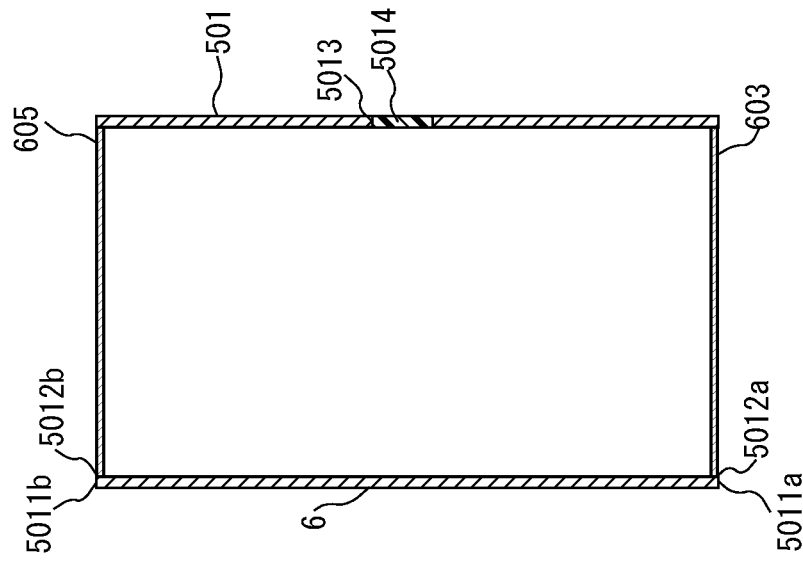
FIG. 14 shows a perspective view showing an example of a column according to Embodiment 6 of the present invention (FIG. 14A), and a cross-sectional view thereof taken along the line XIVb-XIVb (FIG. 14B).
Figure 14A:
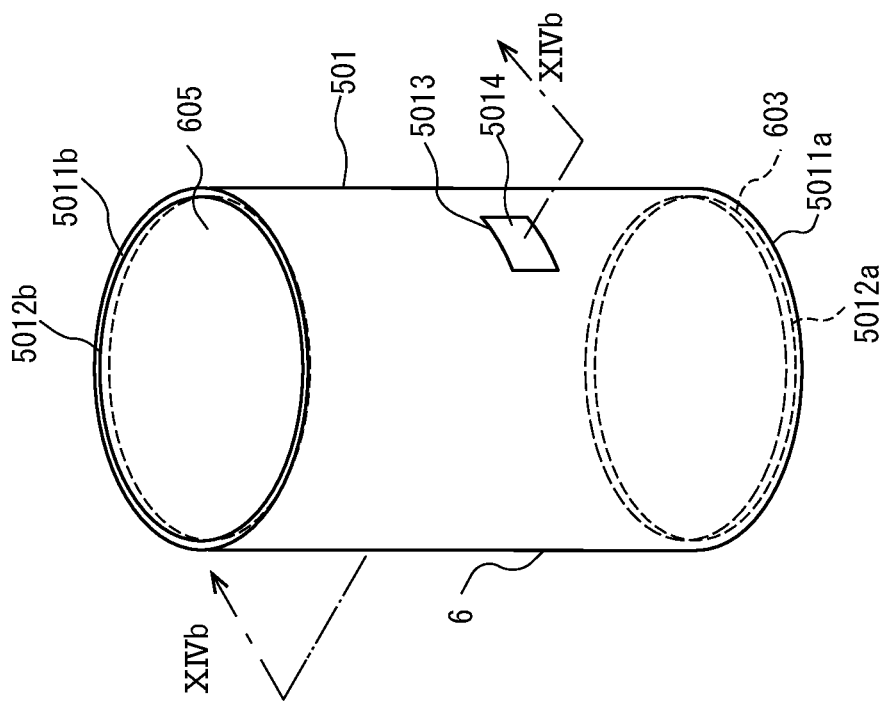

FIG. 14 shows a perspective view showing an example of a column in this embodiment (FIG. 14A), and a cross-sectional view thereof taken along the line XIVb-XIVb (FIG. 14B). In FIG. 14B, a cross-section of valves and the like have been omitted.

A column 6 of this embodiment includes the cylindrical member 501, a first reflecting filter 603, and a second reflecting filter 605. The cylindrical member 501 has the first end 5011a, the second end 5011b, the introduction port 5013, and the microwave-transmitting member 5014. The constituent elements other than the first reflecting filter 603 and the second reflecting filter 605 are as in Embodiment 5 above, and thus a detailed description thereof has been omitted.

The first reflecting filter 603 is a filter configured from the first filter 502 and the first reflecting member 503 together, and is a filter that separates solid-phase resins from the contents of the cylindrical member 501, and that reflects microwaves introduced from the introduction port 5013. The first reflecting filter 603 may be composed of, for example, a mesh made of a metal such as stainless steel, a metal filter obtained by integrating multiple metal meshes and the like by sintering them in an overlaid state, or the like. The first reflecting filter 603 may be similar to the first reflecting filter 205, and thus a detailed description thereof has been omitted.

The first reflecting filter 603 is located at the first end 5011a so as to obstruct the first end 5011a of the cylindrical member 501. Since the first reflecting filter 603 is configured from the first filter 502 and the first reflecting member 503 together, it is sufficient that the first reflecting filter 603 is located so as to obstruct the first end 5011a side of the cylindrical member 501 as in the case of the first filter 502 and the first reflecting member 503. For example, it is sufficient that the first reflecting filter 603 is located closer to the second end 5011b than the first end 5011a is. For example, the first reflecting filter 603 may be located closer to the second end 5011b than the first end 5011a is, within the range where the distance from the first end 5011a is 3 cm or less, and preferably 1 cm or less.

The second reflecting filter 605 is a filter configured from the second filter 504 and the second reflecting member 505 together, and is a filter that separates solid-phase resins from the contents of the cylindrical member 501, and that reflects microwaves introduced into the cylindrical member 501 from the introduction port 5013. The second reflecting filter 605 may be similar to the first reflecting filter 603. The first reflecting filter 603 and the second reflecting filter 605 may be the same or different from each other.

The second reflecting filter 605 is located at the second end 5011b so as to obstruct the second end 5011b of the cylindrical member 501. Since the second reflecting filter 605 is configured from the second filter 504 and the second reflecting member 505 together, it is sufficient that the second reflecting filter 605 is located so as to obstruct the second end 5011b side of the cylindrical member 501 as in the case of the second filter 504 and the second reflecting member 505. For example, it is sufficient that the second reflecting filter 605 is located closer to the first end 5011a than the second end 5011b is. For example, the second reflecting filter 605 may be located closer to the first end 5011a than the second end 5011b is, within the range where the distance from the second end 5011b is 3 cm or less, and preferably 1 cm or less.

If it is difficult to locate the first reflecting filter 603 alone inside the cylindrical member 501, a frame or the like for reinforcement may be attached to the first reflecting filter 603. The same applies to the second reflecting filter 605.

Also in this embodiment, as in the foregoing embodiments, microwaves having been introduced into the cylindrical member 501 can be made unlikely to be transmitted to the outside of the cylindrical member 501, and thus it is possible to efficiently perform microwave irradiation. Since the first reflecting filter 603 and the second reflecting filter 605 are provided, it is possible to separate solid-phase resins from the contents.

Furthermore, since the first end 5011a and the second end 5011b are obstructed by the first reflecting filter 603, and the second reflecting filter 605 through which at least part of the contents can pass, it is possible to perform treatment through microwave irradiation while causing the contents to flow inside the cylindrical member 501 from the first end 5011a toward the second end 5011b, and to perform treatment while causing the contents to flow inside the cylindrical member 501 from the second end 5011b toward the first end 5011a, and thus it is possible to flexibly perform various types of treatment. Since the first end 5011a and the second end 5011b are respectively obstructed by the first reflecting filter 603 and the second reflecting filter 605 in whichever direction the contents flow, the solid-phase resins that are to be separated, among the contents of the cylindrical member 501, can be prevented from flowing out of the cylindrical member 501.

The first reflecting filter 603 in Embodiment 6 above may be used instead of the first filter 502 and the first reflecting member 503 of the column 5 as shown in FIGS. 9 and 13A to 13C described in Embodiment 5 and the second modified example thereof, and the second reflecting filter 605 in Embodiment 6 above may be used instead of the second filter 504 and the second reflecting member 505 of the column 5 as shown in FIGS. 9 and 12A to 12C described in Embodiment 5 and the first modified example thereof. For example, it is sufficient that the column includes either the combination of the first filter 502 and the first reflecting member 503 described in Embodiment 5 above and the first modified example thereof or the first reflecting filter 603, and either the combination of the second filter 504 and the second reflecting member 505 described in Embodiment 5 above and the second modified example thereof or the second reflecting filter 605.

In the foregoing embodiments, there is no limitation on the position at which the introduction port 5013 is provided, as long as it is on the side face of the cylindrical member 501 between the first reflecting member 503 and the second reflecting member 505. The positions of the introduction port 5013, the first reflecting member 503, and the second reflecting member 505 are, for example, positions in the axial direction of the cylindrical member 501. In the case of using the first reflecting filter 603 instead of the first filter 502 and the first reflecting member 503, the first reflecting member 503 described above may be read as the first reflecting filter 603. In a similar manner, in the case of using the second reflecting filter 605 instead of the second filter 504 and the second reflecting member 505, the second reflecting member 505 described above may be read as the second reflecting filter 605.

For example, in the case in which the first reflecting member 503 is located closer to the first end 5011*a* than the first filter 502 is, and the first reflecting member 503 and the first filter 502 are located away from each other so as not to be laid over each other as shown in FIG. 12A, the introduction port 5013 may be provided between the first filter 502 and the first reflecting member 503.

Furthermore, in the case in which the second reflecting member 505 is located closer to the second end 5011*b* than the second filter 504 is, and the second reflecting member 505 and the second filter 504 are located away from each other so as not to be laid over each other as shown in FIG. 13A, the introduction port 5013 may be provided between the second filter 504 and the second reflecting member 505.

Furthermore, in Embodiments 5 and 6 above, an examples was described in which the cylindrical member 501 used as a vessel includes the introduction port 5013, and microwaves are introduced (i.e., emitted) from the introduction port 5013 into the cylindrical member 501, but it is sufficient that the cylindrical member 501 includes an emitting portion (not shown) of microwaves in the irradiation that is performed into the cylindrical member 501 so that microwave irradiation is performed from this emitting portion into the cylindrical member 501. The emitting portion of microwaves is a portion that emits microwaves in the irradiation performed into the cylindrical member 501. The emitting portion may have, for example, any structure and any shape, as long as microwaves in the irradiation performed by the irradiation unit or the like can be emitted (i.e., introduced) into the cylindrical member 501. The emitting portion may be considered, for example, as the introduction port 5013 in Embodiments 5 and 6 above. The position of the emitting portion may be considered as the microwave emitting positions described above. A description of a positional relationship of the first filter 502, the first reflecting member 503, the second filter 504, the second reflecting member 505, and the like relative to the introduction port 5013 may be read as a description of a positional relationship relative to the emitting positions.

Above, a case was described in which the column 5 is configured such that an emitting portion such as an introduction port is provided on the side face of the cylindrical member 501, the first filter 502 is located so as to obstruct the first end 5011*a* side of the cylindrical member 501, the first reflecting member 503 is located so as to obstruct the first end 5011*a* side of the cylindrical member 501, the second filter 504 is located so as to obstruct the second end 5011*b* side of the cylindrical member 501, and the second reflecting member 505 is located so as to obstruct the second end 5011*b* side of the cylindrical member 501, but it is sufficient that the column 5 is configured such that, for example, the first filter 502 is located so as to partition the cylindrical member 501 used as a vessel, the first reflecting member 503 is located closer to the first end 5011*a* than the emitting position is and so as to partition the cylindrical member 501, the emitting position is located between the first end 5011*a* and the second end 5011*b*, the second filter 504 is located closer to the second end 5011*b* than the first filter 502 and the first reflecting member 503 are and so as to partition the cylindrical member 501, and the second reflecting member 505 is located closer to the second end 5011*b* than the first filter 502 and the emitting position are and so as to partition the cylindrical member 501. The emitting position may be considered, for example, as the position in the axial direction at which the emitting portion such as the introduction port 5013 is provided. In this case, the first filter 502 or the first reflecting member 503 may be attached to the first opening portion 5012*a*, and the second filter 504 or the second reflecting member 505 may be attached to the second opening portion 5012*b*. Also in this case, microwaves in the irradiation performed into the cylindrical member 501 can be made unlikely to be emitted to the outside from the cylindrical member 501, the first reflecting member 503, and the second reflecting member 505, and thus it is possible to efficiently perform microwave irradiation. Also in this case, solids such as solid-phase resins that are to be separated may be supplied, for example, to the region between the first filter 502 and the second filter 504.

Furthermore, for example, it is sufficient that the column 6 is configured such that the first reflecting filter 603 is located closer to the first end 5011*a* than the emitting position is and so as to partition the cylindrical member 501, the emitting position is located between the first end 5011*a* and the second end 5011*b*, and the second reflecting filter 605 is located closer to the second end 5011*b* than the emitting position is and so as to partition the cylindrical member 501.

A column such as the columns 5 and 6 described in Embodiments 5 and 6 above may be considered as being used in a state in which it is attached to a treatment apparatus for performing solid-phase synthesis or other types of treatment as shown in FIG. 11, or may be considered as constituting part of such a treatment apparatus. For example, an apparatus in which an irradiation unit having the microwave oscillator 8, the waveguide 801, and the like is attached to the column 5 or 6 may be considered as a treatment apparatus. The columns such as the columns 5 and 6 may be considered as a treatment apparatus for performing solid-phase synthesis, other types of treatment, and the like.

There is no limitation on the number of amino acids synthesized in one peptide synthesized through solid-phase synthesis using the treatment apparatus or the column described in the foregoing embodiments, as long as it is two or more. For example, the number of amino acids synthesized in one peptide may be two or more and less than 20, 20 or more and less than 50, or 50 or more. For example, the peptide that is synthesized through solid-phase synthesis using the treatment apparatus or the column described in the foregoing embodiments may be oligopeptide in which the number of amino acids synthesized is two or more and less than about 20, or may be polypeptide in which the number of amino acids synthesized is about 20 or more. The peptide that is synthesized may be protein, which is a type of polypeptide in which about 50 or more amino acids are bound. There is no limitation on the type of amino acids that are synthesized to one peptide, the sequence order of amino acids that are synthesized to one peptide, and the like.

Furthermore, the treatment apparatus or the column described in the foregoing embodiments may be used for the solid-phase synthesis of one or at least two peptides used to produce any substance. For example, the treatment apparatuses in Embodiments 1 and 2 above may be used for solid-phase synthesis of one or at least two peptides (e.g., oligopeptide or polypeptide) used to produce antibodies. For example, the treatment apparatus or the column in the foregoing embodiments may be used for solid-phase synthesis of one or at least two peptides used as a raw material of antibodies, or may be used for solid-phase synthesis of one or at least two peptides, or part thereof, constituting antibodies (e.g., one or at least two polypeptides, or part thereof, constituting antibodies).

Furthermore, the treatment apparatus or the column described in the foregoing embodiments may be used for treatment including solid-phase synthesis of peptides. For example, it is possible to perform solid-phase synthesis of any desired peptides using the treatment apparatus or the column described in the foregoing embodiments, and then to bind any desired substances (e.g., sugar, etc.) to the peptides obtained through the solid-phase synthesis using the treatment apparatus or the column. For example, the treatment apparatus or the column described in the foregoing embodiments may be used in solid-phase synthesis of glycopeptides.

In the foregoing embodiments, a case was described in which the treatment apparatus or the column is used for solid-phase synthesis for synthesizing peptides bound to solid-phase resins, but the treatment performed using the treatment apparatus or the column is not limited to solid-phase synthesis treatment of peptides, and may be treatment other than solid-phase synthesis of peptides. For example, the treatment apparatus or the column may be used for solid-phase synthesis other than solid-phase synthesis of peptides, or may be used for treatment other than solid-phase synthesis.

For example, the treatment apparatus or the column described in the foregoing embodiments may be used for treatment including a step of separating solids from the contents of the vessel 101, the vessel 301, or the cylindrical member 501, such as solid-phase synthesis. The solid that is separated from the contents is, for example, solids located between the first filter 105 and the second filter 107, solids located between the first reflecting filter 205 and the second reflecting filter 206, solids located between the first filter 502 and the second filter 504, and solids located between the first reflecting filter 603 and the second reflecting filter 605. For example, in the case in which the treatment apparatuses 1 to 4 and the columns 5 and 6 are used for treatment other than solid-phase synthesis of peptides including such a step of separating solids, the description related to the solid-phase resins of the treatment apparatuses 1 to 4 and the columns 5 and 6 in the foregoing embodiments may be read as a description related to solids that are to be separated. For example, the configuration that is determined according to the size of solid-phase resins in the foregoing embodiments may be changed to a configuration that is determined according to the size of solids that are to be separated.

For example, the first filter 105, the second filter 107, the first reflecting filter 205, and the second reflecting filter 206 of the treatment apparatuses described in the foregoing embodiments, or the first filter 502, the second filter 504, the first reflecting filter 603, and the second reflecting filter 605 of the columns 5 and 6 described in the foregoing embodiments may be used as a filter having multiple holes for separating solids that are to be separated, so that the treatment apparatus or the column can be used for treatment including a step of separating solids that are to be separated from the contents of the vessel 101, the vessel 301, or the cylindrical member 501.

The contents of the vessel 101 and the cylindrical member 501 are, for example, contents having a liquid. The liquid of the contents may be, for example, a material that is to be treated such as a raw material, may be solvent or the like, and there is no limitation on components thereof. The liquid may be, for example, a solution in which a substance is dissolved in solvent or the like. The contents of the vessel 101 may contain, for example, a liquid and solids that are to be separated. The contents may be, for example, a suspension of solids that are to be separated. The solid is, for example, a material in a solid state. The solid may be considered as a material that is not flowable, and that can be separated through a filter or the like. For example, a gel may be considered as a solid. The solid that is to be separated preferably has, for example, a shape and a size that allow the solid to be flowable in a liquid of the contents. The solids that are to be separated are, for example, solids in the shape of granules, small pieces, or powders.

The treatment apparatuses and the columns described in the foregoing embodiments are, for example, an apparatus that can be used for treatment including a step of performing microwave irradiation into a vessel or a cylindrical member, and a step of separating solids that are to be separated from the contents containing a liquid inside the vessel or the cylindrical member. The solid-phase synthesis of peptides also may be considered as an example of such treatment.

For example, even in the case in which treatment through microwave irradiation is performed on a region that is closer to the first end 1015a than the first filter 105 is inside the vessel 101 of the treatment apparatus 1, the solid in this region cannot be separated from the contents through the first filter 105 after the treatment, and be left in the vessel 101 as a product, an intermediate product, or the like obtained through the treatment. Accordingly, it may be meaningless to perform treatment on solids through microwave irradiation in this region. However, according to the configuration provided with the first reflecting member 106, the region that is closer to the first end 1015a than the first reflecting member 106 is, in the region that is closer to the first end 1015a than the first filter 105 for separating solids that are to be separated is, can be made unlikely to be irradiated with microwaves, and regions such as a region in which solids cannot be separated and a region in which solids do not exist can be made unlikely to be irradiated with microwaves, and thus it is possible to efficiently use microwaves. The same applies to the case in which the treatment apparatuses 2 to 4 and the columns 5 and 6 are used for treatment including a step of separating solids.

In the treatment apparatuses according to Embodiments 1 to 4 above, the solid that is to be separated using the first filter 105, the second filter 107, the first reflecting filter 205, and the second reflecting filter 206 may be, for example, solids contained in the contents before performing microwave irradiation and the like, or solids produced by performing microwave irradiation and the like in the vessel 101 or the vessel 301. The same applies to the solid that is to be separated using the first filter 502, the second filter 504, the first reflecting filter 603, and the second reflecting filter 605 of the columns according to Embodiments 5 and 6 above.

Examples of the solid that is to be separated, contained in the contents before performing microwave irradiation and the like, include solids used for treatment, such as a solid catalyst in a fluidized bed, a susceptor with a size and the like that allow the susceptor to be flowable, which is used to adjust the microwave absorptivity, an adsorbent that adsorbs other substances, and solid supports. Examples of the solid catalyst in a fluidized bed include a palladium on carbon (Pd/C) catalyst, a platinum on carbon (Pt/C) catalyst, a solid acid catalyst, a zeolite-based catalyst, and the like. The solid that is to be separated, contained in the contents before performing microwave irradiation and the like, may be solid impurities or the like.

Examples of the solid that is to be separated, produced by performing microwave irradiation and the like, include solids produced through a chemical reaction or the like from the liquid in the contents inside the vessel 101, the vessel 301, or the cylindrical member 501 in which microwave irradiation has been performed, and solids produced through solidification or crystal growth of the liquid in the contents inside the vessel 101, the vessel 301, or the cylindrical member 501 in which microwave irradiation has been performed.

Furthermore, examples of the solid produced by performing microwave irradiation and the like include solids produced through a chemical reaction or the like between solids contained in the contents before performing microwave irradiation and the like and other substances inside the vessel 101, the vessel 301, or the cylindrical member 501 in which microwave irradiation has been performed, solids obtained by degrading, through a chemical reaction or the like, solids contained in the contents before performing microwave irradiation and the like inside the vessel 101, the vessel 301, or the cylindrical member 501 in which microwave irradiation has been performed, and solids produced through adsorption, adhesion, or growth of a same substance or different substances by performing microwave irradiation on the surface of solids contained in the contents before performing microwave irradiation and the like. The other substances and the same substance may be solids, a liquid, or a gas. The solid contained in the contents before performing microwave irradiation and the like is preferably placed into the region in the vessel 101 between the first filter 105 and the second end 1015b or between the first reflecting filter 205 and the second end 1015b, into the region in the vessel 301 between the first filter 105 and the second filter 107 or between the first reflecting filter 205 and the second reflecting filter 206, or into the region in the cylindrical member 501 between the first filter 502 and the second filter 504 or between the first reflecting filter 603 and the second reflecting filter 605.

Examples of the solid that is to be separated include materials that are to be treated, such as solids that are to be treated using the treatment apparatus or the column in the foregoing embodiments or solids that are produced through treatment, solids that are used for treatment such as a catalyst or a susceptor, unnecessary materials, or mixtures of two or more thereof. There is no limitation on the size and the like of the solid that is to be separated. The solid that is to be separated may be, for example, a precipitate. The solid that is to be separated may be a suspended matter or a sediment in the contents. The solid that is to be separated in the case in which the treatment performed in the treatment apparatus or the column is solid-phase synthesis of peptides is, for example, solid-phase resins.

It is sufficient that the treatment that separates solids from the contents performed using the above-described treatment apparatuses 1 to 4 is, for example, treatment including one or more steps of separating solids that are to be separated, from the contents. For example, the treatment performed using the treatment apparatuses 1 to 4 may be treatment that performs, once or more, at least one of the set of a step of performing microwave irradiation on the contents containing a liquid, a step of separating solids that are to be separated, from the contents using any one of the first filter 105, the second filter 107, the first reflecting filter 205, and the second reflecting filter 206 and then a step of adding a liquid or the like as the contents into the vessel 101, a step of performing microwave irradiation into the vessel 101, and a step of separating solids that are to be separated, from the contents using any one of the first filter 105, the second filter 107, the first reflecting filter 205, and the second reflecting filter 206, and the set of a step of adding a liquid or the like as the contents into the vessel 101, and a step of separating solids that are to be separated, from the contents using any one of the first filter 105, the second filter 107, the first reflecting filter 205, and the second reflecting filter 206. The same applies to treatment performed using the columns 5 and 6 as described above.

Hereinafter, specific examples in which the treatment apparatuses 1 to 4 described in the foregoing embodiments are used for treatment other than solid-phase synthesis of peptides will be described.

(A) Example of Use for Treatment for Producing Solid Using Solid and Liquid

The treatment apparatuses 1 to 4 described in the foregoing embodiments may be used, for example, for synthesis of zeolite through hydrothermal synthesis. For example, if a reaction is caused to occur under high-temperature and high-pressure hydrothermal conditions through microwave irradiation, in the presence of alkali (sodium hydroxide or potassium hydroxide) and water, using metallic aluminum, sodium aluminate, aluminum hydroxide, or the like as an Al (aluminum) source and further using a silica powder, a silica gel, or the like as an Si (silicon) source, a zeolite polycrystalline film of crystalline aluminosilicate can be produced. After the treatment is ended, if a zeolite polycrystalline film, which is solids, is separated using the first filter 105 or the first reflecting filter 205, the produced substance can be separated from the contents. In this case, as the first filter 105, the second filter 107, the first reflecting filter 205, and the second reflecting filter 206, a filter having multiple holes for separating a zeolite polycrystalline film, which is solids that are to be separated, is used.

(B) Example of Use for Treatment Using Solid Catalyst (B-1)

The treatment apparatuses 1 to 4 described in the foregoing embodiments may be used, for example, for treatment for producing methyl ester that can be used as a biodiesel fuel. For example, if a substance containing a large amount of fats and oils (triglyceride) such as used food oil, and a solid catalyst in a fluidized bed are placed into the vessel 101, and are irradiated with microwaves inside the vessel 101, transesterification of the substances and esterification of free fatty acid simultaneously occur in one vessel, and methyl ester is produced. The solid catalyst used in this example is, for example, a hybrid solid catalyst incorporating a substance having reaction active sites with respect to a substance with a large dielectric loss factor and a large magnetic loss factor suitable for microwaves that are to be emitted. In this treatment, if microwave irradiation is performed in a state in which a substance that is to be treated and the like are placed in the vessel 101, and a solid catalyst is placed above the first filter 105 or the first reflecting filter 205, and, after the production of the product is ended, the solid catalyst, which is solids, is separated using the first filter 105 or the first reflecting filter 205, the solid catalyst can be removed from the contents containing the produced substance.

As the first filter 105, the second filter 107, the first reflecting filter 205, and the second reflecting filter 206, a filter having multiple holes for separating solid catalyst, which is solids that are to be separated, is used. The same applies to other treatment using a solid catalyst in a fluidized bed as described below.

(B-2)

The treatment apparatuses 1 to 4 described in the foregoing embodiments may be used, for example, for a Pd (palladium) solid catalytic reaction typified by Suzuki-Miyaura coupling. This treatment is, for example, treatment for producing a substance having an aromatic ring-aromatic ring bond such as a biaryl compound, by causing cross coupling through microwave irradiation in solvent with low microwave absorbency such as toluene, using a Pd/C (palladium/carbon) solid catalyst in a fluidized bed in which metal Pd is supported on the surface of activated carbon or the like with high microwave absorbency, from a halogen compound and an organic boronic acid compound as raw materials. In this treatment, is microwave irradiation is performed in a state in which a substance that is to be treated and the like are placed in the vessel 101, and a solid catalyst is placed at a location similar to that of the above-described case of solid-phase resins, and, after the production of the product is ended, the solid catalyst, which is solids, is separated using the first filter 105 or the first reflecting filter 205, the solid catalyst can be removed from the contents containing the produced substance.

(B-3)

The treatment apparatuses 1 to 4 described in the foregoing embodiments may be used, for example, for a microwave irradiation solvent-free reaction using a wide surface of a solid-phase carrier such as alumina or silica gel. For example, if raw materials are mixed with a solid catalyst in a fluidized bed in which a porous solid-phase carrier such as alumina or silica gel, a catalyst, and a base are mixed, and are subjected to various organic syntheses through microwave irradiation in solvent-free conditions, various synthesis products can be obtained. In this treatment, if microwave irradiation is performed in a state in which a solid catalyst is placed at a location similar to that of the above-described case of solid-phase resins, and, after the production of the product is ended, the solid catalyst, which is solids, is separated using the first filter 105 or the first reflecting filter 205, the solid catalyst can be removed from the contents containing the produced substance.

(C) Example of Use for Treatment Using Microwave Susceptor

The treatment apparatuses 1 to 4 described in the foregoing embodiments may be used, for example, for synthesis using a microwave susceptor (solid) such as SiC (silicon carbide), carbon, or ferrite that is likely to absorb microwaves. For example, if heating is performed through microwave irradiation in the coexistence of raw materials and small pieces of a microwave susceptor in solvent such as toluene solvent with low microwave absorbency, various synthesis products can be obtained. In this treatment, if microwave irradiation is performed in a state in which raw materials are placed in the vessel 101, and a microwave susceptor is placed at a location similar to that of the above-described case of solid-phase resins, and, after the treatment is ended, the microwave susceptor, which is solids, is separated using the first filter 105 or the first reflecting filter 205, the microwave susceptor can be removed from the contents containing the produced substance. As the first filter 105, the first reflecting filter 205, the second filter 107 and the second reflecting filter 206 that are used in this example, a filter having multiple holes for separating a microwave susceptor, which is solids that are to be separated, is used.

(D) Example of Use for Solid-Phase Synthesis Other than Solid-Phase Synthesis of Peptides For example, the treatment apparatuses 1 to 4 described in the foregoing embodiments may be used for solid-phase synthesis using solid-phase resins and the like other than solid-phase synthesis of peptides, such as solid-phase synthesis of nucleotide chains such as DNAs. Solid-phase synthesis other than solid-phase synthesis of peptides is a known technique, and thus a detailed description thereof has been omitted. For example, solid-phase synthesis of nucleotide chains such as DNAs is a known technique, and thus a detailed description thereof has been omitted.

If the treatment apparatuses 1 to 4 described in the foregoing embodiments are used for solid-phase synthesis other than solid-phase synthesis of peptides, the description of solid-phase resins of peptides in the foregoing embodiments may be read, for example, as a description of solid-phase resins used for solid-phase synthesis of those other than peptides. For example, if the treatment apparatuses are used for solid-phase synthesis other than solid-phase synthesis of peptides, the first filter 105, the second filter 107, the first reflecting filter 205, and the second reflecting filter 206 for separating solid-phase resins used for solid-phase synthesis of peptides from the contents may be taken as the first filter 105 or the first reflecting filter 205 for separating solid-phase resins used for solid-phase synthesis of those other than peptides from the contents. The same applies to the second filter 107 and the second reflecting filter 206 in the case in which the treatment apparatuses 3 and 4 in Embodiments 3 and 4 are used for solid-phase synthesis of those other than peptides. For example, the multiple holes of the first filter 105, the second filter 107, the first reflecting filter 205, and the second reflecting filter 206 may be set to holes with a size that does not allow solid-phase resins used for solid-phase synthesis of those other than peptides contained in the contents to pass through the holes, and that allows the contents other than the solid-phase resins to pass through the holes. If the treatment apparatus 1 in the modified examples of Embodiment 1 shown in FIGS. 3B and 3C is used for solid-phase synthesis other than solid-phase synthesis of peptides, the first reflecting member 106 through which solid-phase resins used for solid-phase synthesis of peptides can pass through may be read, for example, as the first reflecting member 106 through which solid-phase resins used for solid-phase synthesis of those other than peptides can pass. For example, as the first reflecting member 106, a member having holes with a size that allows solid-phase resins used for solid-phase synthesis of those other than peptides to pass through the holes may be used. If the treatment apparatus 2 in Embodiment 2 shown in FIG. 4 is used for solid-phase synthesis other than solid-phase synthesis of peptides, the first reflecting filter 205 having multiple holes for separating solid-phase resins used for solid-phase synthesis of peptides from the contents may be taken, for example, as the first reflecting filter 205 having multiple holes for separating solid-phase resins used for solid-phase synthesis of those other than peptides from the contents. The materials and the like of the first filter 105, the second filter 107, the first reflecting member 106, the second reflecting member 108, the first reflecting filter 205, and the second reflecting filter 206, and the like may be similar to those in the treatment apparatuses 1 to 4 in the foregoing embodiments.

Furthermore, if the treatment apparatuses 1 to 4 described in the foregoing embodiments are used for treatment other than solid-phase synthesis, the description of solid-phase resins in the foregoing embodiments may be read as a description of solids that are to be separated, contained in the contents of the vessel 101, as in the above-described case of use for solid-phase synthesis of those other than peptides.

The treatment other than solid-phase synthesis of peptides performed using the treatment apparatuses 1 to 4 as described above may be performed using the columns described in Embodiments 5 and 6 above. Also in this case, effects similar to those described above are achieved. In this case, the vessel 101, the first filter 105, the second filter 107, the first reflecting member 106, the second reflecting member 108, the first reflecting filter 205, and the second reflecting filter 206 in the description above may be read as the cylindrical member 501, the first filter 502, the second filter 504, the first reflecting member 503, the second reflecting member 505, the first reflecting filter 603, and the second reflecting filter 605, respectively.

Furthermore, if the columns 5 and 6 described in Embodiments 5 and 6 above are used for solid-phase synthesis other than solid-phase synthesis of peptides, the description of solid-phase resins of peptides in the foregoing embodiments may be read, for example, as a description of solid-phase resins used for solid-phase synthesis of those other than peptides. For example, if the columns 5 and 6 are used for solid-phase synthesis of nucleotide chains, the description of solid-phase resins of peptides in the foregoing embodiments may be read, for example, as description of solid-phase resins used for solid-phase synthesis of nucleotide chains. If the columns 5 and 6 are used for treatment other than solid-phase synthesis, the description of solid-phase resins in the foregoing embodiments may be read as a description of solids that are to be separated, contained in the contents of the cylindrical member 501, as in the above-described case of use for solid-phase synthesis of those other than peptides.

Embodiment 7

Hereinafter, a case will be described in which the treatment apparatus 1 shown in FIG. 1 described in Embodiment 1 above is used for solid-phase synthesis of nucleotide chains performed through microwave irradiation, which is solid-phase synthesis treatment other than solid-phase synthesis of peptides. The solid-phase synthesis of nucleotide chains performed through microwave irradiation is, for example, solid-phase synthesis of nucleotide chains including one or more steps performed through microwave irradiation.

The description of solid-phase resins in Embodiment 1 above may be read, for example, as a description of solid-phase resins used for solid-phase synthesis of nucleotide chains. For example, if the treatment apparatus 1 shown in FIG. 1 described in Embodiment 1 is used for solid-phase synthesis of nucleotide chains, the first filter 105 for separating solid-phase resins used for solid-phase synthesis of peptides from the contents may be taken as the first filter 105 for separating solid-phase resins used for solid-phase synthesis of nucleotide chains from the contents. For example, the multiple holes of the first filter 105 may be set to holes with a size that does not allow solid-phase resins used for solid-phase synthesis of nucleotide chains contained in the contents to pass through the holes, and that allows the contents other than the solid-phase resins used for solid-phase synthesis of nucleotide chains to pass through the holes. The materials and the like of the first filter 105, the first reflecting member 106, and the like may be, for example, similar to those in the treatment apparatus 1 in the foregoing embodiment.

A nucleotide chain is a chain in which two or more nucleotides are bound to each other. A nucleotide chain is, for example, a chain in which two or more nucleotides are in a phosphodiester bond. There is no limitation on the number of nucleotides constituting one nucleotide chain, as long as it is two or more. A nucleotide chain may be, for example, an oligonucleotide in which about 20 or less nucleotides are bound to each other, or may be a polynucleotide in which the number of nucleotides bound to each other is larger than that in an oligonucleotide. There is no limitation on the type of a base contained in each of multiple nucleotides constituting one nucleotide chain, the sequence order of bases contained in multiple nucleotides constituting one nucleotide chain, and the like. A sugar contained in multiple nucleotides constituting one nucleotide chain is, for example, deoxy-D-ribose or D-ribose, or may be other sugars. A nucleotide chain is, for example, a chain in which multiple ribonucleotides or deoxyribonucleotides are bound to each other. A nucleotide chain is, for example, a nucleic acid such as a DNA (deoxyribonucleic acid) or an RNA (ribonucleic acid). A terminus of a nucleotide bound to a nucleotide chain synthesized in this embodiment, on the side opposite to the side on which solid-phase resins are bound, may have a structure different from that of an ordinary terminus of a nucleotide, for example, because an unshown protecting group or the like is bound thereto or because a phosphate group or the like is not added thereto.

Examples of the method of solid-phase synthesis of binding nucleotides to solid-phase resins, thereby elongating a nucleotide chain include a phosphate triester method, an H-phosphinate method, a phosphoramidite method, and the like, and, currently, solid-phase synthesis using a phosphoramidite method is most widely used. A phosphoramidite method is composed of four steps (I) to (IV) below, and a nucleotide chain is synthesized by repeating these steps.

The material, the size, and the like of the solid-phase resins used for solid-phase synthesis of nucleotide chains may be similar to those of the solid-phase resins used for solid-phase synthesis of peptides described in the foregoing embodiments. There is no limitation on the solid-phase resins that are to be used, as long as it can be used for solid-phase synthesis of nucleotide chains.

Hereinafter, the phosphoramidite method will be briefly described. The solid-phase resins used for solid-phase synthesis may be similar to the solid-phase resins in the foregoing embodiments. Note that the size, the material, and the like of the solid-phase resins may be the same as or different from those of the solid-phase resins used for solid-phase synthesis of peptides.

(I) A DMTr (dimethoxytrityl) group, which is a protecting group of a 5'-OH group of a nucleoside bound to solid-phase resins, is removed using a deprotecting agent such as a trichloroacetic acid solution.

(II) A nucleoside phosphoramidite compound activated by an activator such as tetrazole is condensed with the deprotected nucleoside bound to the solid-phase resins.

(III) A 5'-OH group of a nucleoside bound to the solid-phase resins, to which a nucleoside phosphoramidite compound has not been bound, is protected through acetylation using acetic anhydride or the like.

(IV) A phosphite triester is oxidized using an oxidant such as iodine to form a phosphate triester.

Each of the steps (I) to (IV) above includes, for example, a process of performing microwave irradiation. A nucleotide chain with a target sequence is synthesized by repeating the steps (I) to (IV) above once or twice or more. Lastly, concentrated ammonia water or the like is added to the solid-phase resins to which a nucleotide chain has been bound, and thus nucleotides are extracted from the solid-phase resins and deprotection is performed.

Hereinafter, an example of treatment in the case in which the treatment apparatus 1 shown in FIG. 1 described in Embodiment 1 above is used for solid-phase synthesis of DNAs, which are a type of nucleotide chains, will be specifically described. In this example, solid-phase synthesis using the phosphoramidite method will be described as an example Note that the solid-phase synthesis of DNAs described herein is merely an example, and the content and the like of the treatment may be changed as appropriate.

In a state in which the first valve 103*a* is closed such that the contents are not discharged from the first opening portion 1011, solid-phase resins to which a hydroxy group at the 5′ terminus protected by a DMTr group is bound, and a trichloroacetic acid solution in which methylene chloride or the like is used as solvent are supplied into the vessel 101 via the second opening portion 1012. Then, deprotection is performed by irradiating the contents of the vessel 101 with microwaves at 915 MHz from the irradiation units 102, while stirring the contents with air bubbles by supplying nitrogen gas. This step corresponds to the above-described step (I). After deprotection is completed, when the first valve 103*a* is opened, the deprotecting agent among the contents of the vessel 101 is discharged to the outside. The deprotected solid-phase resins among the contents of the vessel 101 are separated from the deprotecting agent and remain on the upper face 1051 of the first filter 105.

After acetonitrile is supplied from the second opening portion 1012 and held in the vessel 101, the acetonitrile is discharged from the first opening portion 1011, and thus the deprotected solid-phase resins remaining on the upper face 1051 of the first filter 105 are washed. The washing is performed multiple times.

Next, in order to condense nucleoside having a deprotected 5′ terminus on the solid-phase resins and nucleoside phosphoramidite, for example, 1H-tetrazole as an activator, a nucleoside phosphoramidite compound having a protected 5′ terminus and used for coupling, and acetonitrile used as solvent are supplied from the second opening portion 1012 into the vessel 101, so that the 1H-tetrazole and the nucleoside phosphoramidite compound are dissolved in the acetonitrile, and, furthermore, the irradiation units 102 perform microwave irradiation, and thus nucleoside phosphoramidite and a nucleoside having a deprotected 5′ terminus and bound to solid-phase resins are bound to each other, and phosphite triester is obtained. This step corresponds to the above-described step (II). After coupling of nucleoside phosphoramidite is ended, when the first valve 103*a* is opened, the binding solution is discharged out of the vessel 101, and the solid-phase resins to which phosphite triester having a protected 5′ terminus is bound remain on the upper face 1051 of the first filter 105 without being discharged. Washing using acetonitrile as described above is repeated multiple times.

Next, in order to protect an unreacted 5′ terminus of nucleoside on the solid-phase resins, for example, acetic anhydride, a THF (tetrahydrofuran) solution of 2,6-lutidine, and a THF solution of N-methylimidazole are supplied from the second opening portion 1012 into the vessel 101, and, furthermore, the irradiation units 102 perform microwave irradiation, and thus a 5′-OH group of nucleoside coupled to the solid-phase resins is capped. This step corresponds to the above-described step (III). After capping is ended, when the first valve 103*a* is opened, the solution for capping is discharged out of the vessel 101, and the solid-phase resins having a protected 5′ terminus remain on the upper face 1051 of the first filter 105 without being discharged. Washing using acetonitrile as described above is repeated multiple times.

Next, in order to oxidize phosphite triester, for example, an iodine/pyridine/water mixture is supplied from the second opening portion 1012 into the vessel 101, and, furthermore, the irradiation units 102 perform microwave irradiation, and thus the phosphite triester is oxidized, and nucleotide is obtained. This step corresponds to the above-described step (IV). After oxidization is ended, when the first valve 103*a* is opened, the solution for oxidization is discharged out of the vessel 101 via the first opening portion 1011, and the solid-phase resins to which nucleotide is coupled remain on the upper face 1051 of the first filter 105 without being discharged. Washing using acetonitrile as described above is repeated multiple times.

In order to further elongate nucleotides, the above-described series of treatment including deprotection, coupling of nucleoside phosphoramidite, protection of an unreacted 5′ terminal hydroxy group, and oxidization may be repeated.

After elongation of nucleotide chains is ended, in order to deprotect the nucleotide chains bound to the solid-phase resins remaining on the upper face 1051 of the first filter 105 and extract them from the solid-phase resins, for example, treatment may be performed that supplies concentrated ammonia water from the second opening portion 1012 into the vessel 101 and causes the irradiation units 102 to perform microwave irradiation. The deprotected and extracted nucleotide chains are collected through sedimentation with ethanol or the like and drying.

As described above, if the treatment apparatus 1 in Embodiment 1 above is used for solid-phase synthesis of DNAs, the throughput of DNA synthesize through solid-phase synthesis can be increased as in Embodiment 1 above. If the first reflecting member 106 reflects microwaves having been transmitted through the first filter 105, the contents not containing the solid-phase resins below the first filter 105 can be made unlikely to be irradiated with microwaves, and thus it is possible to efficiently use microwaves for solid-phase synthesis treatment.

Furthermore, as described above, in solid-phase synthesis of DNAs, when each of the steps (I) to (IV) is ended, it is necessary to separate solid-phase resins from the contents and cause them to remain in the vessel 101, to discharge solvent and the like, and further to wash the solid-phase resins remaining in the vessel 101 with solvent for washing or the like, whereas, if the treatment apparatus 1 in Embodiment 1 above is used for solid-phase synthesis, the first filter 105 can separate solid-phase resins from the contents and cause them to remain in the vessel 101. Accordingly, it is possible to perform other steps and the like of solid-phase synthesis, without washing the solid-phase resins by supplying solvent for washing or the like into the vessel 101, or once extracting the solid-phase resins by supplying other materials, solvent, a solution, and the like into the vessel 101 in which the solid-phase resins have been separated. The solid-phase resins that are separated is, for example, solid-phase resins to which products and the like have been bound.

In the solid-phase synthesis described above, it is also possible that only some of the multiple sessions of treatment that are to be performed through microwave irradiation are performed through microwave irradiation, and the other sessions of treatment are performed without microwave irradiation. This case also may be considered as solid-phase synthesis using microwaves.

Above, a case was described in which the treatment apparatus 1 in Embodiment 1 above is used for solid-phase synthesis of DNAs using the phosphoramidite method, but the treatment apparatus 1 in Embodiment 1 above may be used for solid-phase synthesis of DNAs using methods other than the phosphoramidite method, such as a phosphate triester method or an H-phosphinate method. Also in this case, effects similar to those in the foregoing embodiments are achieved.

Above, a case was described in which the treatment apparatus 1 in Embodiment 1 above is used for solid-phase synthesis of DNAs, but the treatment apparatus 1 in Embodiment 1 above may be used for solid-phase synthesis of nucleotide chains other than DNAs. Also in this case, effects similar to those in the foregoing embodiments are achieved. Examples of the nucleotide chains that can be obtained through solid-phase synthesis using the treatment apparatus 1 in Embodiment 1 above include nucleic acids such as DNAs and RNAs, polynucleotides, oligonucleotides, and the like.

In the case in which nucleotide chains are obtained through solid-phase synthesis using the treatment apparatus 1 in Embodiment 1 as described above, there is no limitation on the number of nucleotides synthesized in one nucleotide chain, as long as it is two or more. For example, in the case in which the treatment apparatus 1 in Embodiment 1 above is used for solid-phase synthesis of DNAs, there is no limitation on the number of deoxyribonucleotides synthesized in one DNA, as long as it is two or more. For example, in the case in which the treatment apparatus 1 in Embodiment 1 above is used for solid-phase synthesis of RNAs, there is no limitation on the number of ribonucleotides synthesized in one RNA, as long as it is two or more.

Above, a case was described in which the treatment apparatus 1 in Embodiment 1 is used for solid-phase synthesis of DNAs, but, for example, the treatment apparatus 1 in the modified examples of Embodiment 1 above as shown in FIG. 3A to 3C or the treatment apparatus 2 in Embodiment 2 above as shown in FIG. 4 may be used for solid-phase synthesis of nucleotide chains such as nucleic acids such as DNAs and RNAs, polynucleotides, oligonucleotides, and the like. Also in this case, effects similar to those in the modified examples of Embodiment 1 and Embodiment 2.

In the case in which the treatment apparatus 1 in the modified examples of Embodiment 1 above as shown in FIG. 3A to 3C or the treatment apparatus 2 in Embodiment 2 above as shown in FIG. 4 is used for solid-phase synthesis of nucleotide chains, for example, the description of solid-phase resins in the modified examples of Embodiment 1 above and Embodiment 2 above may be read as a description of solid-phase resins used for solid-phase synthesis of nucleotide chains.

Furthermore, the treatment apparatuses 3 and 4 described in Embodiments 3 and 4 above may be used for solid-phase synthesis of nucleotide chains such as DNAs and RNAs, polynucleotides, oligonucleotides, and the like as described above. In this case, the description of solid-phase resins in Embodiments 3 and 4 may be read as a description of solid-phase resins used for solid-phase synthesis of nucleotide chains.

For example, in the case in which the solid-phase synthesis treatment of DNAs using the phosphoramidite method using the treatment apparatus 1 as described above is performed using the treatment apparatus 3, it is possible that solid-phase resins to which a hydroxy group at the 5' terminus protected by a DMTr group is bound are supplied from the third opening portion 1011c into the vessel 301, and other solutions, a washing liquid, and the like are supplied from the second opening portion 1011b into the vessel 301. Furthermore, it is possible that the treatment that is performed via the first opening portion 1011 is performed via the first opening portion 1011a.

Furthermore, the column 5 in the modified examples of Embodiment 5 above as shown in FIG. 12A to 12C and 13A to 13C or the column 6 in Embodiment 6 above as shown in FIG. 14 may be used for solid-phase synthesis of nucleotide chains such as DNAs and RNAs, polynucleotides, oligonucleotides, and the like as described above. In this case, the description of solid-phase resins in Embodiments 5 and 6 may be read as a description of solid-phase resins used for solid-phase synthesis of nucleotide chains. It is possible that the contents and the like that are suppled or discharged through the second opening portion 5012b are suppled or discharged through the tube 702b, and the contents and the like that are suppled or discharged through the first opening portion 5012b are suppled or discharged through the tube 702a. Also in the case in which nucleotide chains are obtained through solid-phase synthesis using the column 5 or 6 as described above, there is no limitation on the number of nucleotides synthesized in one nucleotide chain, as long as it is two or more.

In the foregoing embodiments, a case was described in which solid-phase resins are used in solid-phase synthesis performed using the treatment apparatus or the column, but a solid-phase synthesis carrier other than the solid-phase resins may be used, as long as it is a solid-phase synthesis carrier that can be used for solid-phase synthesis. In the case in which a solid-phase synthesis carrier other than the solid-phase resins is used instead of the solid-phase resins, for example, the description of solid-phase resins may be read as a solid-phase synthesis carrier other than the solid-phase resins.

Furthermore, a case was described in which, in the treatment apparatuses 1 to 4 described in the foregoing embodiments, a first opening portion such as the first opening portion 1011 or the first opening portion 1011a is used as an opening portion for discharging the contents of the vessel 101, but the first opening portion may be used as an opening portion for discharging the contents, or may be used as an opening portion for supplying the contents, that is, there is no limitation on whether the opening portion is used for a discharge port or a supply port. In a similar manner, a case was described in which a second opening portion such as the second opening portion 1012 or the second opening portion 1011b is used as an opening portion for supplying the contents into the vessel 101, but the second opening portion may be used as an opening portion for supplying the contents, or may be used as an opening portion for discharging the contents, that is, there is no limitation on whether the opening portion is used for a supply port or a discharge port. For example, it is also possible that, in the treatment apparatuses 1 to 4, the first opening portion (e.g., the first opening portion 1011 or the first opening portion 1011a) is used as a supply port for supplying the contents into the vessel 101 so that the contents are supplied from the lower end of the vessel 101 side, and the second opening portion (e.g., the second opening portion 1012 or the second opening portion 1011b) is used as a discharge port for discharging the contents of the vessel 101 so that the contents are discharged from the upper end side of the vessel 101. It is also possible that one or more sessions of treatment among the sessions of treatment performed using any one of the treatment apparatuses 1 to 4 are performed while supplying the contents from the first opening portion (e.g., the first opening portion 1011 or the first opening portion 1011*a*) side and discharging the contents from the second opening portion, and one or more sessions of treatment other than these sessions of treatment are performed while supplying the contents from the second opening portion (e.g., the second opening portion 1012 or the second opening portion 1011*b*) side and discharging the contents from the first opening portion. In such treatment, it is possible to continuously supply and discharge the contents, or to non-continuously supply and discharge the contents. The state in which the contents are non-continuously supplied and discharged may include, for example, a state in which supply and discharge of the contents are temporarily stopped. The state in which the contents are non-continuously supplied and discharged may be considered, for example, as a state in which supply and discharge of the contents are intermittently performed.

For example, in the case in which the vessel 101 or the vessel 301 has another unit, for example, for supplying and discharging the contents from the first end 1015*a* side, such as the cases in which an openable door is provided at part of the first end 1015*a* side of the vessel 101 or the vessel 301, in which the first end 1015*a* side of the vessel 101 or the vessel 301 is detachable, and in which part of the first end 1015*a* side of the vessel 101 or the vessel 301 is detachable, the first opening portion 1011 or the first opening portion 1011*a* may be omitted. In a similar manner, for example, in the case in which the vessel 101 or the vessel 301 has another unit or the like, for example, for supplying and discharging the contents from the second end 1015*b* side, the second opening portion 1012 or the second opening portion 1011*b* may be omitted. In a similar manner, in the case in which the vessel 101 or the vessel 301 has another unit for supplying substances used for solid-phase synthesis, liquids, and the like to the region between the first filter 105 and the second filter 107 or the region between the first reflecting filter 205 and the second reflecting filter 206, the third opening portion 1011*c* may be omitted. For example, in the case in which the upper portion, the side face, or the like of the vessel 101 or the vessel 301 is detachable, at least either the second opening portion 1012, or the second opening portion 1011*b* and the third opening portion 1011*c* may be omitted. For example, in the treatment apparatuses 3 and 4, if materials used for solid-phase synthesis and the like other than the solid-phase resins that are supplied into the vessel 301 are supplied from the third opening portion 1011*c*, the second opening portion 1011*b* may be omitted.

Furthermore, a case was described in which, in the columns 5 and 6 or the like in the foregoing embodiments, the first opening portion 5012*a* at the first end 5011*a* of the cylindrical member 501 is used as a discharge port, but the first opening portion 5012*a* at the first end 5011*a* may be used as a discharge port for discharging the contents, or may be used as a supply port for supplying the contents, that is, there is no limitation on whether the opening portion is used for a discharge port or a supply port. In a similar manner, that is, there is no limitation on whether the second end 5011*b* is used for a supply port or a discharge port. For example, the first opening portion 5012*a* at the first end 5011*a* of the cylindrical member 501 may be used as a supply port, and the second opening portion 5012*b* at the second end 5011*b* may be used as a discharge port. It is also possible that one or more sessions of treatment among the sessions of treatment performed using the column 5 or 6 are performed while supplying the contents from the second opening portion 5012*b* at the second end 5011*b* of the cylindrical member 501 and discharging the contents from the first opening portion 5012*a* at the first end 5011*a*, and one or more sessions of treatment other than these sessions of treatment while supplying the contents from the first opening portion 5012*a* at the first end 5011*a* and discharging the contents from the second opening portion 5012*b* at the second end 5011*b*. In such treatment, it is possible to continuously supply and discharge the contents, or to non-continuously supply and discharge the contents. The state in which the contents are non-continuously supplied and discharged may include, for example, a state in which supply and discharge of the contents are temporarily stopped. The state in which the contents are non-continuously supplied and discharged may be considered, for example, as a state in which supply and discharge of the contents are intermittently performed.

Furthermore, it is also possible that, in the treatment apparatus or the column in the foregoing embodiments, the contents flow between the first opening portion (e.g., the first opening portion 1011, the first opening portion 1011*a*, or the first opening portion 5012*a*) and the second opening portion (e.g., the second opening portion 1012, the second opening portion 1011*b*, or the second opening portion 5012*b*) in the vessel (e.g., in the vessel 101, the vessel 301, or the cylindrical member 501). For example, it is also possible to cause the contents to flow through the vessel from the second opening portion side toward the first opening portion side, by continuously supplying the contents from the second opening portion into the vessel and continuously discharging the contents of the vessel from the first opening portion. In particular, in the treatment apparatuses 3 and 4 and the columns 5 and 6, it is also possible to cause the contents to flow through the vessel from the first opening portion side toward the second opening portion side, by continuously supplying the contents from the first opening portion into the vessel and continuously discharging the contents of the vessel from second opening portion. In this case, for example, the second filter 107, the second reflecting filter 206, the second filter, 504 or the second reflecting filter 605 functions as a filter that prevents solids such as solid-phase resins in the vessel 301 or the cylindrical member 501 from being discharged together with the contents. The flow direction in the vessel may be either of those described above. The flow direction in the vessel may be changed during the treatment or in accordance with steps constituting the treatment.

Furthermore, in the treatment apparatus or the column in the foregoing embodiments, as described above, it is also possible to perform microwave irradiation into the vessel in a state in which the contents continuously flow inside the vessel (e.g., the vessel 301, or the cylindrical member 501). For example, it is also possible that one or more sessions of treatment through microwave irradiation among the sessions of treatment performed using any one of the treatment apparatuses 1 to 4 and the columns 5 and 6 are performed while causing the contents to continuously flow inside the vessel. For example, it is also possible to perform microwave irradiation while causing the contents to continuously flow inside the vessel from the first opening portion side toward the second opening portion side. For example, the treatment apparatus or the column may be used as a so-called flow-type treatment apparatus or flow-type column capable of performing treatment on the contents that flow inside the vessel.

Furthermore, it is also possible that one or more sessions of treatment among the multiple sessions of treatment using the treatment apparatus or the column in the foregoing embodiments are performed while causing the contents to flow inside the vessel from the first opening portion side toward the second opening portion side, and one or more sessions of treatment other than these one or more sessions of treatment are performed while causing the contents to flow inside the vessel from the second opening portion side toward the first opening portion side. The one or more of multiple sessions of treatment may be considered as one or more steps of multiple steps contained in treatment.

Furthermore, in Embodiments 3 and 4 above, a case was described in which the treatment apparatuses 3 and 4 include the first filter 105 and the first reflecting member 106, and the second filter 107 and the second reflecting member 108, but only one combination of the first filter 105 and the first reflecting member 106, and the second filter 107 and the second reflecting member 108 may be used. The same applies to the first reflecting filter 205 configured from the first filter 105 and the first reflecting member 106 together, and the second reflecting filter 206 configured from the second filter 107 and the second reflecting member 108 together.

Furthermore, in Embodiments 1 and 2 above, a case was described as an example in which the first end 1015a is the lower end of the vessel 101, and the second end 1015b is the upper end of the vessel 101, but it is also possible that the first end 1015a is the upper end of the vessel 101, and the second end 1015b is the lower end of the vessel 101. The first end 1015a and the second end 1015b may be neither the upper end nor the lower end of the vessel 101. For example, the first end 1015a and the second end 1015b may be both ends substantially in the horizontal direction of the vessel 101. The same applies to the vessel 301 in Embodiments 3 and 4 above and the cylindrical member 501 in Embodiments 5 and 6 above.

Furthermore, in Embodiments 1 and 2 above, a case was described in which the vessel 101 is a vertical-type vessel, but the vessel 101 may have any shape, and, for example, may be a horizontal-type vessel. The horizontal-type vessel is, for example, a vessel whose longitudinal direction is along the horizontal direction. In the case in which the vessel 101 is a horizontal-type vessel, the first end 1015a and the second end 1015b of the vessel 101 are portions at both ends in the horizontal direction, which corresponds to the longitudinal direction of the vessel 101. In the case in which the vessel 101 is, for example, a horizontal-type vessel, it is possible to set the region in which solids such as solid-phase resins of the contents exist without changing the size and the like of the vessel 101, by locating the first filter 105 and the first reflecting member 106 between the irradiating position and the first end 1015a of the vessel 101 and locating the second filter 107 and the second reflecting member 108 between the irradiating position and the second end 1015b of the vessel 101, so that this region can be irradiated with most of microwaves emitted in the irradiation. Thus, it is possible to perform proper microwave irradiation according to the amount of solid-phase resins and the like. In the case in which the vessel 101 is a horizontal-type vessel, the longitudinal direction may be inclined up to approximately 30 degrees relative to the horizontal direction. For example, a vessel holding unit or the like may be provided, such as a stage (not shown) on which the vessel 101 in a state of being inclined is placed, a suspending apparatus on which the vessel 101 may be located and suspended such that the vessel 101 is inclined, or the like. The same applies to the vessel 301 in Embodiments 3 and 4 above.

Furthermore, in Embodiments 5 and 6 above, a case was described in which the column is used in a state in which the axial direction of the cylindrical member 501 is along the vertical direction, but the column may be used, for example, in a state in which the axial direction of the cylindrical member 501 is along the horizontal direction. The column may be used in a state in which the axial direction is inclined. For example, the column may be used in a state in which the axial direction is inclined up to approximately 30 degrees relative to the horizontal direction. For example, a holding unit or the like for holding the cylindrical member 501 with its axial direction being inclined may be provided, such as a stage (not shown) on which the cylindrical member 501 with its axial direction being inclined is placed, a suspending apparatus on which the cylindrical member 501 is suspended in a state of being inclined.

Furthermore, the vessel 101 and the vessel 301 in the foregoing embodiments may be each constituted by multiple members. For example, in Embodiments 3 and 4 above, if the vessel 301 is a vessel 101 of a vertical-type and the second end 1015b is the upper end of the vessel 101, for example, the vessel 101 may be constituted by a first member (not shown) whose upper portion is open and lower portion forms a first end, and a second member (not shown) configured to be coupled to the opening upper portion of the first member and whose upper portion forms the second opening portion 1011b. In this case, the second member may be a pipe-like member configured to be coupled to the upper portion of the first member. In this case, the second filter 107 and the second reflecting member 108 may be located on the upper portion side of the first member, and, furthermore, either one of them may be provided so as to obstruct the opening upper portion of the first member.

The present invention is not limited to the foregoing embodiment. Various modifications are possible within the scope of the present invention.

As described above, the treatment apparatus according to the present invention is suitable as an apparatus used for treatment performed through microwave irradiation, and is useful especially as an apparatus and the like used for treatment including a step of filtering solids.

The invention claimed is:

1. A treatment apparatus comprising:
    a vessel made of a microwave-reflecting material, having a first end, and an opening portion emitting microwaves into the vessel;
    a first filter located so as to partition the vessel, and configured to separate solids that are to be separated, from contents held in the vessel; and
    a first reflecting member located closer to the first end than a position of the opening portion and so as to partition the vessel, the first reflective member partitioning a space in the vessel to suppress microwave irradiation by reflecting microwaves to the opposite side of the first end with respect to the first filter, and configured to allow at least one of the contents having passed through the first filter to pass through the first reflecting member or allow the at least one of the contents having passed through the first reflecting member to pass through the first filter.

2. The treatment apparatus according to claim 1, wherein the first reflecting member is located closer to the first end than the first filter is, or between the first filter and the opening portion.

3. The treatment apparatus according to claim 1, wherein the first filter and the first reflecting member are laid over each other.

4. The treatment apparatus according to claim 1, wherein the first reflecting member is located between the first filter and the opening portion, and configured to allow the solid to pass through the first reflecting member.

5. The treatment apparatus according to claim 1, wherein the first filter and the first reflecting member together configure a first reflecting filter that separates solids that are to be separated, from contents of the vessel, and that reflects microwaves.

6. The treatment apparatus according to claim 1,
wherein the vessel further has a second end,
the opening portion is provided between the first end and the second end of the vessel, and
the treatment apparatus further comprises:
 a second filter located closer to the second end than the first filter and the first reflecting member so as to partition the vessel, and configured to separate solids that are to be separated, from contents held in the vessel; and
 a second reflecting member located closer to the second end than the positions of the first filter and the opening portion and so as to partition the vessel, the second reflective member partitioning a space in the vessel to suppress microwave irradiation by reflecting microwaves to the opposite side of the second end with respect to the second filter, and configured to allow at least one of the contents having passed through the second filter to pass through the second reflecting member or allow the at least one of the contents having passed through the second reflecting member to pass through the second filter.

7. The treatment apparatus according to claim 6, wherein the second reflecting member is located closer to the second end than the second filter is, or between the second filter and the opening portion.

8. The treatment apparatus according to claim 6, wherein the second filter is laid over the second reflecting member.

9. The treatment apparatus according to claim 6, wherein the second reflecting member is located between the second filter and the opening portion, and configured to allow the solid to pass through the second reflecting member.

10. The treatment apparatus according to claim 6, wherein the second filter and the second reflecting member together configure a second reflecting filter that separates solids that are to be separated, from contents of the vessel, and that reflects microwaves.

11. The treatment apparatus according to claim 1, wherein, in the vessel, a first opening portion through which at least one of supply and discharge of contents is performed is located closer to the first end than the first filter and the first reflecting member are.

12. The treatment apparatus according to claim 6, wherein, in the vessel, a first opening portion through which at least one of supply and discharge of contents is performed is located closer to the first end than the first filter and the first reflecting member are, and a second opening portion through which at least one of supply and discharge of contents is performed is located closer to the second end than the second filter and the second reflecting member are.

13. The treatment apparatus according to claim 11,
wherein the first end is a lower end of the vessel, and the first opening portion is a discharge port for discharging contents.

14. The treatment apparatus according to claim 12, wherein microwave irradiation from the opening portion is performed between the first opening portion and the second opening portion in a state in which contents flow inside the vessel.

15. The treatment apparatus according to claim 12, for performing:
 treatment that is performed inside the vessel while supplying contents from the first opening portion and discharging the contents from the second opening portion; and
 treatment that is performed inside the vessel while supplying contents from the second opening portion and discharging the contents from the first opening portion.

16. The treatment apparatus according to claim 6,
wherein the vessel is a cylindrical member having a first end that is open and a second end that is open,
the opening portion of the vessel is provided on a side face of the cylindrical member,
the first filter is located so as to obstruct a first end side of the cylindrical member,
the first reflecting member is located so as to obstruct the first end side of the cylindrical member,
the second filter is located so as to obstruct a second end side of the cylindrical member, and
the second reflecting member is located so as to obstruct the second end side of the cylindrical member.

17. The treatment apparatus according to claim 16, wherein the treatment apparatus is a column.

18. The treatment apparatus according to claim 1,
wherein the treatment apparatus is a treatment apparatus used for solid-phase synthesis, and
the solid is a solid-phase synthesis carrier used for solid-phase synthesis.

19. The treatment apparatus according to claim 18, wherein the solid-phase synthesis is solid-phase synthesis for synthesizing a peptide or a nucleotide chain bound to a solid-phase synthesis carrier.

20. The treatment apparatus according to claim 1, wherein the treatment apparatus is a treatment apparatus in which microwave irradiation is performed in a multi-mode.

21. The treatment apparatus according to claim 1, wherein the treatment apparatus further includes an irradiation unit configured to perform microwave irradiation from the opening portion into the vessel.

* * * * *